US007745424B2

(12) United States Patent
Ralston et al.

(10) Patent No.: US 7,745,424 B2
(45) Date of Patent: Jun. 29, 2010

(54) ALKANE DIOL DERIVATIVES AS THERAPEUTIC AGENTS FOR THE TREATMENT OF BONE CONDITIONS

(75) Inventors: Stuart H Ralston, Aberdeen (GB); Iain R Greig, Aberdeen (GB); Robert J Van't Hof, Aberdeen (GB); Kenneth J Armour, York (GB)

(73) Assignee: The Univeristy Court of the University of Aberdeen, Aberdeen (GB)

( * ) Notice: Subject to any disclaimer, the term of this patent is extended or adjusted under 35 U.S.C. 154(b) by 1079 days.

(21) Appl. No.: 10/494,327

(22) PCT Filed: Oct. 31, 2002

(86) PCT No.: PCT/GB02/04933

§ 371 (c)(1),
(2), (4) Date: Jul. 28, 2004

(87) PCT Pub. No.: WO03/037321

PCT Pub. Date: May 8, 2003

(65) Prior Publication Data

US 2004/0254151 A1 Dec. 16, 2004

(30) Foreign Application Priority Data

Oct. 31, 2001 (GB) ................................. 0126157.7

(51) Int. Cl.
*A61K 31/66* (2006.01)
*A61K 31/225* (2006.01)
(52) U.S. Cl. ........................ 514/124; 514/547; 514/685
(58) Field of Classification Search ................... 514/79, 514/411, 433, 730, 685, 640, 114, 553, 75; 548/444; 568/331; 564/257; 549/14
See application file for complete search history.

(56) References Cited

U.S. PATENT DOCUMENTS 4,077,997 A   3/1978   Blum et al.
5,374,707 A * 12/1994   Asrar et al. ................. 528/272

FOREIGN PATENT DOCUMENTS

| GB | 661185 | 11/1951 |
|---|---|---|
| GB | 663072 | 12/1951 |
| GB | 716877 | 10/1954 |
| GB | 774180 | 2/1956 |
| GB | 774635 | 5/1957 |
| GB | 1 230 840 | 5/1971 |
| GB | 1 272 820 | 5/1972 |
| GB | 1 351 243 | 4/1974 |
| JP | 43-26316 | 11/1968 |
| JP | 02-104562 | 4/1990 |
| JP | 07101922 | * 4/1995 |
| WO | WO 94/12463 | 6/1994 |
| WO | WO 01/046135 A1 | 6/2001 |

OTHER PUBLICATIONS

Kumar et al., "Hyperbranched polyurethanes with varying spacer segments between the branching points," Journal of Polymer Science: Part A: Polymer Chemistry, 34, 1996, pp. 839-848.*
Kong et a., "Synthesis, Mesomorphism, Isomerization, and Aromatization of Stereoregular Poly{[4-({[6-({[4'-(heptyl)oxy-4-biphenylyl]carbonyl}oxy)-hexyl]oxy}carbonyl)phenyl]acetylene}", Macromolecules, 1999, 32, pp. 1722-1730.*
Armour K.J., et al., 2001, "Inhibition of bone resorption in vitro and prevention of ovariectomy-induced bone loss in vivo by flurbiprofen nitroxybutylester (HCT1026), " *Arthritis and Rheumatism*, vol. 44, No. 9, pp. 2185-2192.
Burgaud, J.L., et al., 1999, "HCT-1026: Treatment of Septic Shock, Treatment of Urinary Incontinence, Treatment of Osteoporosis, Nitric Oxide Donor," *Drugs of the Future*, vol. 24, No. 8, pp. 858-861.
Burgaud, J.L., et al., 2002, "Nitric-Oxide Releasing Molecules: A New Class of Drugs with Several Major Indications," *Current Pharmaceutical Design*, vol. 8, No. 3, pp. 201-213.
Coxon, F.P., Helfrich, M.H., Van't Hof, R., Sebti, S., Ralston, S.H., Hamilton, A., and Rogers, M.J., 2000, "Protein geranylgeranylation is required for osteoclast formation, function, and survival: inhibition by bisphosphonates and GGTI-298," *J.Bone Miner.Res.*, vol. 15, pp. 1467-1476.
Degenhardt and Burdsall, 1986, "Synthesis of Ethenylidenebis(phosphonic acid) and its Tetraalkyl Esters," *J. Org. Chem.*, vol. 51, pp. 3488-3490.
Del Soldato, P., et al., 1999, "NO-aspirins: a class of new antiinflammatory and antithrombotic agents," *Trends in Pharmacological Sciences*, vol. 20, No. 8, pp. 319-323.
Eberhard and Westheimer, 1965, "Hydrolysis of Phostonates," *J. Amer. Chem. Soc.*, vol. 87, pp. 253-260.
Herczegh et al, 2002, "Osteoadsorptive Bisphosphonate Derivatives of Fluoroquinolone Antibacterials," *J. Med. Chem.*, vol. 45, pp. 2338-2341.

(Continued)

*Primary Examiner*—Sreeni Padmanabhan
*Assistant Examiner*—Sahar Javanmard
(74) *Attorney, Agent, or Firm*—Nixon & Vanderhye P.C.

(57) ABSTRACT

The present invention pertains to certain alkane diol derivatives (including, e.g., mono- and di-esters) of the formula $R^1$—O-A-O—$R^2$, wherein: A is a $C_{2-10}$ alkylene group; $R^1$ is independently a first hydroxy protecting group (e.g., an ester group); and, $R^2$ is independently —H or a second hydroxy protecting group (e.g., an ester group); and pharmaceutically acceptable salts, solvates, amides, esters, ethers, chemically protected forms, and prodrug thereof, which, inter alia, inhibit osteoclast survival, formation, and/or activity; and/or inhibit bone resorption. The present invention also pertains to pharmaceutical compositions comprising such compounds, and the use of such compounds and compositions, both in vitro and in vivo, to inhibit osteoclast survival, formation, and/or activity, and to inhibit conditions mediated by osteoclasts and/or characterised by bone resorption, such as osteoporosis, rheumatoid arthritis, cancer associated bone disease, Paget's disease, and the like; and/or conditions associated with inflammation or activation of the immune system.

100 Claims, 10 Drawing Sheets

OTHER PUBLICATIONS

Hughes, D.E., Boyce, B.F., 1997, "Apoptosis in bone physiology and disease," *Molecular Pathology*, vol. 50, pp. 132-137.

Kong, Y.Y., Yoshida, H., Sarosi, I., Tan, H.L., Timms, E., Capparelli, C., et al, 1999, "OPGL is a key regulator of osteoclastogenesis, lymphocyte development and lymph-node organogenesis," *Nature*, vol. 397, pp. 315-323.

Luckman, S.P., Coxon, F.P., Ebetino, F.H., Russell, R.G., and Rogers, M.J., 1998, "Heterocycle-containing bisphosphonates cause apoptosis and inhibit bone resorption by preventing protein prenylation: evidence from structure- activity relationships in J774 macrophages," *J. Bone Miner.Res.*, vol. 13, pp. 1668-1678.

MacPherson, H; Noble, B.S.; Ralston, S.H., 1999, "Expression and functional role of nitric oxide synthase isoforms in human osteoblast-like cells," *Bone*, vol. 24, pp. 179-185.

Miyaura, N. and Suzuki, A., 1995, "Palladium-catalysed cross-coupling reactions of organoboron compounds," *Chem. Rev.*, vol. 95, No. 7, pp. 2457-2483.

Mundy, G.R., 1996, *Bone Remodelling and its disorders* (2nd edition), London: Martin Dunitz.

Nociari, M.N., et al., 1998, "A Novel one-step, highly sensitive fluorimetric assay to evaluate cell-mediated cytotoxicity," *Journal of Immunological Methods*, vol. 213, pp. 157-167.

Raisz, L.G., 1988, "Local and systemic factors in the pathogenesis of osteoporosis," *N. Engl. J. Med.*, vol. 318, pp. 818-828.

Ralston, S.H., 1997, "Science, Medicine and the Future: Osteoporosis," *Br. Med. J.*, vol. 315, pp. 469-472.

Rodan, G.A., Harada, S., 1997, "The missing bone," *Cell*, vol. 89, pp. 677-680.

Takahashi, N.; Akatsu, T.; Udagawa, N.; Sasaki, T.; Yamaguchi, A.; Moseley, J.M.; Martin, T.J.; Suda,T., 1988, "Osteoblastic cells are involved in osteoclast formation," *Endocrinology*, vol. 123, pp. 2600-2602, 1988.

van't Hof, R.J., and Ralston, S.H., 1997, "Cytokine-induced nitric oxide inhibits bone resorption by inducing apoptosis of osteoclast progenitors and suppressing osteoclast activity," *J. Bone Miner. Res.*, vol. 12, pp. 1797-1804.

van't Hof, R.J., et al., 1999, "NO-NSAIDs: A Novel Class of Osteoclast Inhibitors," *Calcified Tissue International*, vol. 54, No. Supplement 1, p. S59 (European Symposium on Calcified Tissues, Maastricht, Netherlands, May 7-11, 1999).

Yasuda, H., Shima, N., Nakagawa, N., Mochizuki, S.I., Yano, K., Fujise, N., et al, 1998, "Identity of osteoclastogenesis inhibitory factor (OCIF) and osteoprotegerin (OPG): a mechanism by which OPG/OCIF inhibits osteoclastogenesis in vitro," *Endocrinology*, vol. 139, pp. 1329-1337.

UK Search Report for GB 0126157.7, dated Apr. 23, 2002 (the priority application).

IPER for PCT/GB02/04933, dated Oct. 29, 2003 (the underlying PCT application).

* cited by examiner ary value, and/or to "about" another particular value.
ALKANE DIOL DERIVATIVES AS THERAPEUTIC AGENTS FOR THE TREATMENT OF BONE CONDITIONS This application is the US national phase of international application PCT/GB02/04933 filed in English on 31 Oct. 2002, which designated the US. PCT/GB02/04933 claims priority to GB Application No. 0126157.7 filed 31 Oct. 2001. The entire contents of these applications are incorporated herein by reference.

RELATED APPLICATION

This application is related to (and where permitted by law, claims priority to) United Kingdom patent application number GB 0126157.7 filed 31 Oct. 2001, the contents of which are incorporated herein by reference in their entirety.

TECHNICAL FIELD

The present invention pertains generally to the field of therapeutic compounds for treating bone conditions, and more specifically to certain alkane diol derivatives which, inter alia, inhibit osteoclast survival, formation, and/or activity; and/or inhibit bone resorption. The present invention also pertains to pharmaceutical compositions comprising such compounds, and the use of such compounds and compositions, both in vitro and in vivo, to inhibit osteoclast survival, formation, and/or activity, and to inhibit conditions mediated by osteoclasts and/or characterised by bone resorption, such as osteoporosis, rheumatoid arthritis, cancer associated bone disease, Paget's disease, and the like; and/or conditions associated with inflammation or activation of the immune system.

BACKGROUND

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiments.

Functions of Bone

The function of bone is to provide mechanical support for joints, tendons and ligaments, to protect vital organs from damage and to act as a reservoir for calcium and phosphate in the preservation of normal mineral homeostasis. Diseases of bone compromise these functions, leading to clinical problems such as bone pain, bone deformity, fracture and abnormalities of calcium and phosphate homeostasis.

Types of Bone

The normal skeleton contains two types of bone; cortical or compact bone, which makes up most of shafts (diaphysis) of the long bones such as the femur and tibia, and trabecular or spongy bone which makes up most of the vertebral bodies and the ends of the long bones.

Trabecular bone has a greater surface area than cortical bone and because of this is remodeled more rapidly. This means that conditions associated with increased bone turnover tend to affect trabecular bone more quickly and more profoundly than cortical bone. Cortical bone is arranged in so-called Haversian systems which consists of a series of concentric lamellae of collagen fibres surrounding a central canal that contains blood vessels. Nutrients reach the central parts of the bone by an interconnecting system of canaliculi that run between osteocytes buried deep within bone matrix and lining cells on the bone surface. Trabecular bone has a similar structure, but here the lamellae run in parallel to the bone surface, rather than concentrically as in cortical bone.

Bone Composition

The organic component of bone matrix comprises mainly of type I collagen; a fibrillar protein formed from three protein chains, wound together in a triple helix. Collagen type I is laid down by bone forming cells (osteoblasts) in organised parallel sheets (lamellae) and subsequently the collagen chains become cross-linked by specialised covalent bonds which help to give bone its tensile strength. When bone is formed rapidly (for example in Paget's disease, or in bone metastases), the lamellae are laid down in a disorderly fashion giving rise to "woven bone", which is mechanically weak and easily fractured. Bone matrix also contains small amounts of other collagens and several non-collagenous proteins and glycoproteins. Some of these, such as osteocalcin, are specific to bone, whereas others, such as osteopontin and fibronectin and various peptide growth factors are also found in other connective tissues. The function of non-collagenous bone proteins is unclear, but it is thought that they are involved in mediating the attachment of bone cells to bone matrix, and in regulating bone cell activity during the process of bone remodelling. The organic component of bone forms a framework upon which mineralisation occurs. During bone formation, osteoblasts lay down uncalcified bone matrix (osteoid) which contains the components described above and small amounts of other proteins, which are adsorbed from extracellular fluid. After a lag phase of about 10 days, the matrix becomes mineralised, as hydroxyapatite $((Ca_{10}(PO_4)_6(OH)_2)$ crystals are deposited in the spaces between collagen fibrils. Mineralisation confers upon bone the property of mechanical rigidity, which complements the tensile strength, and elasticity derived from bone collagen.

Bone Cell Function and Bone Remodelling

The mechanical integrity of the skeleton is maintained by the process of bone remodelling, which occurs throughout life, in order that damaged bone can be replaced by new bone. Remodelling can be divided into four phases; resorption; reversal, formation and quiescence (see, e.g., Raisz, 1988; Mundy, 1996). At any one time approximately 10% of bone surface in the adult skeleton is undergoing active remodeled whereas the remaining 90% is quiescent.

Osteoclast Formation and Differentiation

Remodelling commences with attraction of bone resorbing cells (osteoclasts) to the site, which is to be resorbed. These are multinucleated phagocytic cells, rich in the enzyme tartrate-resistant acid phosphatase, which are formed by fusion of precursors derived from the cells of monocyte/macrophage lineage. Recent work has identified several molecules that are of key importance in the regulation of osteoclast differentiation (see, e.g., Ralston, 1997). The transcription factor PU-1 which is expressed in early osteoclast precursors is necessary for the initial stages of osteoclast and monocyte differentiation, whereas other transcription factors including c-fos and NFkB play an essential role in stimulating differentiation of committed precursors to mature osteoclasts. Osteoclast formation and activation is also dependent on close contact between osteoclast precursors and bone marrow stromal cells. Stromal cells secrete the cytokine M-CSF (macrophage colony stimulating factor), which is essential for differentiation of both osteoclasts and macrophages from a common precursor. Stromal cells also express a molecule called RANK ligand (RANKL) on the cell surface, which interacts with another cell surface receptor present on osteoclast precursors called RANK (Beceptor Activator of Nuclear Factor Kappa B) to promote differentiation of osteoclast precursors to mature osteoclasts. The RANK-RANKL interaction is blocked by another molecule called Osteoprotegerin (OPG), which is a "decoy" ligand for RANK and which acts a potent inhibitor of osteoclast formation (see, e.g., Kong et al., 1999; Yasuda et al., 1998). Recent work suggests that many of the factors that promote osteoclast formation and bone resorption do so by regulating expression of these molecules.

Mature osteoclasts form a tight seal over the bone surface and resorb bone by secreting hydrochloric acid and proteolytic enzymes through the "ruffled border" into a space beneath the osteoclast (Howship's lacuna). Formation of this ruffled border is critically dependent on the presence of c-src, a cell membrane associated signalling protein. The hydrochloric acid secreted by osteoclasts dissolves hydroxyapatite and allows proteolytic enzymes (mainly Cathepsin K and matrix metalloproteinases) to degrade collagen and other matrix proteins. Molecules which have been identified as being important in regulating osteoclast activity include; carbonic anhydrase II (Ca-II) which catalyses formation of hydrogen ions within osteoclasts; TCIRG1, which encodes a subunit of the osteoclast proton pump, and Cathepsin K which degrades collagen and other non-collagenous proteins. Deficiency of these proteins causes osteopetrosis which is a disease associated with increased bone density and osteoclast dysfunction. After resorption is completed osteoclasts undergo programmed cell death (apoptosis), in the so-called reversal phase which heralds the start of bone formation. It has recently been discovered that many of the drugs, which are used clinically to inhibit bone resorption, such as bisphosphonates and oestrogen do so by promoting osteoclast apoptosis (see, e.g., Hughes et al., 1997).

Osteoblast Formation and Differentiation

Bone formation begins with attraction of osteoblast precursors, which are derived from mesenchymal stem cells in the bone marrow, to the bone surface. Although these cells have the potential to differentiate into many cell types including adipocytes, myocytes, and chondrocytes it is now known that the key trigger for osteoblast differentiation is expression of a regulatory molecule called Cbfa1 in pre-osteoblasts (see, e.g., Rodan et al., 1997). Cbfa1 is a transcription factor that activates co-ordinated expression of genes characteristic of the osteoblast phenotype such as osteocalcin, type I collagen and alkaline phosphatase. In contrast, expression of the transcription factor PPARg promotes the cells towards adipocyte differentiation. It is currently thought that some cases of osteoporosis may occur because there is an imbalance between the rate of osteoblast and adipocyte differentiation in bone. Mature osteoblasts are plump cuboidal cells, which are responsible for the production of bone matrix. They are rich in the enzyme alkaline phosphatase and the protein osteocalcin, which are used clinically as serum markers of osteoblast activity. Osteoblasts lay down bone matrix which is initially unmineralised (osteoid), but which subsequently becomes calcified after about 10 days to form mature bone. During bone formation, some osteoblasts become trapped within the matrix and differentiate into osteocytes, whereas others differentiate into flattened "lining cells" which cover the bone surface. Osteocytes connect with one another and with lining cells on the bone surface by an intricate network of cytoplasmic processes, running through cannaliculi in bone matrix. Osteocytes appear to act as sensors of mechanical strain in the skeleton, and release signalling molecules such as prostaglandins and nitric oxide (NO), which modulate the function of neighbouring bone cells.

Regulation of Bone Remodelling

Bone remodelling is a highly organised process, but the mechanisms which determine where and when remodelling occurs are poorly understood. Mechanical stimuli and areas of micro-damage are likely to be important in determining the sites at which remodelling occurs in the normal skeleton. Increased bone remodelling may result from local or systemic release of inflammatory cytokines like interleukin-1 and tumour necrosis factor in inflammatory diseases. Calciotropic hormones such as parathyroid hormone (PTH) and 1,25-dihydroxyvitamin D, act together to increase bone remodelling on a systemic basis allowing skeletal calcium to be mobilised for maintenance of plasma calcium homeostasis. Bone remodelling is also increased by other hormones such as thyroid hormone and growth hormone, but suppressed by oestrogen, androgens and calcitonin.

Common Bone Diseases

Osteoporosis is a common disease characterized by reduced bone density, deterioration of bone tissue and increase risk of fracture. Many factors contribute to the pathogenesis of osteoporosis including poor diet, lack of exercise, smoking and excessive alcohol intake. Osteoporosis may also arise in association with inflammatory diseases such as rheumatoid arthritis, endocrine diseases such as thyrotoxicosis and with certain drug treatments such as glucocorticoids. However one of the most important factors in the pathogenesis of osteoporosis is heredity.

Paget's disease of bone is a common condition of unknown cause, characterized by increased bone turnover and disorganized bone remodeling, with areas of increased osteoclastic and osteoblast activity. Although Pagetic bone is often denser than normal, the abnormal architecture causes the bone to be mechanically weak, resulting in bone deformity and increased susceptibility to pathological fracture.

Multiple Myeloma is a cancer of plasma cells. In contrast to most other haematological malignancies, the tumour cells do not circulate in the blood, but accumulate in the bone marrow where they give rise to high levels of cytokines that activate osteoclastic bone resorption (e.g., interleukin-6). The disease accounts for approximately 20% of all haematological cancers and is mainly a disease of elderly people.

Bone Resorption Inhibitors

Several common diseases, such as osteoporosis and rheumatoid arthritis, are characterised by bone loss due to excess bone resorption by osteoclasts. At present the most commonly used types of drugs used to suppress osteoclast activity in these diseases are bisphophonates (BPs) and non-steroidal anti-inflammatory drugs (NSAIDs).

Bisphonates (also know as diphosphonates) are an important class of drugs used in the treatment of bone diseases involving excessive bone destruction or resorption, e.g., Paget's disease, tumour-associated osteolysis, and post-menopausal osteoporosis. Bisphosphonates are structural analogues of naturally occurring pyrophosphate. Whereas pyrophosphate consists of two phosphate groups linked by an oxygen atom (P—O—P), bisphosphonates have two phosphate groups linked by a carbon atom (P—C—P). This makes bisphosphonates very stable and resistant to degradation. Furthermore, like pyrophosphate, bisphosphonates have very high affinity for calcium and therefore target to bone mineral in vivo. The carbon atom that links the two phosphate groups has two side chains attached to it, which can be altered in structure. This gives rise to a multitude of bisphosphonate compounds with different anti-resorptive potencies. Bone resorption is mediated by highly specialised, multinucleated osteoclast cells. Bisphosphonate drugs specifically inhibit the activity and survival of these cells. Firstly, after intravenous or oral administration, the bisphosphonates are rapidly cleared from the circulation and bind to bone mineral. As the mineral is then resorbed and dissolved by osteoclasts, it is thought that the drug is released from the bone mineral and is internalised by osteoclasts. Intracellular accumulation of the drugs inhibits the ability of the cells to resorb bone (probably by interfering with signal transduction pathways or cellular metabolism) and causes osteoclast apoptosis.

NSAIDs are widely used in the treatment of inflammatory diseases, but often cause severe gastro-intestinal (GI) side effects. NSAIDs developed by Nicox SA (Sophia Antipolis, France), that contain a nitric oxide (NO)-donor group (NO-NSAID) exhibit anti-inflammatory properties without causing GI side effects. An example of such a compound is HCT 1026, which is a nitrosylated derivative of the NSAID flurbiprofen (see, for example, Armour et al., 2001).

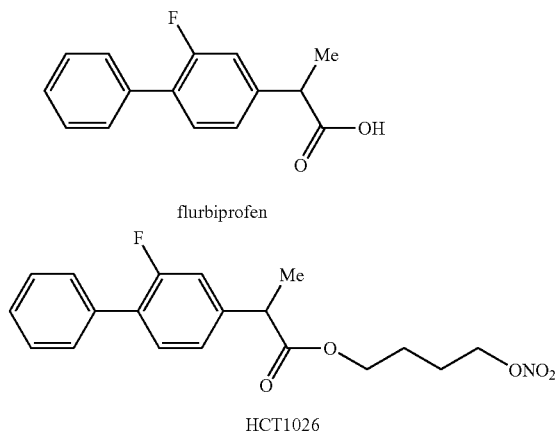

There is a recognized need for more and better treatments for these and other bone-related diseases, which offer, for example, one or more the following benefits:
(a) improved activity;
(b) improved efficacy;
(c) improved specificity;
(d) reduced toxicity (e.g., cytotoxicity);
(e) complement the activity of other treatments (e.g., chemotherapeutic agents);
(f) reduced intensity of undesired side-effects;
(g) fewer undesired side-effects;
(h) simpler methods of administration (e.g., route, timing, compliance);
(i) reduction in required dosage amounts;
(j) reduction in required frequency of administration;
(k) increased ease of synthesis, purification, handling, storage, etc.;
(l) reduced cost of synthesis, purification, handling, storage, etc.

Thus, one aim of the present invention is the provision of active compounds which offer one or more of the above benefits.

SUMMARY OF THE INVENTION

One aspect of the invention pertains to a method of inhibiting osteoclast survival, formation, and activity, in vitro or in vivo, comprising contacting an osteoclast with an effective amount of an active compound, as described herein.

Another aspect of the invention pertains to a method of inhibiting bone resorption, in vitro or in vivo, comprising contacting cells in the bone microenvironment with a therapeutically-effective amount of an active compound, as described herein.

Another aspect of the present invention pertains to a method for the treatment of a condition mediated by osteoclasts and/or characterised by bone resorption, as described herein, comprising administering to a subject suffering from said condition a therapeutically-effective amount of an active compound, as described herein, preferably in the form of a pharmaceutical composition.

Another aspect of the present invention pertains to a method for the treatment of a condition associated with inflammation or activation of the immune system, as described herein, comprising administering to a subject suffering from said condition a therapeutically-effective amount of an active compound, as described herein, preferably in the form of a pharmaceutical composition.

Another aspect of the present invention pertains to use of an active compound, as described herein, for the manufacture of a medicament for use in the treatment of a condition mediated by osteoclasts and/or characterised by bone resorption, as described herein.

Another aspect of the present invention pertains to use of an active compound, as described herein, for the manufacture of a medicament for use in the treatment of a condition mediated by osteoclasts, as described herein.

Another aspect of the present invention pertains to use of an active compound, as described herein, for the manufacture of a medicament for use in the treatment of a condition characterised by bone resorption, as described herein.

Another aspect of the present invention pertains to use of an active compound, as described herein, for the manufacture of a medicament for use in the treatment of osteoporosis, rheumatoid arthritis, cancer associated bone disease, or Paget's disease.

Another aspect of the present invention pertains to use of an active compound, as described herein, for the manufacture of a medicament for use in the treatment of a condition associated with inflammation or activation of the immune system, as described herein.

Another aspect of the present invention pertains to an active compound as described herein for use in a method of treatment of the human or animal body by therapy.

Another aspect of the present invention pertains to an active compound, as described herein, for use in a method of treatment a condition mediated by osteoclasts and/or characterised by bone resorption, as described herein, of the human or animal body by therapy.

Another aspect of the present invention pertains to an active compound, as described herein, for use in a method of treatment a condition mediated by osteoclasts, as described herein, of the human or animal body by therapy.

Another aspect of the present invention pertains to an active compound, as described herein, for use in a method of treatment a condition characterised by bone resorption, as described herein, of the human or animal body by therapy.

Another aspect of the present invention pertains to an active compound, as described herein, for use in a method of treatment of osteoporosis, rheumatoid arthritis, cancer associated bone disease, or Paget's disease of the human or animal body by therapy.

Another aspect of the present invention pertains to an active compound, as described herein, for use in a method of treatment a condition associated with inflammation or activation of the immune system, as described herein, of the human or animal body by therapy.

Another aspect of the invention pertains to active compounds, specifically, certain alkane diol derivatives (e.g., esters of alkane diols) as described herein.

Another aspect of the invention pertains to a composition comprising an active compound as described herein and a pharmaceutically acceptable carrier or diluent.

Another aspect of the present invention pertains to a kit comprising (a) an active compound, as described herein, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Figure 1:
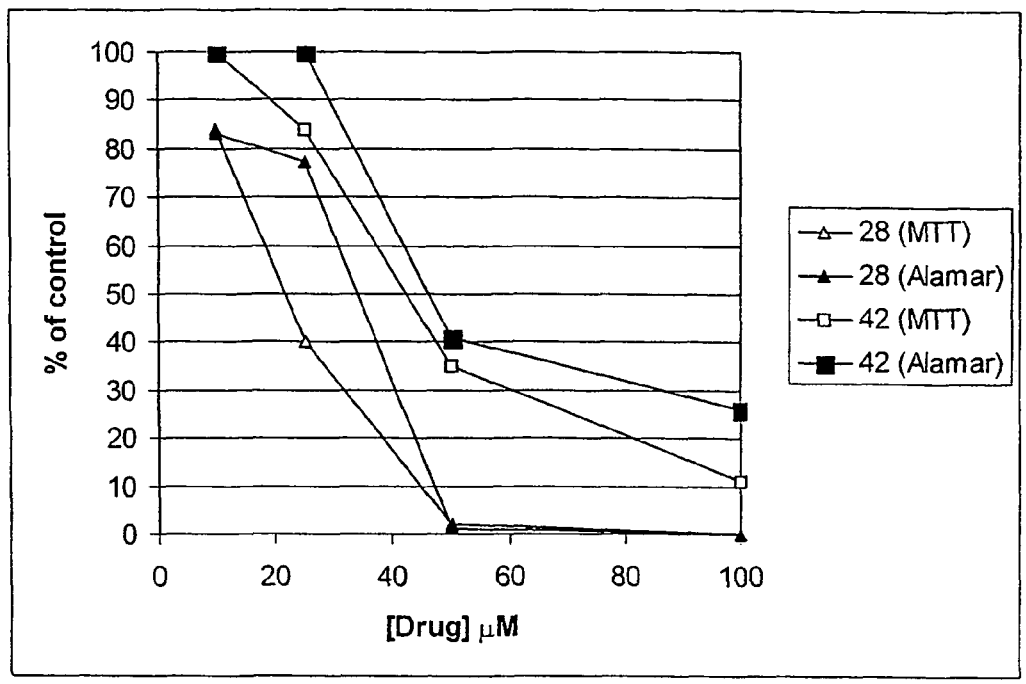
FIG. 1 is a graph of macrophage viability, as measured by the MTT and Alamar Blue macrophage J774 viability assays, expressed as % of control, after 72 hour exposure to ABD-0028 (4T) ("28") and ABD-0042 (4BPA) ("42") as a function of concentration of compound.

One aspect of the present invention pertains to compounds which may be described as alkane diol derivatives, and their surprising and unexpected osteoclast-inhibitory and resorption-inhibitory effects.

Alkane Diol Derivatives

One aspect of the present invention pertains to compounds which may be described as derivatives of the alkane diols described above (i.e., alkane diol derivatives), and which have the following formula:

(1)

wherein:
A is a $C_{2-10}$alkylene group;
$R^1$ is independently a first hydroxy protecting group; and,
$R^2$ is independently —H or a second hydroxy protecting group;

and pharmaceutically acceptable salts, solvates, amides, esters, ethers, chemically protected forms, or prodrugs thereof.

In one embodiment, $R^2$ is not —H, and the compound is di-protected.

In one embodiment, $R^2$ is not —H, and $R^1$ and $R^2$ are the same.

In one embodiment, $R^2$ is not —H, and $R^1$ and $R^2$ are different.

In one embodiment, $R^2$ is —H, the compound is mono-protected, and has the following formula:

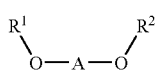

(2)

Alkane Diols

The compounds of the present invention may be described as alkane diol derivatives. In this context, the alkane diols have the following formula:

HO-A-OH (3)

wherein A is a $C_{2-10}$alkylene group, and is optionally substituted.

The Alkylene Group, A

The alkylene group, A, is a $C_{2-10}$alkylene group, and is optionally substituted.

The term "$C_{2-10}$alkylene," as used herein, pertains to a bidentate moiety obtained by removing two hydrogen atoms, either both from the same carbon atom, or one from each of two different carbon atoms, of a hydrocarbon compound having from 2 to 10 carbon atoms, which may be aliphatic or alicyclic, or a combination thereof, and which may be saturated, partially unsaturated, or fully unsaturated. The prefix (i.e., "$C_{2-10}$") denotes the number of carbon atoms in the moiety.

In one embodiment, the alkylene group is unsubstituted.

In one embodiment, the two hydrogen atoms are removed from different carbon atoms.

In one embodiment, the two hydrogen atoms are removed from different carbon atoms, and these carbon atoms are not adjacent.

In one embodiment, the alkylene group is $C_{3-10}$alkylene group.

In one embodiment, the alkylene group is $C_{4-10}$alkylene group.

In one embodiment, the alkylene group is $C_{2-8}$alkylene group.

In one embodiment, the alkylene group is $C_{3-8}$alkylene group.

In one embodiment, the alkylene group is $C_{4-8}$alkylene group.

In one embodiment, the alkylene group is $C_{2-7}$alkylene group.

In one embodiment, the alkylene group is $C_{3-7}$alkylene group.

In one embodiment, the alkylene group is $C_{4-7}$alkylene group.

In one embodiment, the alkylene group is $C_{2-6}$alkylene group.

In one embodiment, the alkylene group is $C_{3-6}$alkylene group.

In one embodiment, the alkylene group is $C_{4-6}$alkylene group.

In one embodiment, the alkylene group is $C_3$alkylene group.

In one embodiment, the alkylene group is $C_4$alkylene group.

In one embodiment, the alkylene group is $C_5$alkylene group.

In one embodiment, the alkylene group is $C_6$alkylene group.

In one embodiment, the alkylene group is an aliphatic group.

In one embodiment, the alkylene group is a branched group.

In one embodiment, the alkylene group is a linear group.

In one embodiment, the alkylene group is a partially unsaturated aliphatic group.

In one embodiment, the alkylene group is a fully saturated aliphatic group.

In one embodiment, the alkylene group is a partially unsaturated branched group. Examples of such groups include, but are not limited to, the following:

—C(Me)=CH—, —CH=C(Me)—, —C(Me)=C(Me)—,
—C(Et)=CH—, —CH=C(Et)-, —C(Et)=C(Et)-,
—C(Me)=CH—CH$_2$—, —CH=C(Me)-CH$_2$—,
—CH=CH—CH(Me)—,
—C(Et)=CH—CH$_2$—, —CH=C(Et)-CH$_2$—,
—CH=CH—CH(Et)-,
—C(Me)=CH—CH$_2$CH$_2$—, —CH=C(Me)-CH$_2$CH$_2$—,
—CH=CH—CH(Me)CH$_2$—,
—C(Et)=CH—CH$_2$CH$_2$—, —CH=C(Et)-CH$_2$CH$_2$—, and
—CH=CH—CH(Et)CH$_2$—.

In one embodiment, the alkylene group is a fully saturated branched group.

Examples of such groups include, but are not limited to, the following:

—CH(Me)—, —CH(Et)-,
—CH(Me)CH$_2$—, —CH(Et)CH$_2$—, —CH$_2$CH(Me)—,
—CH$_2$CH(Et)-,
—CH(Me)CH$_2$CH$_2$—, —CH$_2$CH(Me)CH$_2$—,
—CH$_2$CH$_2$CH(Me)—,
—CH(Et)CH$_2$CH$_2$—, —CH$_2$CH(Et)CH$_2$—, —CH$_2$CH$_2$CH(Et)-,
—CH(Me)CH$_2$CH$_2$CH$_2$—, —CH$_2$CH(Me)CH$_2$CH$_2$—,
—CH(Et)CH$_2$CH$_2$CH$_2$—, and —CH$_2$CH(Et)CH$_2$CH$_2$—.

In one embodiment, the alkylene group is a partially unsaturated linear group.

Examples of such groups include, but are not limited to, the following:

—CH=CH— (vinylene),
—CH=CH—CH$_2$—, —CH$_2$—CH=CH—,
—CH=CH—CH$_2$—CH$_2$—, —CH$_2$—CH—CH=CH—,
—CH=CH—CH=CH—,
—CH=CH—CH$_2$—CH$_2$—CH$_2$—, —CH=CH—CH=CH—CH$_2$—, —CH=CH—CH$_2$—CH=CH—,
—CH=CH—CH=CH—CH$_2$—CH$_2$—, and —CH=CH—CH$_2$—CH$_2$—CH=CH—.

In one embodiment, the alkylene group is a fully saturated linear group.

Examples of such groups include, but are not limited to, groups of the formula —(CH$_2$)$_n$— where n is an integer from 2 to 10, for example, —(CH$_2$)$_2$— (ethylene), —(CH$_2$)$_3$— (propylene), —(CH$_2$)$_4$— (butylene), —(CH$_2$)$_5$— (pentylene), —(CH$_2$)$_6$-(hexylene), —(CH$_2$)$_7$— (heptylene), —(CH$_2$)$_8$— (octylene), —(CH$_2$)$_9$— (nonylene), and —(CH$_2$)$_{10}$— (decylene).

In one embodiment, the alkylene group is —(CH$_2$)$_n$— where n is an integer from 3 to 10.

In one embodiment, the alkylene group is —(CH$_2$)$_n$— where n is an integer from 4 to 10.

In one embodiment, the alkylene group is —(CH$_2$)$_n$— where n is an integer from 2 to 8.

In one embodiment, the alkylene group is —(CH$_2$)$_n$— where n is an integer from 3 to 8.

In one embodiment, the alkylene group is —(CH$_2$)$_n$— where n is an integer from 4 to 8.

In one embodiment, the alkylene group is —(CH$_2$)$_n$— where n is an integer from 2 to 7.

In one embodiment, the alkylene group is —(CH$_2$)$_n$— where n is an integer from 3 to 7.

In one embodiment, the alkylene group is —(CH$_2$)$_n$— where n is an integer from 4 to 7.

In one embodiment, the alkylene group is —(CH$_2$)$_n$— where n is an integer from 2 to 6.

In one embodiment, the alkylene group is —(CH$_2$)$_n$— where n is an integer from 3 to 6.

In one embodiment, the alkylene group is —(CH$_2$)$_n$— where n is an integer from 4 to 6.

In one embodiment, the alkylene group is —(CH$_2$)$_3$—.
In one embodiment, the alkylene group is —(CH$_2$)$_4$—.
In one embodiment, the alkylene group is —(CH$_2$)$_5$—.
In one embodiment, the alkylene group is —(CH$_2$)$_6$—.

In one especially preferred embodiment, the alkylene group is —(CH$_2$)$_4$—:

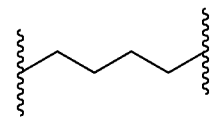

In one embodiment, the alkylene group is substituted, for example, with one or more substituents selected from: halogen, hydroxy, ether (e.g., $C_{1-7}$alkoxy), amino, and amido.

In one embodiment, the alkylene group is substituted, for example, with one or more substituents selected from: —F, —Cl, —Br, and —I.

In one embodiment, the alkylene group is substituted, for example, with one or more —F groups.

In one embodiment, the alkylene group is:

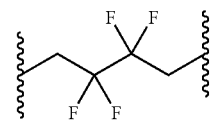

The Hydroxy Groups, —OH, of the Alkane Diol

The hydroxy groups, —OH, of the alkane diol may be primary, secondary, or tertiary.

In one embodiment, the hydroxy groups are primary or secondary.

In one embodiment, at least one of the hydroxy groups is a primary hydroxy group.

In one embodiment, each of the hydroxy groups is a primary hydroxy group.

In one embodiment, the hydroxy groups are not geminal.

In one embodiment, the hydroxy groups are not geminal, and are not vicinal.

Some Preferred Alkane Diols

In one embodiment, the alkane diol has the formula HO—(CH$_2$)$_n$—OH, where n is an integer from 2 to 10.

| | | |
|---|---|---|
| HO—(CH$_2$)$_2$—OH | HO~~~OH | 1,2-ethanediol |
| HO—(CH$_2$)$_3$—OH | HO~~~OH | 1,3-propanediol |
| HO—(CH$_2$)$_4$—OH | HO~~~OH | 1,4-butanediol |
| HO—(CH$_2$)$_5$—OH | HO~~~OH | 1,5-pentanediol |
| HO—(CH$_2$)$_6$—OH | HO~~~OH | 1,6-hexanediol |
| HO—(CH$_2$)$_7$—OH | HO~~~OH | 1,7-heptanediol |
| HO—(CH$_2$)$_8$—OH | HO~~~OH | 1,8-octanediol |
| HO—(CH$_2$)$_9$—OH | HO~~~OH | 1,9-nonanediol |
| HO—(CH$_2$)$_{10}$—OH | HO~~~OH | 1,10-decanediol |

In one embodiment, the alkane diol is 1,3-propanediol, 1,4-butanediol, 1,5-pentanediol, or 1,6-hexanediol.

In one embodiment, the alkane diol is 1,4-butanediol, 1,5-pentanediol, or 1,6-hexanediol.

In one embodiment, the alkane diol is 1,4-butanediol or 1,6-hexanediol.

In one especially preferred embodiment, the alkane diol is 1,4-butanediol:

Hydroxy Protecting Groups

Without wishing to be bound by any particular theory, it is believed that the hydroxy protecting group (or, if there are two such groups, one of them, or each of them) additionally conveys one or more advantageous properties (e.g., solubility, lipophilicity, targeting) to the resulting compound.

For example, the compound is preferably sufficiently soluble in the relevant media (e.g., water, culture media, in vivo) so that, for example, its beneficial therapeutic properties may be realised. Thus, in one embodiment, the hydroxy protecting group (or, if there are two such groups, one of them, or each of them) is selected so that the resulting compound has acceptable solubility properties.

Similarly, the compound is preferably readily able to cross cell membranes, and more specifically, the membranes of cells for which treatment is sought. Thus, in one embodiment, the hydroxy protecting group (or, if there are two such groups, one of them, or each of them) is selected to be, or to comprise, a hydrophobic group, so that the resulting compound is better able to able to cross cell membranes.

Also, in one embodiment, the compound is targeted to bone and/or the bone environment. Thus, in one embodiment, the hydroxy protecting group (or, if there are two such groups, one of them, or each of them) is selected to be, or to comprise, a bone-targeting group.

The term "bone-targeting group," as used herein, pertains to a chemical moiety which has an affinity for bone and/or the bone environment, and which, when attached to compound, acts as a targeting moiety, and so aids in the delivery of that compound to the bone and/or bone environment. Examples of such bone-targeting groups include phosphonic acid groups, and salts, esters, and amides thereof, as discussed below.

Esters as Hydroxy Protecting Groups

In one embodiment, the hydroxy protecting group (or, if there are two such groups, one of them, or each of them) is an acyl group (i.e., $R^A$—C(=O)—), and the protected hydroxy group is an ester group (i.e., $R^A$—C(=O)—). More specifically, the hydroxy group is protected as an ester group.

In one embodiment, $R^2$ is not —H, and each of the hydroxy protecting groups are acyl groups ($R^{A1}$—C(=O)— and $R^{A2}$—C(=O)—, respectively), which may be the same or different, and the compound has the following formula (also referred to herein as a "di-ester" of the alkane diol):

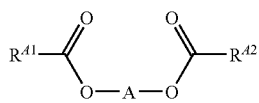

(4)

In one embodiment, $R^2$ is not —H, and $R^{A1}$ and $R^{A2}$ are the same.

In one embodiment, $R^2$ is not —H, and $R^{A1}$ and $R^{A2}$ are different.

In one embodiment, $R^2$ is —H, the hydroxy protecting group is an acyl group (i.e., $R^{A1}$—C(=O)—), and the compound has the following formula (also referred to herein as a "mono-ester" of the alkane diol):

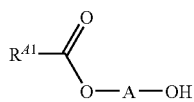

(5)

Acyl Groups, $R^{A1}$—C(=O)— and $R^{A2}$—C(=O)—

In one embodiment, $R^{A1}$ is independently a $C_{1-7}$alkyl group, a $C_{3-20}$heterocyclyl group, or a $C_{5-20}$aryl group, and is optionally substituted; and, $R^{A2}$, if present, is independently, a $C_{1-7}$alkyl group, a $C_{3-20}$heterocyclyl group, or a $C_{5-20}$aryl group, and is optionally substituted.

In one especially preferred embodiment, $R^{A1}$ is independently a $C_{3-20}$heterocyclyl group, or a $C_{5-20}$aryl group, and is optionally substituted In one especially preferred embodiment, $R^{A1}$ is independently an optionally substituted $C_{5-20}$aryl group, as described below.

As discussed above, one or both of the moieties $R^{A1}$ and $R^{A2}$ may be selected so that the resulting compound (a) has improved solubility, (b) is better able to cross cell membranes, (c) is, or comprises, a bone-targeting moiety; or a combination thereof $R^{A1}$ as Optionally Substituted Aryl In one embodiment, $R^{A1}$ (and optionally also $R^{A2}$) is independently an optionally substituted $C_{5-20}$aryl group.

In one embodiment, $R^{A1}$ (and optionally also $R^{A2}$) is independently an optionally substituted phenyl, naphthyl, pyridyl, furanyl, thiofuranyl, indolyl, pyrrolyl, imidazolyl, naphthyl, quinolinyl, benzimidazolyl, benzothiofuranyl, fluorenyl, acridinyl, or carbazolyl.

In one embodiment, $R^{A1}$ (and optionally also $R^{A2}$) is independently an optionally substituted $C_{5-6}$aryl group.

In one embodiment, $R^{A1}$ (and optionally also $R^{A2}$) is independently an optionally substituted phenyl, pyridyl, furanyl, thiofuranyl, indolyl, pyrrolyl, or imidazolyl.

$R^{A1}$ as Optionally Substituted Phenyl

In one embodiment, $R^{A1}$ (and optionally also $R^{A2}$) is independently an optionally substituted phenyl group of the following formula:

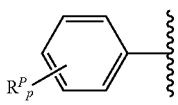

wherein each $R^P$ is independently a phenyl substituent, and p is an integer from 0 to 5.

In one embodiment, p is an integer from 0 to 4.
In one embodiment, p is an integer from 0 to 3.
In one embodiment, p is an integer from 0 to 2.
In one embodiment, p is 0 or 1.

$R^{A1}$ as Optionally Substituted Biphenyl

In one embodiment, $R^{A1}$ (and optionally also $R^{A2}$) is independently an optionally substituted biphenyl group of the following formula:

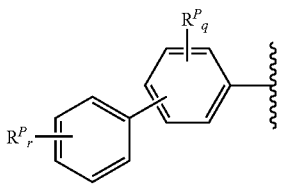

wherein each $R^P$ is independently a phenyl substituent, q is an integer from 0 to 4, and r is an integer from 0 to 5.

In one embodiment, q is an integer from 0 to 3.
In one embodiment, q is an integer from 0 to 2.
In one embodiment, q is 0 or 1.
In one embodiment, q is 0.

In one embodiment, r is an integer from 0 to 4.
In one embodiment, r is an integer from 0 to 3.
In one embodiment, r is an integer from 0 to 2.
In one embodiment, r is 0 or 1.
In one embodiment, r is 0.

In one embodiment, q is 0, and $R^{A1}$ (and optionally also $R^{A2}$) is an optionally substituted biphenyl group of the following formula:

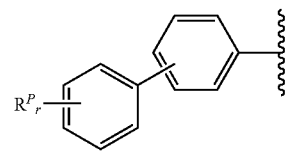

$R^{A1}$ as Optionally Substituted Biphenyl-4-yl

In one embodiment, $R^{A1}$ (and optionally also $R^{A2}$) is an optionally substituted biphenyl-4-yl group of the following formula:

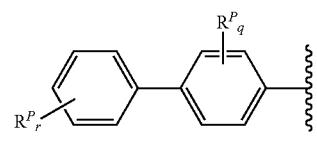

In one embodiment, $R^{A1}$ (and optionally also $R^{A2}$) is an optionally substituted biphenyl-4-yl group of the following formula:

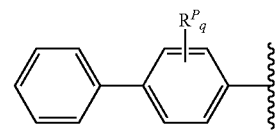

In one embodiment, $R^{A1}$ (and optionally also $R^{A2}$) is an optionally substituted biphenyl-4-yl group of the following formula:

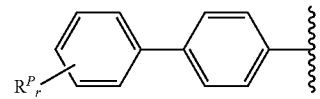

$R^{A1}$ as 4'-Substituted Biphenyl-4-yl

In one embodiment, $R^{A1}$ (and optionally also $R^{A2}$) is a substituted biphenyl-4-yl group of the following formula:

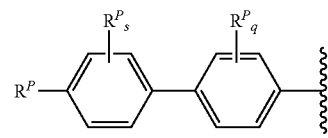

wherein s is an integer from 0 to 4.
In one embodiment, s is an integer from 0 to 3.
In one embodiment, s is an integer from 0 to 2.
In one embodiment, s is 0 or 1.
In one embodiment, s is 0.

In one embodiment, $R^{A1}$ (and optionally also $R^{A2}$) is a substituted biphenyl-4-yl group of the following formula:

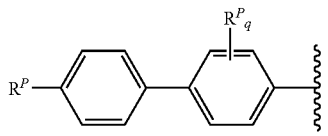

In one embodiment, $R^{A1}$ (and optionally also $R^{A2}$) is a substituted biphenyl-4-yl group of the following formula:

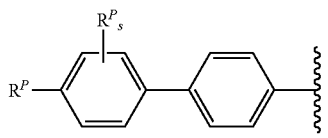

In one embodiment, $R^{A1}$ (and optionally also $R^{A2}$) is a substituted biphenyl-4-yl group of the following formula:

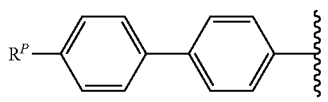

$R^{A1}$ as 3'-Substituted Biphenyl-4-yl

In one embodiment, $R^{A1}$ (and optionally also $R^{A2}$) is a substituted biphenyl-4-yl group of the following formula:

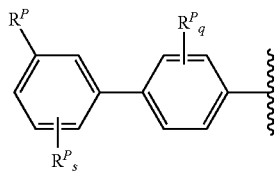

In one embodiment, $R^{A1}$ (and optionally also $R^{A2}$) is a substituted biphenyl-4-yl group of the following formula:

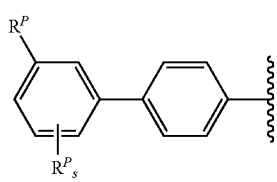

In one embodiment, $R^{A1}$ (and optionally also $R^{A2}$) is a substituted biphenyl-4-yl group of the following formula:

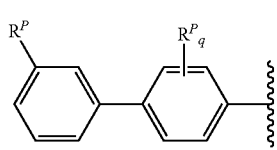

In one embodiment, $R^{A1}$ (and optionally also $R^{A2}$) is a substituted biphenyl-4-yl group of the following formula:

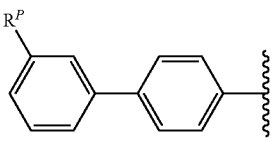

$R^{A1}$ as 3',4'-Disubstituted Biphenyl-4-yl

In one embodiment, $R^{A1}$ (and optionally also $R^{A2}$) is a substituted biphenyl-4-yl group of the following formula:

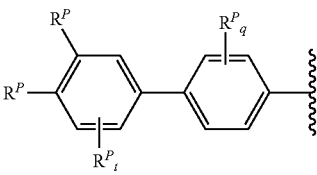

wherein t is an integer from 0 to 3.

In one embodiment, t is an integer from 0 to 2.

In one embodiment, t is 0 or 1.

In one embodiment, t is 0.

In one embodiment, $R^{A1}$ (and optionally also $R^{A2}$) is a substituted biphenyl-4-yl group of the following formula:

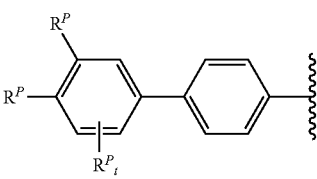

In one embodiment, $R^{A1}$ (and optionally also $R^{A2}$) is a substituted biphenyl-4-yl group of the following formula:

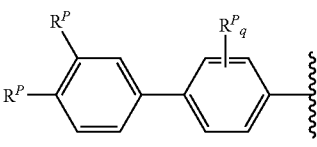

In one embodiment, $R^{A1}$ (and optionally also $R^{A2}$) is a substituted biphenyl-4-yl group of the following formula:

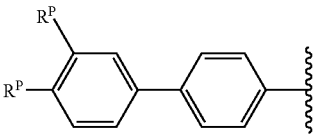

$R^{A1}$ as 2'-Substituted Biphenyl-4-yl

In one embodiment, $R^{A1}$ (and optionally also $R^{A2}$) is a substituted biphenyl-4-yl group of the following formula:

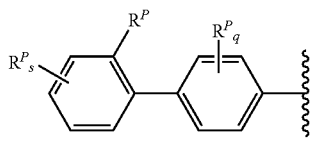

In one embodiment, $R^{A1}$ (and optionally also $R^{A2}$) is a substituted biphenyl-4-yl group of the following formula:

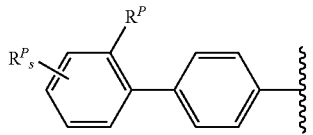

In one embodiment, $R^{A1}$ (and optionally also $R^{A2}$) is a substituted biphenyl-4-yl group of the following formula:

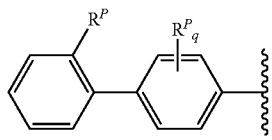

In one embodiment, $R^{A1}$ (and optionally also $R^{A2}$) is a substituted biphenyl-4-yl group of the following formula:

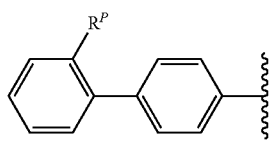

$R^{A1}$ as 2',4'-Disubstituted Biphenyl-4-yl

In one embodiment, $R^{A1}$ (and optionally also $R^{A2}$) is a substituted biphenyl-4-yl group of the following formula:

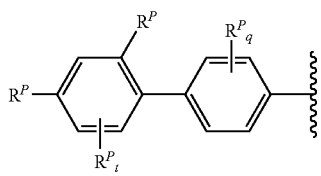

In one embodiment, $R^{A1}$ (and optionally also $R^{A2}$) is a substituted biphenyl-4-yl group of the following formula:

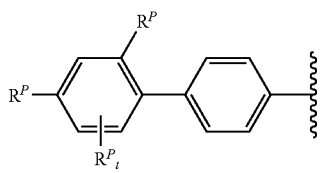

In one embodiment, $R^{A1}$ (and optionally also $R^{A2}$) is a substituted biphenyl-4-yl group of the following formula:

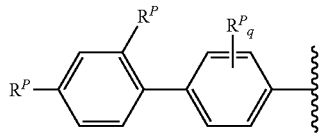

In one embodiment, $R^{A1}$ (and optionally also $R^{A2}$) is a substituted biphenyl-4-yl group of the following formula:

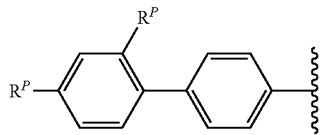

$R^{A1}$ as Unsubstituted Biphenyl-4-yl

In one embodiment, $R^{A1}$ (and optionally also $R^{A2}$) is an unsubstituted biphenyl-4-yl group of the following formula:

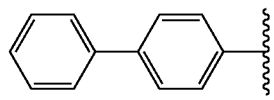

Some examples of preferred alkane diol derivatives, wherein $R^{A2}$ is —H, are shown below.

(6)

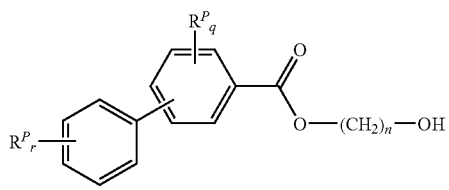

(7)

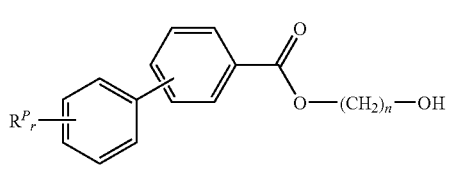

(8)

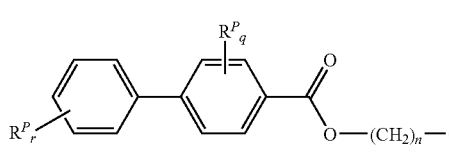

(9)

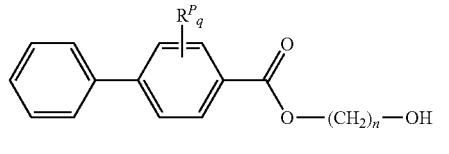

(10)

-continued
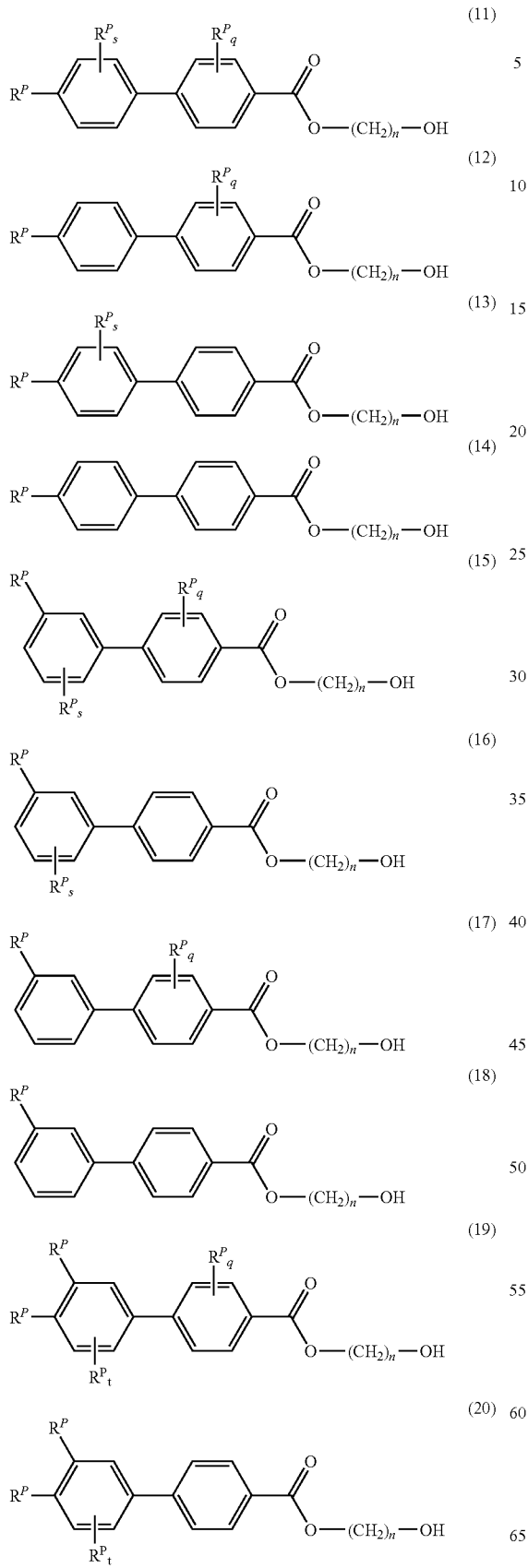
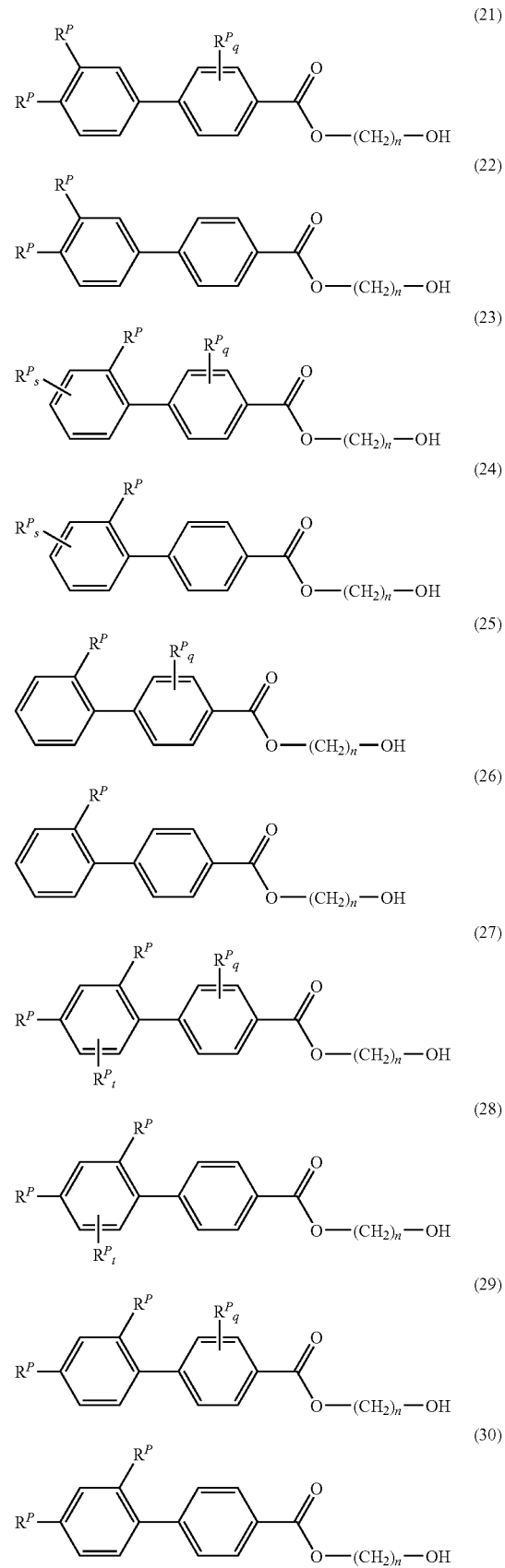

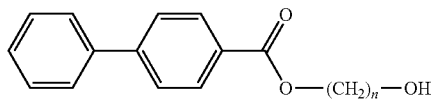
(31)
Some examples of preferred alkane diol derivatives, wherein $R^{A2}$ is —H and the alkane diol is 1,4-butanediol, are shown below.
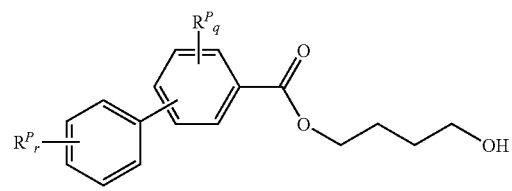
(32)
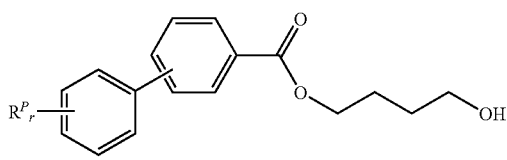
(33)
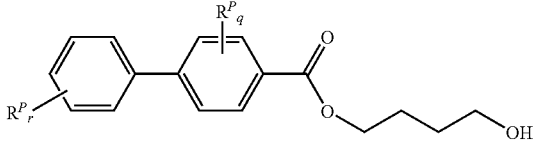
(34)
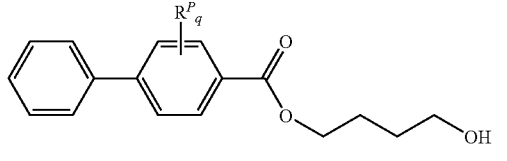
(35)
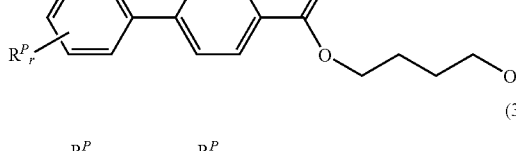
(36)
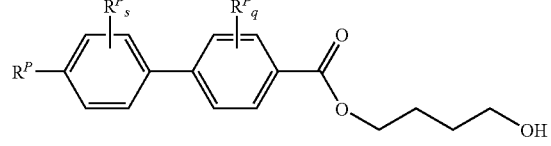
(37)
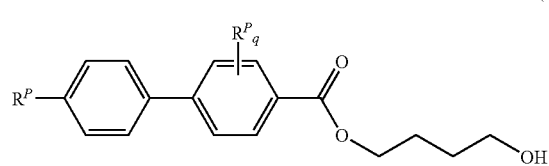
(38)
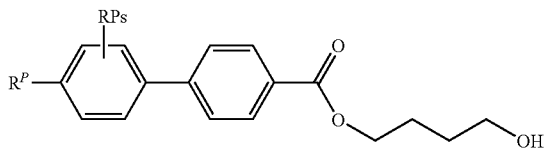
(39)
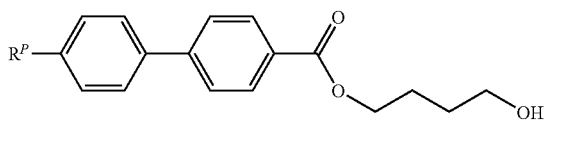
(40)
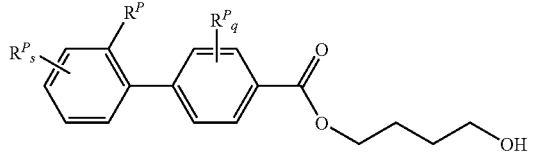
(41)
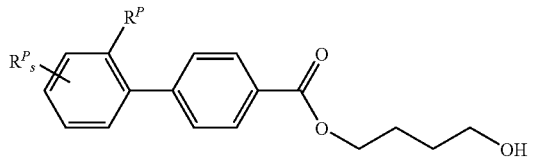
(42)
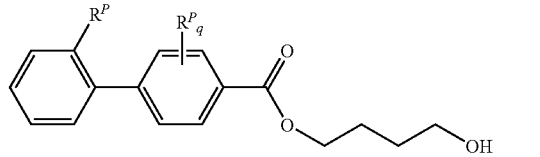
(43)
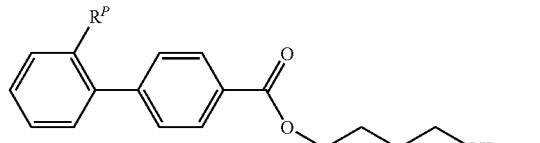
(44)
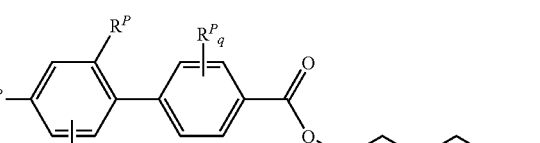
(45)
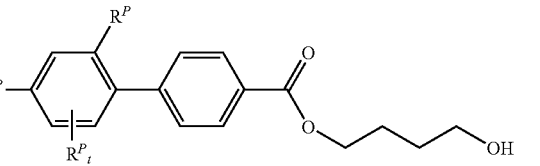
(46)

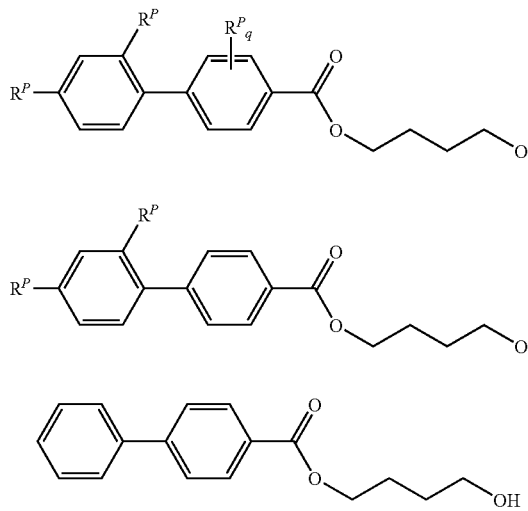

Phenyl Substituents, $R^P$

Examples of phenyl substituents, $R^P$, include, but are not limited to, those described below under the heading "substituents."

Examples of some preferred phenyl substituents, $R^P$, include, but are not limited to, the following:

$C_{1-7}$alkyl (optionally substituted) (including, e.g., unsubstituted $C_{1-7}$alkyl, $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl);
$C_{3-20}$heterocyclyl (optionally substituted);
$C_{5-20}$aryl group (optionally substituted) (including, e.g., $C_{5-20}$carboaryl,
$C_{5-20}$heteroaryl, $C_{1-7}$alkyl-$C_{5-20}$aryl and $C_{5-20}$haloaryl);
halo;
hydroxy;
ether (e.g., $C_{1-7}$alkoxy);
acyl (e.g., $C_{1-7}$alkylacyl, $C_{5-20}$arylacyl);
carboxy;
ester;
acyloxy;
oxycarboyloxy;
amido;
acylamido;
thioamido;
tetrazolyl;
amino;
nitro;
cyano;
sulfhydryl;
thioether (e.g., $C_{1-7}$alkylthio);
sulfonic acid;
sulfonate; and
sulfonamido.

In one embodiment, the phenyl substituents, $R^P$, are selected from:
$C_{1-7}$alkyl (optionally substituted);
$C_{3-20}$heterocyclyl (optionally substituted);
$C_{5-20}$aryl group (optionally substituted);
halo;
hydroxy;
ether (e.g., $C_{1-7}$alkoxy);
acyl (e.g., $C_{1-7}$alkylacyl, $C_{5-20}$arylacyl);
carboxy;
ester;
acyloxy;
amido;
acylamido;
amino;
nitro;
cyano; and,
sulfonate.

In one embodiment, the phenyl substituents, $R^P$, are selected from:
-Me, -Et, -iPr, -nPr, -tBu;
-Ph;
—F, —Cl, —Br, —I;
—OH;
—OMe, —OEt, —O(iPr), —O(nPr), —O(tBu), —OPh, —OBn;
—C(=O)OH;
—C(=O)OMe, —C(=O)OEt, —C(=O)O(tBu), —C(=O)OPh;
—OC(C=O)Me, —OC(C=O)Et, —OC(C=O)(tBu), —OC(C=O)Ph;
—OC(C=O)OMe, —OC(C=O)OEt, —OC(C=O)O(tBu), —OC(C=O)OPh;
—C(=O)NH$_2$, —C(=O)NHMe, —C(=O)NMe$_2$, —C(=O)NHPh;
—NHC(=O)Me, —NHC(=O)Et, —NHC(=O)Ph;
—NH$_2$, —NHMe, —NMe$_2$, —NHEt, —NEt$_2$;
—NO$_2$;
—CN; and,
—S(=O)$_2$OMe, —S(=O)$_2$OEt, —S(=O)$_2$OPh.

In one embodiment, the phenyl substituents, $R^P$, are selected from:
-Me, —F, —Cl, —Br, -I, —OH, —OMe, —NH$_2$, —NMe$_2$, —NO$_2$, and —CN.

In one embodiment, the phenyl substituents, $R^P$, are selected from:
-Me, —F, —Cl, —OH, —OMe, —NH$_2$, —NMe$_2$, —NO$_2$, and —CN.

In one embodiment, the phenyl substituents, $R^P$, are selected from:
—F, —Cl, —Br, -I, —NO$_2$, and —OH.

In one embodiment, the phenyl substituents, $R^P$, are selected from:
—F, —Cl, —Br, and —I, —NO$_2$.

In one embodiment, the phenyl substituents, $R^P$, are selected from:
—F, —Cl, —Br, —I.

In one embodiment, the phenyl substituents, $R^P$, are selected from:
—F and —Br.

In one embodiment, the phenyl substituents, $R^P$, are —F.

Examples of Some Preferred Fluoro-Substituted Phenyl $R^{41}$ Groups

Some examples of substituted phenyl groups, suitable as $R^{41}$ (and optionally also $R^{42}$) include the following:

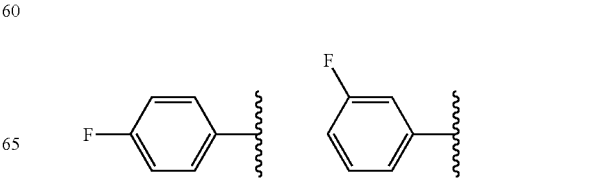

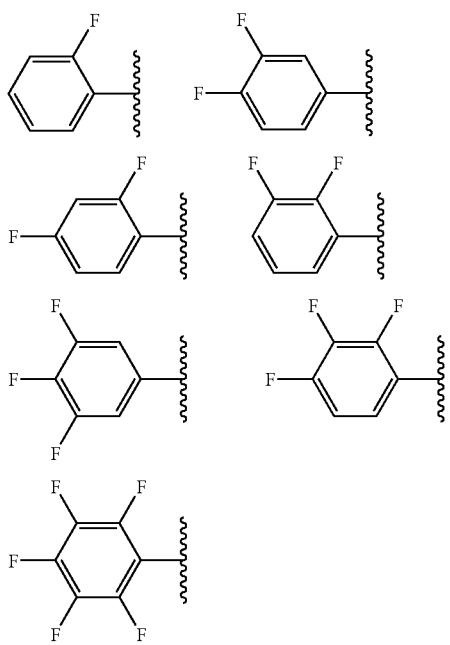

One especially preferred substituted phenyl group, suitable as $R^{A1}$ (and optionally also $R^{A2}$) is:

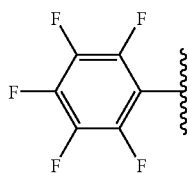

Examples of Some Preferred Substituted Biphenyl-4-yl $R^{A1}$ Groups

Some examples of substituted biphenyl-4-yl groups, suitable as $R^{A1}$ (and optionally also $R^{A2}$) include the following:

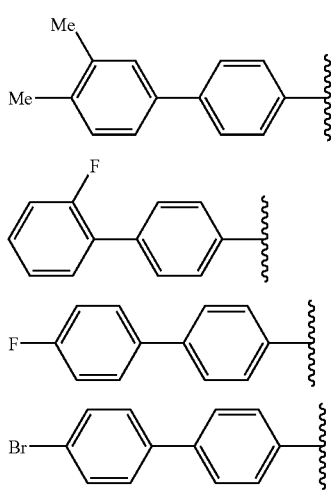

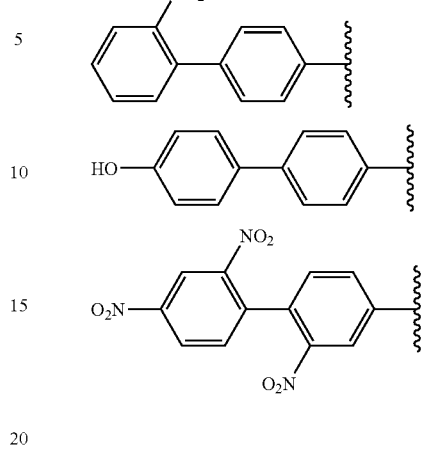

Examples of Some Preferred Fluoro-Substituted Biphenyl-4-yl $R^{A1}$ Groups

Some examples of substituted biphenyl-4-yl groups, suitable as $R^{A1}$ (and optionally also $R^{A2}$) include the following:

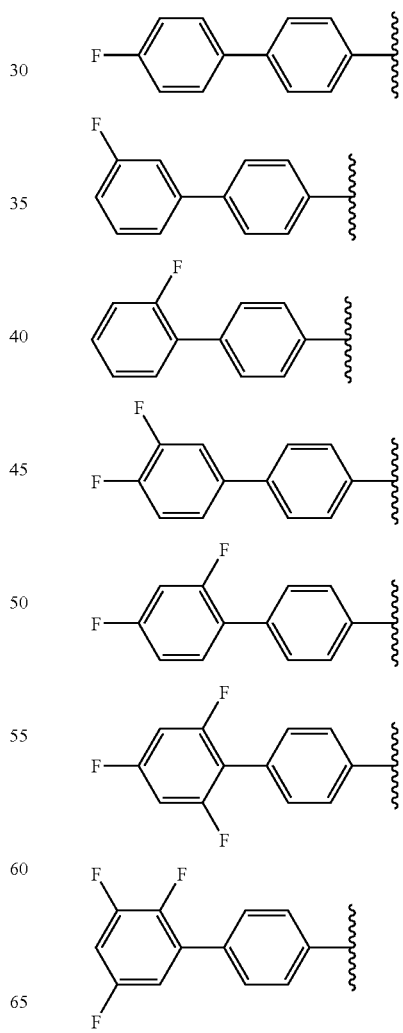

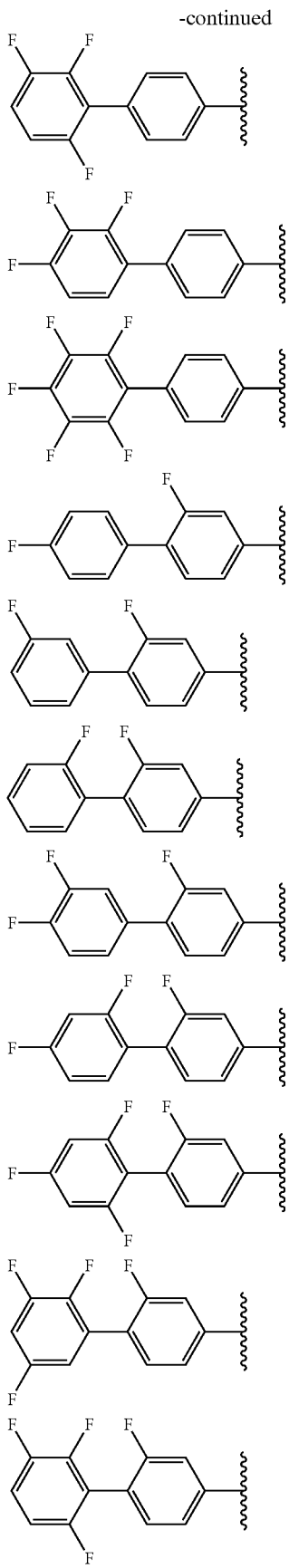

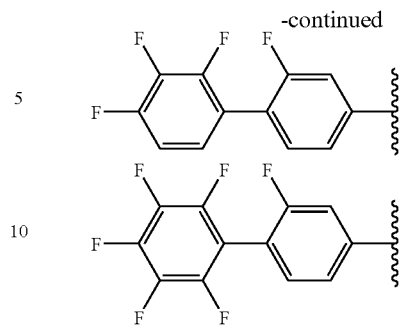

R$^A$ as Optionally Substituted Aryl-Alkyl

In one embodiment, R$^{A1}$ alone, R$^{A2}$ alone, or each of R$^{A1}$ and R$^{A2}$, is an optionally substituted C$_{5-20}$aryl-C$_{1-17}$alkyl group.

In one embodiment, R$^{A1}$ alone, R$^{A2}$ alone, or each of R$^{A1}$ and R$^{A2}$, is an optionally substituted C$_{5-6}$aryl-C$_{1-7}$alkyl group.

In one embodiment, R$^{A1}$ alone, R$^{A2}$ alone, or each of R$^{A1}$ and R$^{A2}$, is an optionally substituted C$_{5-6}$aryl-C$_{1-3}$alkyl group.

Examples of such groups include, but are not limited to, the following:

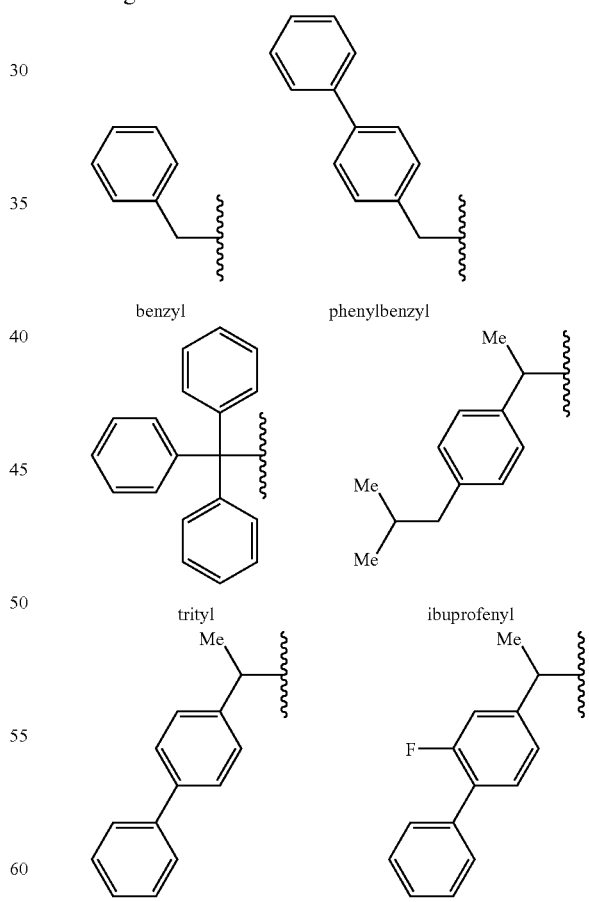

R$^A$ Comprising Optionally Substituted Cycloalkyl

In one embodiment, R$^{A1}$ alone, R$^{A2}$ alone, or each of R$^{A1}$ and R$^{A2}$, is or comprises an optionally substituted C$_{3-7}$cycloalkyl group.

In one embodiment, $R^{A1}$ alone, $R^{A2}$ alone, or each of $R^{A1}$ and $R^{A2}$, is an optionally substituted $C_{3-7}$cycloalkyl group or optionally substituted $C_{3-7}$cycloalkyl-$C_{1-7}$alkyl group.

Examples of such groups include, but are not limited to, the following:

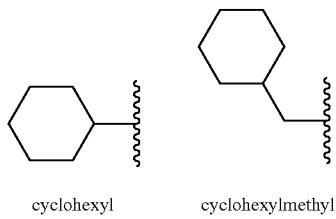

cyclohexyl        cyclohexylmethyl $R^{A2}$ Comprising a Phosphonic Acid Group: Bone Targeting Moieties In one embodiment, $R^{A2}$ independently is, or comprises, a phosphonic acid group.

In one embodiment, $R^{A2}$ independently is, or comprises, a phosphonic acid group selected from phosphonic acid, and salts (e.g. phosphonates) and esters (e.g., phosphonate esters) thereof.

Without wishing to be bound by any particular theory, it is believed that such groups act as bone targeting moieties, and improve delivery of the compound to the bone envinronment.

Examples of such substituents are shown below. For the phosphonate esters, the groups $R^1$ and $R^2$ are independently $C_{1-7}$alkyl, $C_{3-20}$heterocyclyl, or $C_{5-20}$aryl, preferably $C_{1-7}$alkyl.

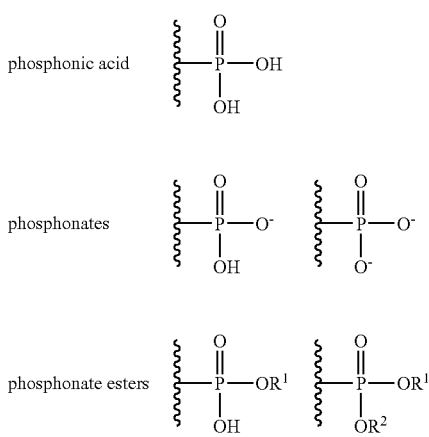

Where the group is a phosphonate bearing a charge of (−1) or (−2), it will be associated with a suitable number of cation or cations of suitable charge. Examples of suitable cations are discussed below.

Thus, in one embodiment, $R^{A2}$ is, or comprises, a substituted $C_{1-7}$alkyl group derived from a bisphosphonate compound.

Examples of bisphosphonate compounds currently in use for the treatment of osteoporosis, Paget's disease, and cancer associated bone disease include the following:

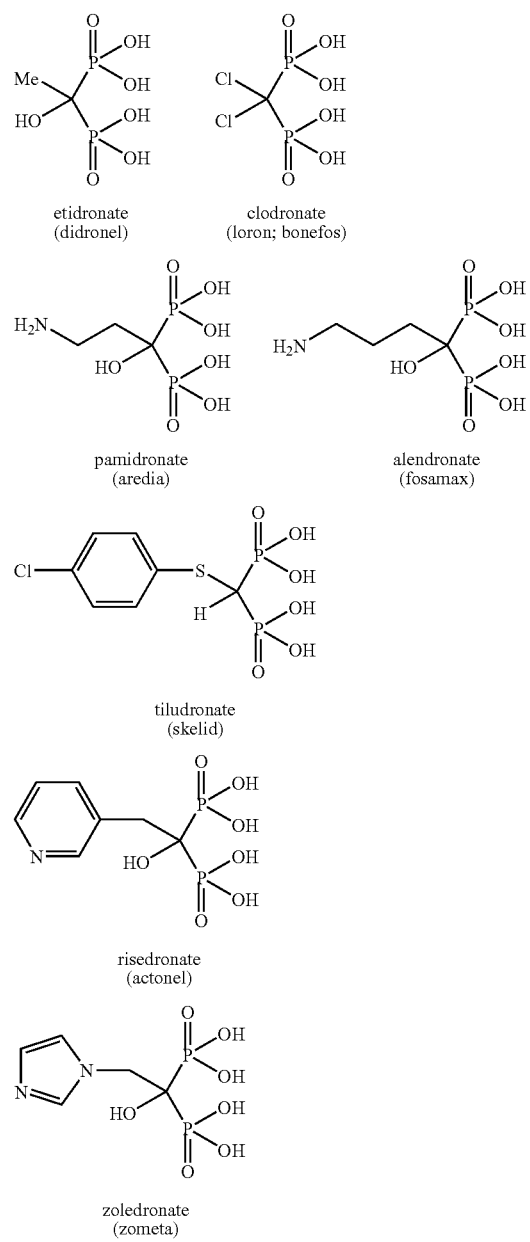

Examples of bisphosphonate compounds currently in development include the following:

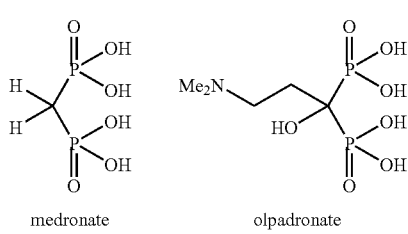

-continued

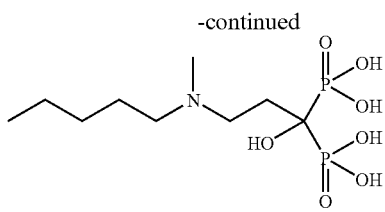
ibandronate

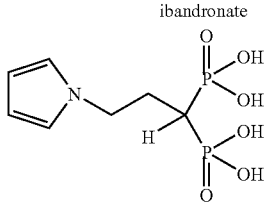
EB-1053

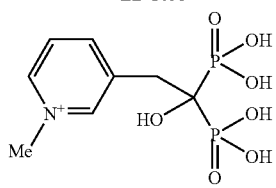
methyl pyridinium analogue

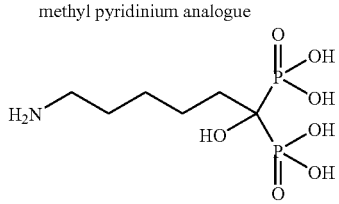
neridronate

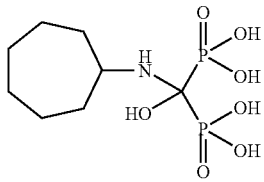
incadronate

In one embodiment, $R^A$ independently is, or comprises, a $C_{1-7}$alkyl group substituted with one or more groups independently selected from phosphonic acid, and salts (e.g. phosphonates) and esters (e.g., phosphonate esters) thereof.

In one embodiment, $R^{A2}$ independently is, or comprises, a $C_{1-7}$alkyl group substituted with one group independently selected from phosphonic acid, and salts (e.g. phosphonates) and esters (e.g., phosphonate esters) thereof.

In one embodiment, $R^{A2}$ independently is, or comprises, a $C_{1-7}$alkyl group substituted with two groups independently selected from phosphonic acid, and salts (e.g. phosphonates) and esters (e.g., phosphonate esters) thereof.

In one embodiment, $R^{A2}$ independently is, or comprises, a $C_{1-7}$alkyl group which is substituted with a bisphosphonic acid group, or a salt or ester thereof.

The $C_{1-7}$alkyl group may optionally be additionally substituted with one or more other groups.

In one embodiment, $R^{A2}$ independently is, or comprises, a $C_{1-7}$alkyl group which comprises a bisphosphonic acid group of the following formula, or a salt or ester thereof:

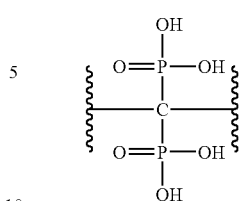

In one embodiment, $R^{A1}$, is independently a group selected from groups of the following formula, or a salt or ester thereof:

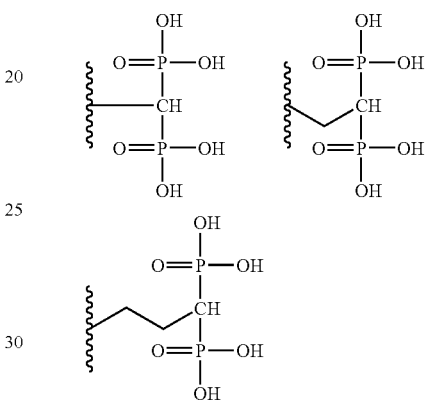

In one embodiment, $R^{A2}$, is independently a group of the following formula, or a salt or ester thereof:

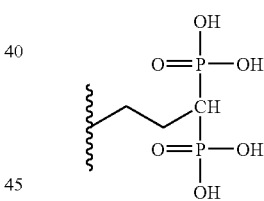

In one embodiment, $R^{A2}$ is independently a group of the following formula, or a salt or ester thereof, wherein $R^{BP}$ is a bisphosphonate substituent, for example, —H, —OH, —Cl, and $C_{1-7}$alkyl (including, e.g., unsubstituted $C_{1-7}$alkyl, $C_{1-7}$haloalkyl, $C_{1-7}$hydroxyalkyl, $C_{1-7}$alkoxyalkyl, $C_{1-7}$carboxyalkyl, $C_{1-7}$aminoalkyl, $C_{5-20}$aryl-$C_{1-7}$alkyl).

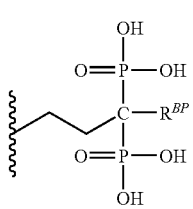

In one embodiment, $R^{A2}$ is independently a group of the following formula, or a salt or ester thereof:

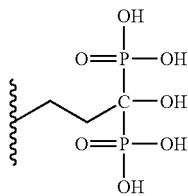

In one embodiment, $R^{A2}$ is independently a group of the following formula, or a salt or ester thereof:

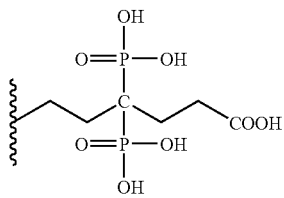

$R^{A2}$ Comprising a $Ca^{2+}$ Binding Group: Bone Targeting Moieties

In one embodiment, $R^{A2}$ independently is or comprises a Ca binding group.

The term "$Ca^{2+}$ binding group," as used herein, pertains to a moiety which binds (e.g., complexes) one or more $Ca^{2+}$ ions. Without wishing to be bound by any particular theory, it is believed that such $Ca^{2+}$ binding groups act as bone targeting moieties, and improve delivery of the compound to the bone envinronment.

Examples of $Ca^{2+}$ binding groups include, but are not limited to, those derived from tetracyclin.

Combination Derivatives of Alkane Diols

In one embodiment, both $R^1$ and $R^2$ are not —H; $R^1$ and $R^2$ are different; and each of $R^1$ and $R^2$ is independently a (non —H) group as described above. Such compounds may be conveniently referred to as "asymmetric" compounds.

In one embodiment, both $R^1$ and $R^2$ are not —H; $R^1$ and $R^2$ are different; $R^1$ is a group of the formula —C(=O)$R^{A1}$, where $R^{A1}$ is an optionally substituted aryl group, as described above; and, $R^2$ is independently a (non —H) group, as described above.

In one embodiment, both $R^1$ and $R^2$ are not —H; $R^1$ and $R^2$ are different; $R^1$ is a group of the formula —C(=O)$R^{A1}$, where $R^{A1}$ is an optionally substituted aryl group, as described above; and, $R^2$ is a group of the formula —C(=O)$R^{A2}$, where $R^{A2}$ is as described above (e.g., a $C_{1-7}$alkyl group, a $C_{3-20}$heterocyclyl group, or a $C_{5-20}$aryl group, and is optionally substituted).

For example, in one embodiment, $R^{A1}$ is an optionally substituted aryl and $R^{A2}$ is a $C_{1-7}$alkyl group. An example of such an embodiment is:

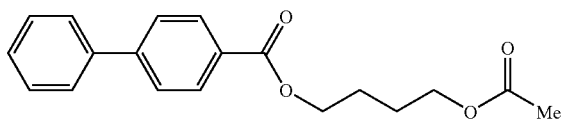

In one embodiment, both $R^1$ and $R^2$ are not —H; $R^1$ and $R^2$ are different; $R^1$ is a group of the formula —C(=O)$R^{A1}$, where $R^{A1}$ is an optionally substituted aryl group, as described above; and, $R^2$ is a group of the formula —C(=O) $R^{A2}$, where $R^{A2}$ comprises a bone targeting moiety, for example, phosphonic acid group or a $Ca^{2+}$ binding group, as described above.

For example, in one embodiment, the compound has the following formula, or is a salt or ester thereof:

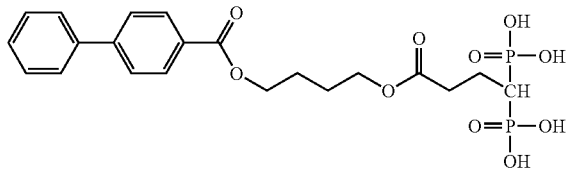

Other Derivatives of Alkane Diols

In one embodiment, the compounds are as described herein, except that the group —O$R^2$ is replaced with another group.

Thus, one aspect of the present invention pertains to compounds which have the following formula:

(50)

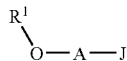

wherein $R^1$ and A are as described above, and J is independently selected from hydrogen; halogen; nitrooxy (—ONO$_2$); ether groups (e.g., $C_{1-17}$alkoxy); groups which are, or comprise, a phosphonic acid group (as described above); and groups which are, or comprise, a $Ca^{2+}$ binding group (as described above); and pharmaceutically acceptable salts, solvates, amides, esters, ethers, chemically protected forms, or prodrugs thereof.

In one embodiment, the compound has the following formula:

(51)

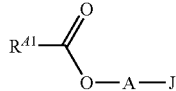

wherein $R^{A1}$, A, and J are as described above.

In one embodiment, J is selected from: hydrogen, halogen, nitrooxy (—ONO$_2$), and $C_{1-7}$alkoxy.

In one embodiment, J is selected from: —H, —F, —Cl, —Br, —I, —ONO$_2$, —OMe, and —OEt.

In one embodiment, J is —H.

In one embodiment, J is selected from: —F, —Cl, —Br, and —I.

In one embodiment, J is —ONO$_2$.

In one embodiment, J is $C_{1-7}$alkoxy.

In one embodiment, J is selected from: —OMe and —OEt.

In one embodiment, J is selected from groups which are, or comprise, a phosphonic acid group (as described above).

In one embodiment, J is selected from groups which are, or comprise, a $Ca^{2+}$ binding group (as described above).

Examples of Specific Embodiments

Some individual embodiments of the present invention include the following compounds.

| | | |
|---|---|---|
| 1 | ABD-0006 4A | 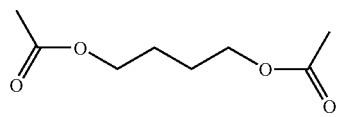 |
| 2 | ABD-0007 4BU | 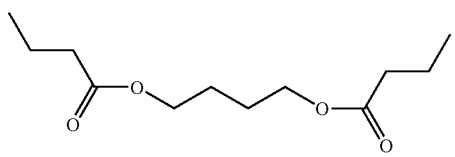 |
| 3 | ABD-0019 4C | 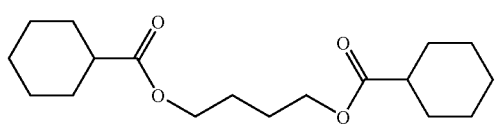 |
| 4 | ABD-0009 4B | 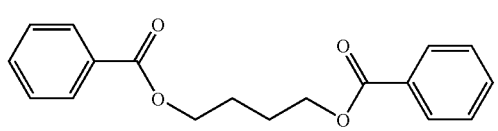 |
| 5 | ABD-0014 4P | 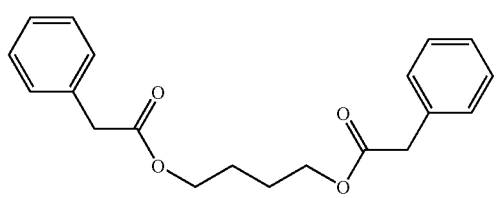 |
| 6 | ABD-0017 6P | 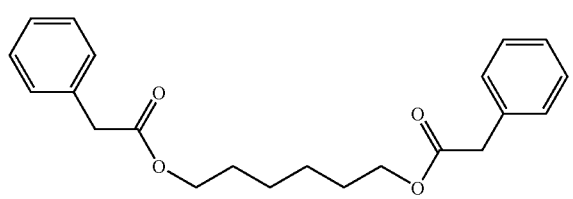 |
| 7 | ABD-0085 10F | 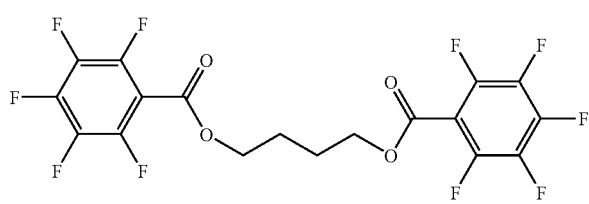 |
| 8 | ABD-0111 D2,4FB | 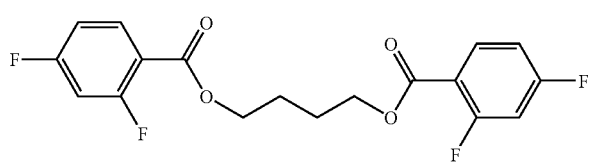 |
| 9 | ABD-0096 DBP-4F | 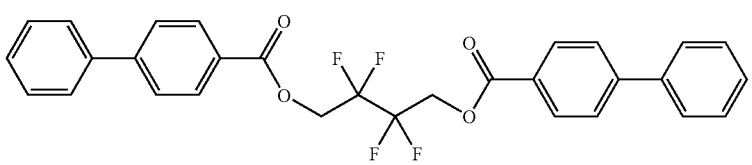 |
| 10 | ABD-0049 4BP-acetate | 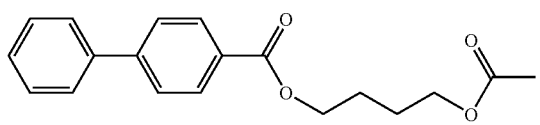 |

-continued
| | | |
|---|---|---|
| 11 | ABD-0008 4MB | 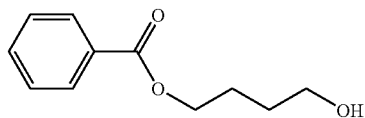 |
| 12 | ABD-0069 4IB | 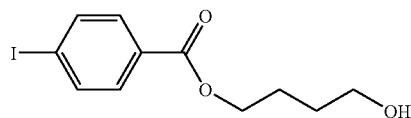 |
| 13 | ABD-0077 4FB | 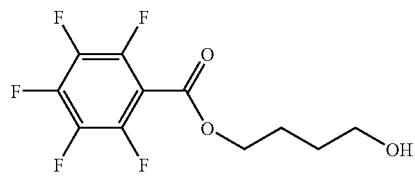 |
| 14 | ABD-0106 2,3,6-FB | 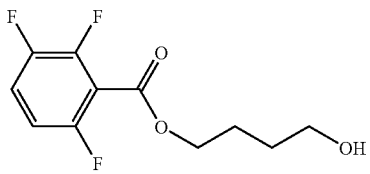 |
| 15 | ABD-0107 3,4-FB | 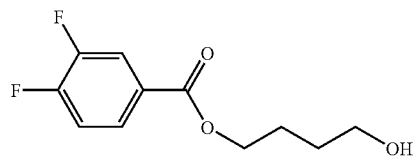 |
| 16 | ABD-0108 2,3,4-FB | 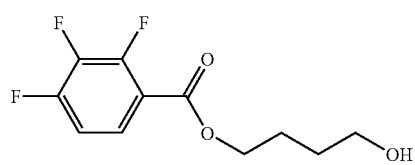 |
| 17 | ABD-0109 2,4,5-FB | 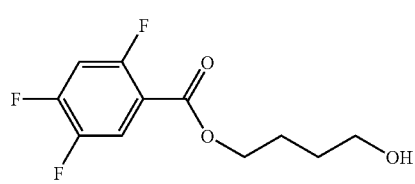 |
| 18 | ABD-0110 2,4-FB | 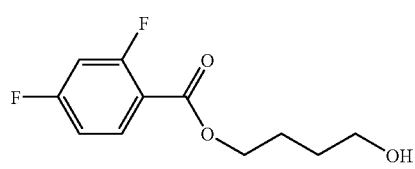 |
| 19 | ABD-0037 3I | 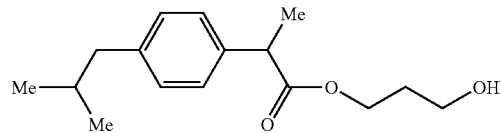 |

-continued
| | | |
|---|---|---|
| 20 | ABD-0036 4I | 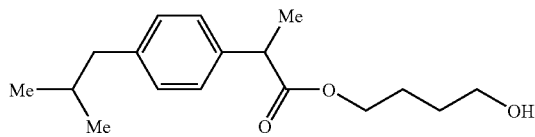 |
| 21 | ABD-0038 5I | 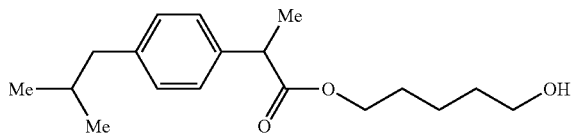 |
| 22 | ABD-0039 6I | 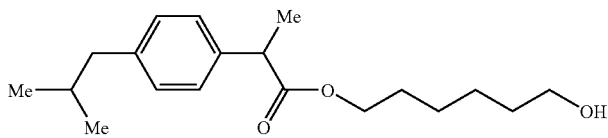 |
| 23 | ABD-0034 4PT | 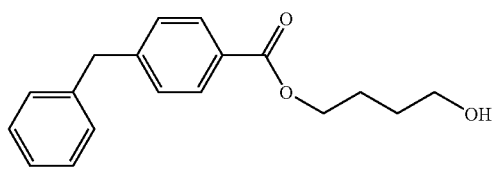 |
| 24 | ABD-0059 4BPX | 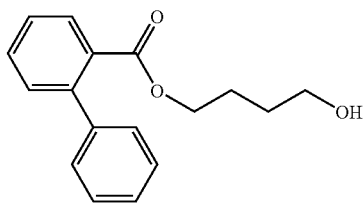 |
| 25 | ABD-0057 3BP | 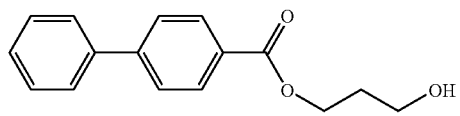 |
| 26 | ABD-0056 4BP | 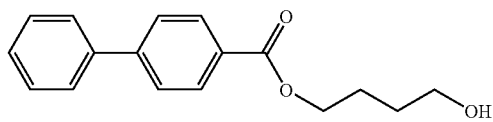 |
| 27 | ABD-0055 5BP | 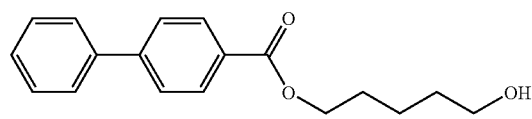 |
| 28 | ABD-0054 6BP | 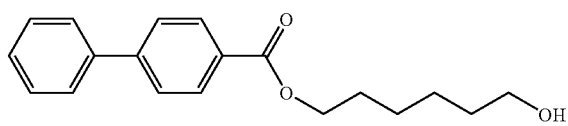 |
| 29 | ABD-0095 BP-4F | 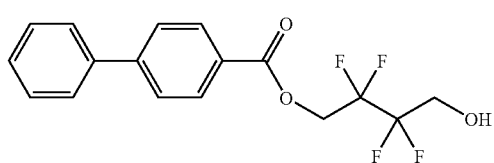 |

-continued
| 30 | ABD-0070 Me4BP | 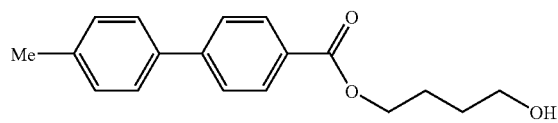 |
| 31 | ABD-0072 HO4BP | 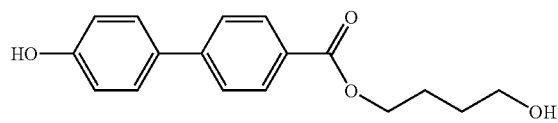 |
| 32 | ABD-0089 Xy4BP | 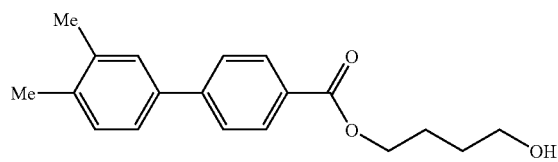 |
| 33 | ABD-0094 Et4BP | 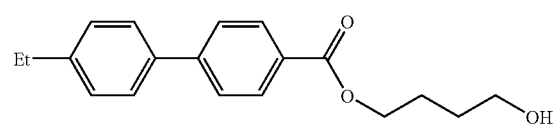 |
| 34 | ABD-0097 4-OMeBP | 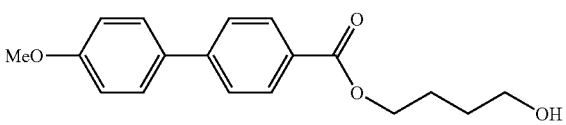 |
| 35 | ABD-0098 2-NO$_2$BP | 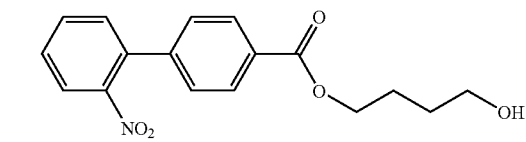 |
| 36 | ABD-0099 2-FBP | 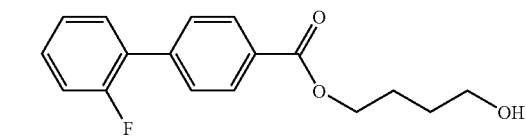 |
| 37 | ABD-0100 4-FBP | 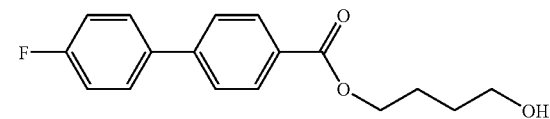 |
| 38 | ABD-0102 4-BrBP | 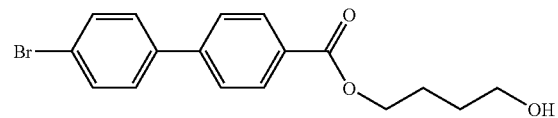 |
| 39 | ABD-0028 4T | 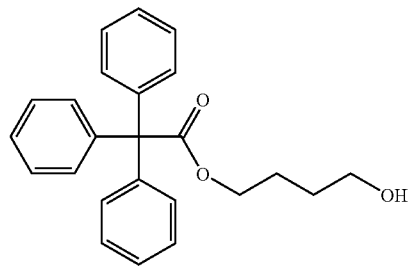 |

-continued
40  ABD-0030
    5T
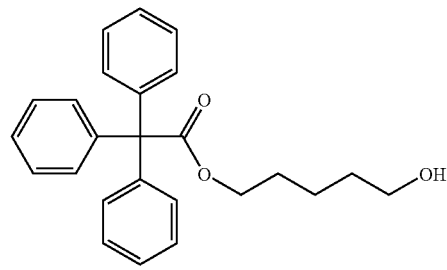
41  ABD-0031
    6T
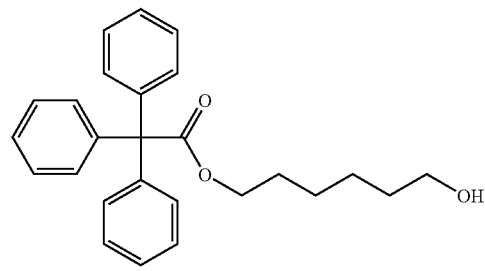
42  ABD-0041
    3BPA
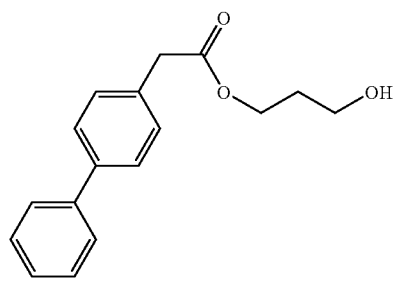
43  ABD-0042
    4BPA
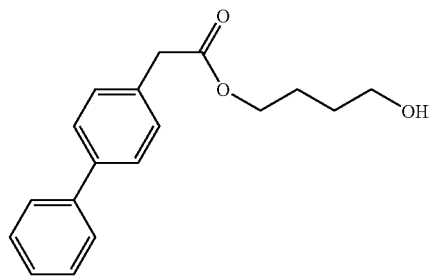
44  ABD-0043
    5BPA
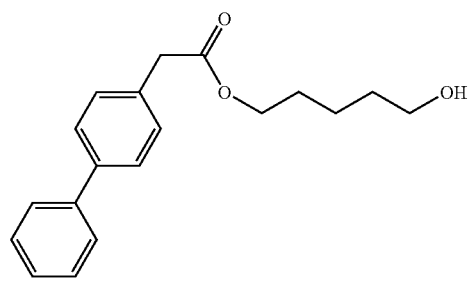

-continued
| 45 | ABD-0044 6BPA | 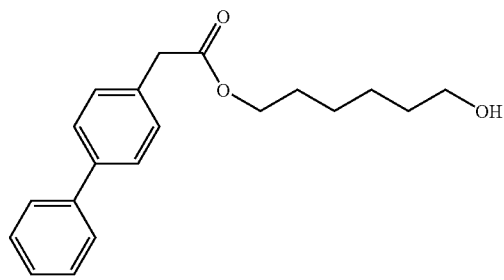 |
| 46 | ABD-0032 4N | 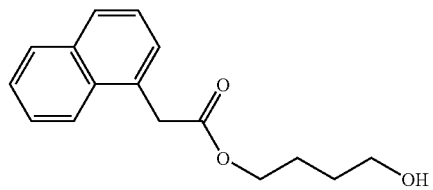 |
| 47 | ABD-0033 4H | 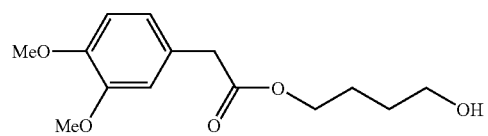 |
| 48 | ABD-0035 BuI | 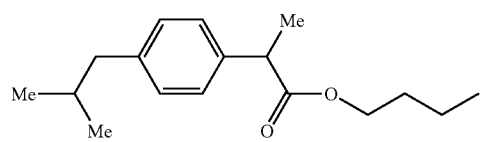 |
| 49 | ABD-0040 BuBPA | 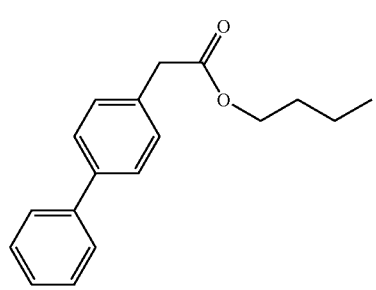 |
| 50 | ABD-0053 BuBP | 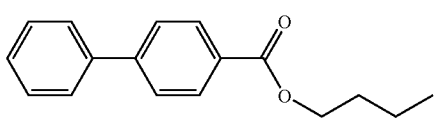 |
| 51 | ABD-0090 PBP | 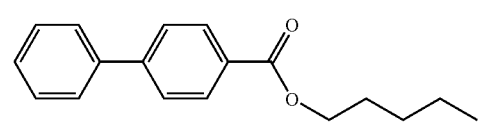 |
| 52 | ABD-0050 4BP-OMe | 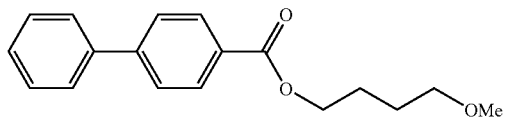 |
| 53 | ABD-0086 4BP-Br | 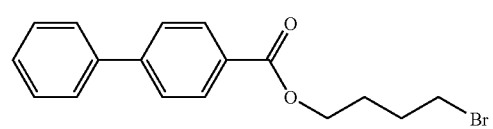 |

| 54 | ABD-0087 4BP-NO$_2$ | 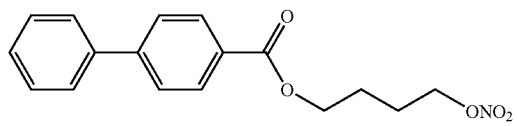 |
| 55 | ABD-0088 4xNO$_2$-BP | 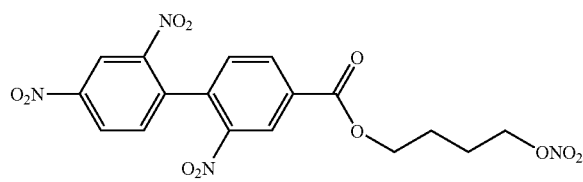 |

An especially preferred embodiment of the present invention is:

| 26 | ABD-0056 4BP | 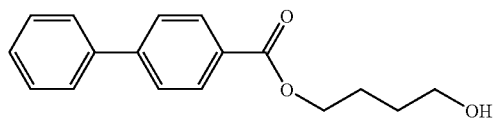 |

Another especially preferred embodiment of the present invention is:

| 7 | ABD-0085 10F | 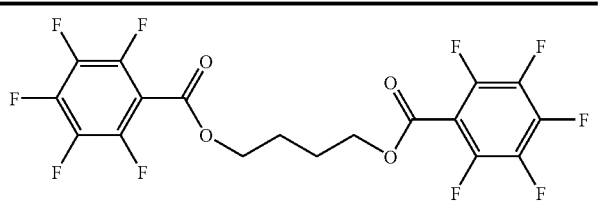 |

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alklidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), n-undecyl ($C_{11}$), dodecyl ($CO_2$), tridecyl ($CO_3$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), fluorene ($C_{13}$), phenalene ($C_{13}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (—C($CH_3$)=$CH_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —$CH_2$—C≡CH).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated.

Examples of groups of alkylidene groups include $C_{1-4}$alkylidene, $C_{1-7}$alkylidene, $C_{1-20}$alkylidene.

Examples of alkylidene groups include, but are not limited to, methylidene (=CH$_2$), ethylidene (=CH—CH$_3$), vinylidene (=C=CH$_2$), and isopropylidene (=C(CH$_3$)$_2$).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include C$_{1-4}$alkylidyne, C$_{1-7}$alkylidyne, C$_{1-20}$alkylidyne.

Examples of alkylidyne groups include, but are not limited to, methylidyne (≡CH) and ethylidyne (≡C—CH$_3$).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., C$_{3-20}$, C$_{3-7}$, C$_{5-6}$, etc.) denote the number of ring atoms, or range of number of ring atoms. For example, the term "C$_{5-6}$carbocyclyl," as used herein, pertains to a carbocyclyl group having 5 or 6 ring atoms. Examples of groups of carbocyclyl groups include C$_{3-20}$carbocyclyl, C$_{3-10}$carbocyclyl, C$_{5-10}$carbocyclyl, C$_{3-7}$carbocyclyl, and C$_{5-7}$carbocyclyl.

Examples of carbocyclic groups include, but are not limited to, those described above as cycloalkyl groups; those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., C$_{3-20}$, C$_{3-7}$, C$_{5-6}$, etc.) denote the number of ring atoms, or range of number of ring atoms, whether carbon atoms or heteroatoms. For example, the term "C$_{5-6}$heterocyclyl," as used herein, pertains to a heterocyclyl group having 5 or 6 ring atoms. Examples of groups of heterocyclyl groups include C$_{3-20}$heterocyclyl, C$_{3-7}$heterocyclyl, C$_{5-7}$heterocyclyl.

Examples of (non-aromatic) monocyclic heterocyclyl groups include, but are not limited to, those derived from:
N$_1$: aziridine (C$_3$), azetidine (C$_4$), pyrrolidine (tetrahydropyrrole) (C$_5$), pyrroline (e.g., 3-pyrroline, 2,5-dihydropyrrole) (C$_5$), 2H-pyrrole or 3H-pyrrole (isopyrrole, isoazole) (C$_5$), piperidine (C$_6$), dihydropyridine (C$_6$), tetrahydropyridine (C$_6$), azepine (C$_7$);
O$_1$: oxirane (C$_3$), oxetane (C$_4$), oxolane (tetrahydrofuran) (C$_5$), oxole (dihydrofuran) (C$_5$), oxane (tetrahydropyran) (C$_6$), dihydropyran (C$_6$), pyran (C$_6$), oxepin (C$_7$);
S$_1$: thiirane (C$_3$), thietane (C$_4$), thiolane (tetrahydrothiophene) (C$_5$), thiane (tetrahydrothiopyran) (C$_6$), thiepane (C$_7$);
O$_2$: dioxolane (C$_5$), dioxane (C$_6$), and dioxepane (C$_7$);
O$_3$: trioxane (C$_6$);
N$_2$: imidazolidine (C$_5$), pyrazolidine (diazolidine) (C$_5$), imidazoline (C$_5$), pyrazoline (dihydropyrazole) (C$_5$), piperazine (C$_6$);
N$_1$O$_1$: tetrahydrooxazole (C$_5$), dihydrooxazole (C$_5$), tetrahydroisoxazole (C$_5$), dihydroisoxazole (C$_5$), morpholine (C$_6$), tetrahydrooxazine (C$_6$), dihydrooxazine (C$_6$), oxazine (C$_6$);
N$_1$S$_1$: thiazoline (C$_5$), thiazolidine (C$_5$), thiomorpholine (C$_6$);
N$_2$O$_1$: oxadiazine (C$_6$);
O$_1$S$_1$: oxathiole (C$_5$) and oxathiane (thioxane) (C$_6$); and,
N$_1$O$_1$S$_1$: oxathiazine (C$_6$).

Examples of substituted (non-aromatic) monocyclic heterocyclyl groups include saccharides, in cyclic form, for example, furanoses (C$_5$), such as arabinofuranose, lyxofuranose, ribofuranose, and xylofuranse, and pyranoses (C$_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., C$_{3-20}$, C$_{5-7}$, C$_{5-6}$, etc.) denote the number of ring atoms, or range of number of ring atoms, whether carbon atoms or heteroatoms. For example, the term "C$_{5-6}$aryl," as used herein, pertains to an aryl group having 5 or 6 ring atoms. Examples of groups of aryl groups include C$_{3-20}$aryl, C$_{3-12}$aryl, C$_{5-12}$aryl, C$_{5-7}$aryl, and C$_{5-6}$aryl.

The ring atoms may be all carbon atoms, as in "carboaryl groups" (e.g., C$_{5-20}$carboaryl).

Examples of carboaryl groups include, but are not limited to, those derived from benzene (i.e., phenyl) (C$_6$), naphthalene (C$_{10}$), azulene (C$_{10}$), anthracene (C$_{14}$), phenanthrene (C$_{14}$), naphthacene (C$_{18}$), and pyrene (C$_{16}$).

Examples of aryl groups which comprise fused rings, at least one of which is an aromatic ring, include, but are not limited to, groups derived from indene (C$_9$), isoindene (C$_9$), and fluorene (C$_{13}$).

Alternatively, the ring atoms may include one or more heteroatoms, as in "heteroaryl groups" (e.g., C$_{5-20}$heteroaryl).

Examples of monocyclic heteroaryl groups include, but are not limited to, those derived from:
N$_1$: pyrrole (azole) (C$_5$), pyridine (azine) (C$_6$);
O$_1$: furan (oxole) (C$_5$);
S$_1$: thiophene (thiole) (C$_5$);
N$_1$O$_1$: oxazole (C$_5$), isoxazole (C$_5$), isoxazine (C$_6$);
N$_2$O$_1$: oxadiazole (furazan) (C$_5$);
N$_3$O$_1$: oxatriazole (C$_5$);
N$_1$S$_1$: thiazole (C$_5$), isothiazole (C$_5$);
N$_2$: imidazole (1,3-diazole) (C$_5$), pyrazole (1,2-diazole) (C$_5$), pyridazine (1,2-diazine) (C$_6$), pyrimidine (1,3-diazine) (C$_6$) (e.g., cytosine, thymine, uracil), pyrazine (1,4-diazine) (C$_6$);
N$_3$: triazole (C$_5$), triazine (C$_6$); and,
N$_4$: tetrazole (C$_5$).

Examples of heterocyclic groups (some of which are also heteroaryl groups) which comprise fused rings, include, but are not limited to:
C$_9$heterocyclic groups (with 2 fused rings) derived from benzofuran (O$_1$), isobenzofuran (O$_1$), indole (N$_1$), isoindole (N$_1$), purine (N$_4$) (e.g., adenine, guanine), benzimidazole (N$_2$), benzoxazole (N$_1$O$_1$), benzisoxazole (N$_1$O$_1$), benzodioxole (O$_2$), benzofurazan (N$_2$O$_1$), benzotriazole (N$_3$), benzothiofuran (S$_1$), benzothiazole (N$_1$S$_1$), benzothiadiazole (N$_2$S);
C$_{10}$heterocyclic groups (with 2 fused rings) derived from benzodioxan (O$_2$), quinoline (N$_1$), isoquinoline (N$_1$), benzoxazine (N$_1$O$_1$), benzodiazine (N$_2$), pyridopyridine (N$_2$), quinoxaline (N$_2$), quinazoline (N$_2$), phthalazine (N$_2$), pteridine (N$_4$);

$C_{13}$heterocyclic groups (with 3 fused rings) derived from carbazole ($N_1$), dibenzofuran ($O_1$), dibenzothiophene ($S_1$); and, $C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N=group may be substituted in the form of an N-oxide, that is, as —N(→O)=(also denoted —N$^+$(→O$^-$)=). For example, quinoline may be substituted to give quinoline N-oxide; pyridine to give pyridine N-oxide; benzofurazan to give benzofurazan —N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:

$C_9$: indenedione;
$C_{10}$: tetralone, decalone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);
cyclic carbonates (—O—C(=O)—O— in a ring), such as ethylene carbonate ($C_5$) and 1,2-propylene carbonate ($C_5$);
imides (—C(=O)—NR—C(=O)— in a ring), including but not limited to, succinimide ($C_5$), maleimide ($C_5$), phthalimide, and glutarimide ($C_6$);
lactones (cyclic esters, —O—C(=O)— in a ring), including, but not limited to, β-propiolactone, γ-butyrolactone, δ-valerolactone (2-piperidone), and ε-caprolactone;
lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);
cyclic carbamates (—O—C(=O)—NR— in a ring), such as 2-oxazolidone ($C_5$);
cyclic ureas (—NR—C(=O)—NR— in a ring), such as 2-imidazolidone ($C_5$) and pyrimidine-2,4-dione (e.g., thymine, uracil) ($C_6$).

The above alkyl, alkylidene, alkylidyne, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): —NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

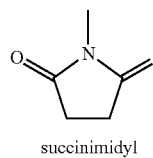
succinimidyl

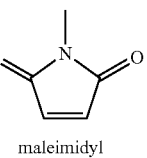
maleimidyl

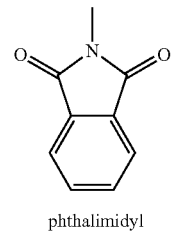
phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

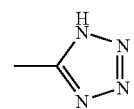

Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a 12 $C_{1-7}$alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amidine (amidino): —C(=NR)NR$_2$, wherein each R is an amidine substituent, for example, hydrogen, a $C_{1-7}$alkyl group, a $C_{3-20}$heterocyclyl group, or a $C_{5-20}$aryl group, preferably H or a $C_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH$_3$ and —SCH$_2$CH$_3$.

Disulfide: —SS—R, wherein R is a disulfide substituent, for example, a $C_{1-7}$alkyl group, a $C_{3-20}$heterocyclyl group, or a $C_{5-20}$aryl group, preferably a $C_{1-7}$alkyl group (also referred to herein as $C_{1-7}$alkyl disulfide). Examples of $C_{1-7}$alkyl disulfide groups include, but are not limited to, —SSCH$_3$ and —SSCH$_2$CH$_3$.

Sulfonic acid (sulfo): —S(=O)$_2$OH, —SO$_3$H.

Sulfonate (sulfonic acid ester): —S(=O)$_2$OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)$_2$OCH$_3$ and —S(=O)$_2$OCH$_2$CH$_3$.

Sulfinic acid: —S(=O)OH, —SO$_2$H.

Sulfinate (sulfinic acid ester): —S(=O)OR; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —S(=O)OCH$_3$ and —S(=O)OCH$_2$CH$_3$.

Sulfate: —OS(=O)$_2$OR; wherein R is a sulfate substituent, for example, a $C_{1-7}$alkyl group, a $C_{3-20}$heterocyclyl group, or a $C_{5-20}$aryl group, preferably a $C_{1-7}$alkyl group. Examples of sulfate groups include, but are not limited to, —OS(=O)$_2$OCH$_3$ and —SO(=O)$_2$OCH$_2$CH$_3$.

Sulfone (sulfonyl): —S(=O)$_2$R, wherein R is a sulfone substituent, for example, a $C_{1-7}$alkyl group, a $C_{3-20}$heterocyclyl group, or a $C_{5-20}$aryl group, preferably a $C_{1-7}$alkyl group, for example, a fluorinated or perfluorinated $C_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfine (sulfinyl, sulfoxide): —S(=O)R, wherein R is a sulfine substituent, for example, a $C_{1-7}$alkyl group, a $C_{3-20}$heterocyclyl group, or a $C_{5-20}$aryl group, preferably a $C_{1-7}$alkyl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a $C_{1-7}$alkyl group, a $C_{3-20}$heterocyclyl group, or a $C_{5-20}$aryl group, preferably a $C_{1-17}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$$_1$ wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Phosphino (phosphine): —PR$_2$, wherein R is a phosphino substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$alkyl group, a $C_{3-20}$heterocyclyl group, or a $C_{5-20}$aryl group, preferably a $C_{1-7}$alkyl group or a $C_{5-20}$aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2{}_2$, where R$^1$ and R$^2$ are phosphoramidate substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkoxy-$C_{5-20}$aryl group, e.g., as in anisole).

These and other specific examples of such substituted-substituents are described below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$perhaloalkyl group." Examples of $C_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

$C_{1-7}$haloalkoxy: —OR, wherein R is a $C_{1-7}$haloalkyl group. Examples of $C_{1-7}$haloalkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —CH$_2$OH, —CH$_2$CH$_2$OH, and —CH(OH)CH$_2$OH.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

$C_{1-7}$aminoalkylamino: The term "$C_{1-7}$aminoalkylamino," as used herein, pertains to an amino group, —NR$^1$R$^2$, in which one of the substituents, R$^1$ or R$^2$, is itself a $C_{1-7}$aminoalkyl group (—$C_{1-7}$alkyl-NR$^1$R$^2$). The $C_{1-7}$aminoalkylamino may be represented, for example, by the formula —NR$^1$-$C_{1-7}$alkyl-NR$^1$R$^2$. Examples of amino-$C_{1-7}$alkylamino groups include, but are not limited to, groups of the formula —NR$^1$(CH$_2$)$_n$NR$^1$R$^2$, where n is 1 to 6, for example, —NHCH$_2$NH$_2$, —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), and —NH(CH$_2$)$_6$NH(Et).

$C_{3-7}$cycloalkyl-$C_{1-7}$alkyl: The term "," as used herein, describes certain $C_{1-7}$alkyl groups which have been substituted with a $C_{3-7}$cycloalkyl group. Examples of such groiups include, but are not limited to, cyclopropylmethyl, cyclobutylmethyl, cyclopentylmethyl, and cyclohexylmethyl.

$C_{3-7}$cycloalkenyl-$C_{1-7}$alkyl: The term "," as used herein, describes certain $C_{1-7}$alkyl groups which have been substituted with a $C_{3-7}$cycloalkenyl group.

Examples of such groiups include, but are not limited to, cyclopropenylmethyl and cyclohexenylmethyl.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (as in toluene), xylyl (as in xylene), mesityl (as in mesitylene), styryl (as in styrene), and cumenyl (as in cumene).

$C_{1-7}$alkyl-$C_{5-20}$aryloxy: The term "$C_{1-7}$alkyl-$C_{5-20}$aryloxy," as used herein, describes certain $C_{5-20}$aryloxy groups which have been substituted with a $C_{1-7}$alkyl group. Examples of such groups include, but are not limited to, tolyloxy, xylyloxy, mesityloxy, and cumenyloxy.

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl), tolylmethyl, phenylethyl, triphenylmethyl (trityl), and cinnamyl (3-phenyl-2-propenyl, C$_6$H$_5$—CH=CH—CH$_2$—).

$C_{5-20}$aryl-$C_{1-7}$alkoxy: The term "$C_{5-20}$aryl-$C_{1-7}$alkoxy," as used herein, describes certain $C_{1-7}$alkoxy groups which have been substituted with a $C_{5-20}$aryl group. Examples of such groups include, but are not limited to, benzyloxy, tolylmethoxy, and phenylethoxy.

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

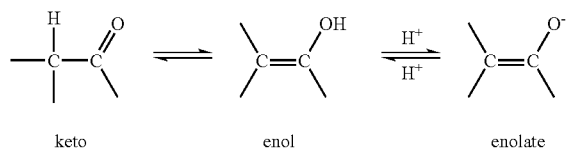

keto    enol    enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; 0 may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized-to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)Ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
C$_{1-7}$alkyl
(e.g., -Me, -Et, -nPr, -iPr, -nBu, -sBu, -iBu, -tBu);
C$_{1-7}$aminoalkyl
(e.g., aminoethyl; 2-(N,N-diethylamino)Ethyl; 2-(4-morpholino)Ethyl); and
acyloxy-C$_{1-7}$alkyl
(e.g., acyloxymethyl;
acyloxyethyl;
pivaloyloxymethyl;
acetoxymethyl;
1-acetoxyethyl;
1-(1-methoxy-1-methyl)Ethyl-carbonxyloxyethyl;
1-(benzoyloxy)Ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy) carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Synthesis of Alkane Diols Derivatives

Compounds suitable for use in the present invention may be synthesised using known methods. Suitable reagents and intermediates are commercially available. Additional compounds. Additionally, several methods for the chemical synthesis of suitable compounds (e.g., alkane diol esters) for use in present invention are described herein. These methods may be modified and/or adapted in known ways in order to facilitate the synthesis of additional compounds suitable for use in the present invention.

Examples of some suitable methods for the synthesis of alkane diol monoesters are described below.

In one method, esters of alkane diols are prepared by the reaction of the alkane diol with acyl halide (e.g., acyl chloride), optionally in the presence of a base (e.g., pyridine). For example, the alkane diol may first be dissolved in pyridine, and then the acyl halide added. If an excess of alkane diol is used, the mono-protected product is predominant; if an excess of acyl halide is used, the di-protected product is predominant. An example of such a method is illustrated in the following scheme.

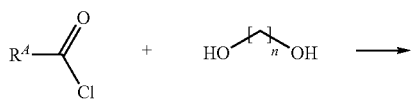

Scheme 1

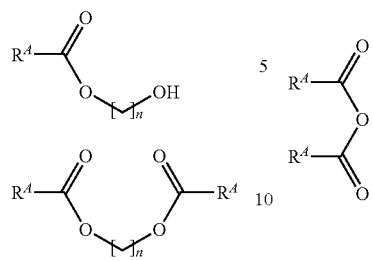

In another method, esters of alkane diols are prepared by the reaction of the alkane diol with a carboxylic acid, in the presence of a strong acid (e.g., $H_2SO_4$). For example, a small (catalytic) amount of strong acid may be used. If an excess of alkane diol is used, the mono-protected product is predominant; if an excess of carboxylic acid is used, the di-protected product is predominant. An example of such a method is illustrated in the following scheme.

Scheme 2

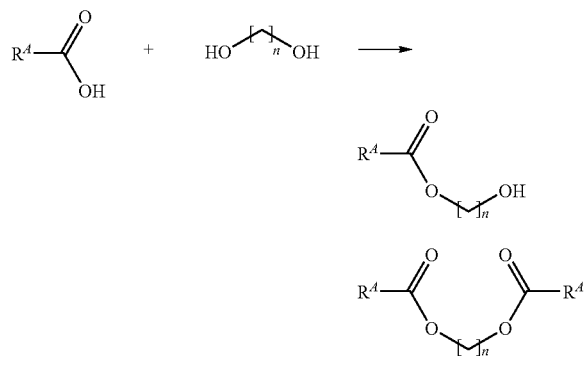

In another method, esters of alkane diols are prepared by the reaction of the alkane diol with an excess of acyl anhydride, in the presence of a base (e.g., pyridine). If an excess of alkane diol is used, the mono-protected product is predominant; if an excess of acyl anhydride is used, the di-protected product is predominant. An example of such a method is illustrated in the following scheme.

Scheme 3

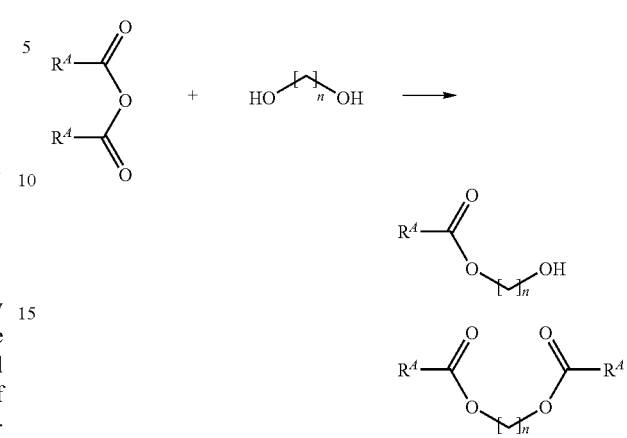

In another method, mixed esters of alkane diols are prepared by reaction of a mono-ester with an excess of acyl anhydride, in the presence of a base (e.g., pyridine). An example of such a method is illustrated in the following scheme.

Scheme 4

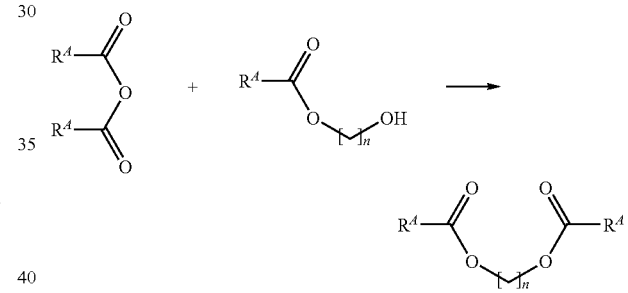

Suitable carboxylic acids may be prepared, for example, by reaction with aluminium trichloride ($AlCl_3$) and acetyl chloride ($CH_3COCl$) to give the corresponding methyl ketone, which is then reacted with NaOBr (formed by reaction of $Br_2$ with NaOH) to give the corresponding carboxylic acid. An example of such a method is illustrated in the following scheme.

Scheme 5

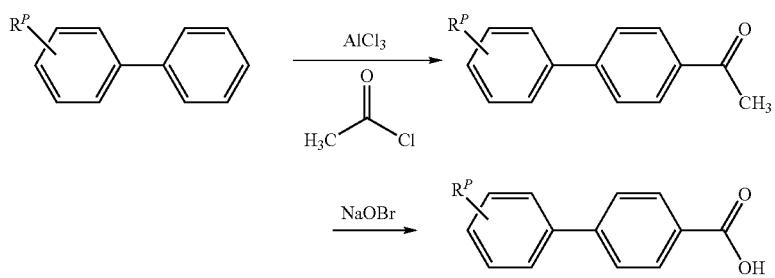

Suitable carboxylic acids may also be prepared by forming a Grignard reagent, which is then reacted with a borate, e.g., B(OMe)₃ to form a borane, which is then reacted with a suitable halide compound, in the presence of a suitable catalyst, e.g, PdCl₂, to yield the desired carboxylic acid. An example of such a method is illustrated in the following scheme.

Scheme 6

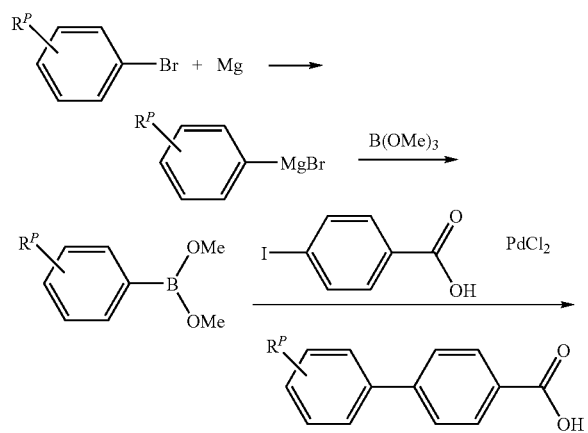

Suitable acyl halides may be prepared, for example, by reaction of the corresponding carboxylic acid with sulfonyl halide, e.g., sulfonyl chloride (SOCl₂). An example of such a method is illustrated in the following scheme.

Scheme 7

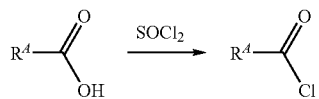

1,4-Butanediol mono(fluorobiphenyl-4-carboxylic acid) Esters can be synthesized by an analogous method, using a commercially available boronic acid (e.g., a fluorinated phenylboronic acid) and an iodobenzoic acid.

Commercially available fluorinated phenylboronic acids include, but are not limited to, 2,3-difluoro-; 2,4-difluoro-; 2,5-difluoro-; 2,6-difluoro-; 3,4-difluoro-; 3,5-difluoro-; 2,3,6-trifluoro-; and 2,4,6-trifluoro-phenylboronic acid (Sigma-Aldrich); as well as 2-fluoro-4-iodo-; 4-fluoro-3-methyl-; and 3,5-dibromo-phenylboronic acid (Lancaster). An example of such a method is illustrated in the following scheme. In one method, iodobenzoic acid (1.75 mmol), 3,4-difluorophenylboronic acid (3.5 mmol) and K₂CO₃ (2.6 mmol) are stirred in toluene (17 ml). Pd(PPh₃)₄ (0.05 mmol) is added and the mixture stirred for 2 hours at 85° C. After cooling, the mixture is diluted with ethyl acetate (17 ml), washed with saturated Na₂CO₃ (20 ml), water (20 ml), 10% citric acid (20 ml), water (20 ml) and saturated NaCl (20 ml). The solvent is evaporated and the product is purified by column chromatography. In another method, a suspension of Pd(PPh₃)₄ (0.05 mmol) in dimethoxyethanol (20 ml) is prepared. Iodobenzoic acid (2 mmol) is added and the mixture is stirred for 10 minutes. 3,4-Difluorophenylboronic acid (3 mmol) in ethanol (2 ml) is added followed by 2 M Na₂CO₃ (4 mmol). The mixture is refluxed for 18 hours, filtered and evaporated. The residue is washed with saturated NaCl (20 ml) and product is purified by column chromatography. See, for example, Miyaura et al., 1995.

Scheme 8

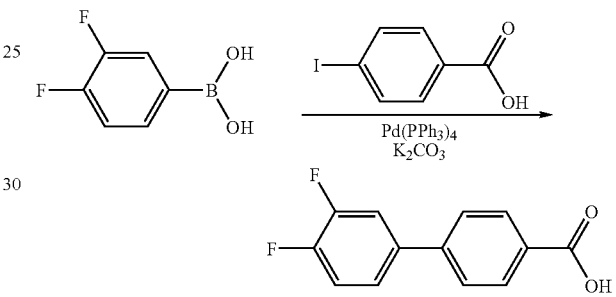

Methods for the preparation of compounds having a phosphonic acid group, include, for example, those described below.

In one method, ethenylidenebisphosphonate (CH₂=C(P(=O)(OR)₂)₂) is prepared from paraformaldehyde, diethylamine and a tetraalkyl methylene bisphosphonate (H₂C(P(=O)(OR)₂)₂), using, for example, the method described by Degenhardt and Burdsall, 1986. The ethenylidene-bisphosphonate is then reacted with, for example, ABD-0056 (4BP), in methylene chloride, in the presence of triethylamine, using, for example, the method described by Herczegh et al., 2002. The phosphate ester groups, e.g., ethyl groups, are removed e.g., with trimethylsilylbromide or left in place. An example of such a method is illustrated in the following scheme.

Scheme 9

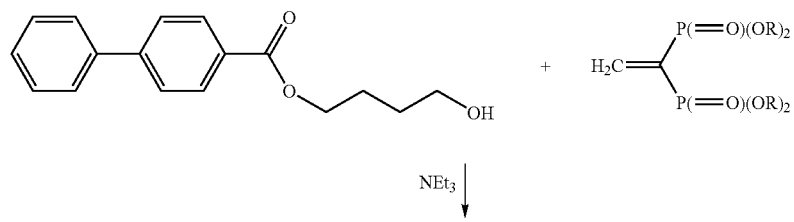

NEt₃ ↓

-continued

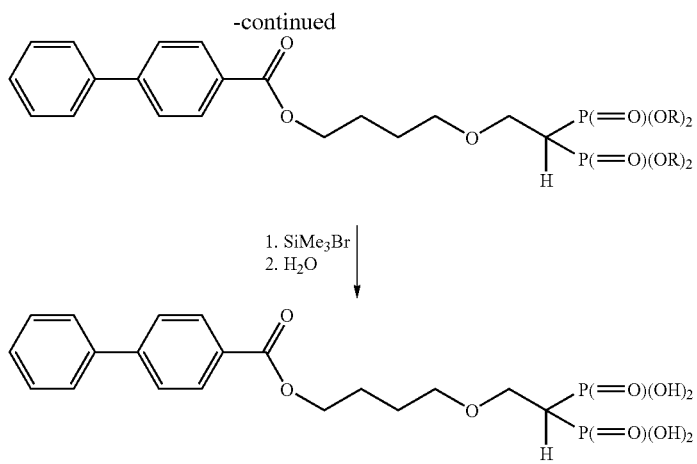

In another method, ABD-0056, for example, is heated with triethylorthoformate and diethyl phosphite (HP(=O)(OEt)$_2$) using, for example, the method described by Herczegh et al., 2002. Again, the phosphate ester groups, e.g., ethyl groups, are removed e.g., with trimethylsilylbromide or left in place. An example of such a method is illustrated in the following scheme.

-continued

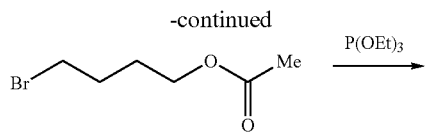

Scheme 10

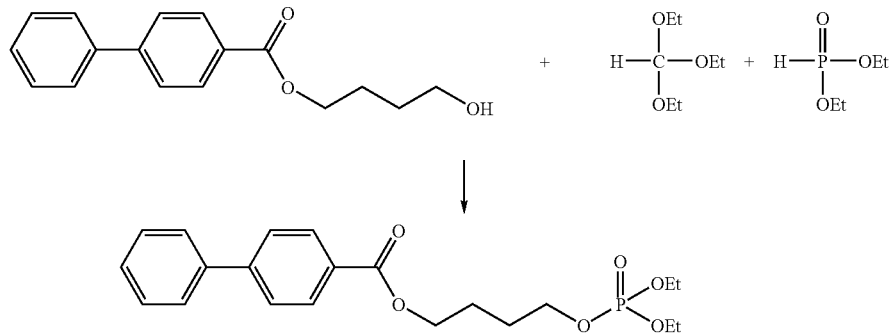

In another method, 4-bromobutanol (prepared, for example, by Method 9 described herein) is acetylated in acetic anhydride/pyridine. The resultant 4-acetoxybutylbromide is then heated with triethylphosphite to give diethyl-4-acetoxybutyl phosphonate using, for example, the method described by Eberhard and Westheimer, 1965. Hydrolysis with sulphuric acid removes the acetyl and ethyl groups to give the 4-hydroxybutylphosphonate. This is then linked to biphenyl-4-carboxylic acid using N-methyl morpholine and isobutyl chloroformate in a mixture of tetrahydrafuran and dimethylformamide. An example of such a method is illustrated in the following scheme.

-continued

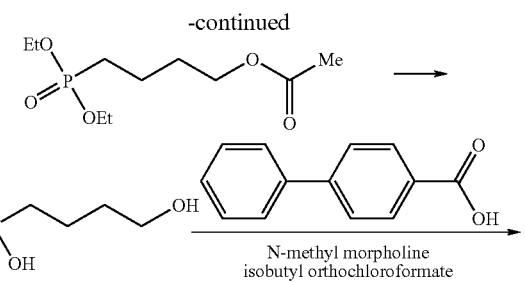

Scheme 11

In another method, 1,4-dibromobutane is heated with triethylphosphite to give diethyl-4-bromobutylphosphonate, for example, as described by Eberhard and Westheimer, 1965. The resultant bromide is then reacted with, for example, biphenyl-4-carboxylic acid in dimethylformamide, in the presence of potassium carbonate. Again, the phosphate ester groups, e.g., ethyl groups, are removed e.g., with trimethylsilylbromide or left in place. An example of such a method is illustrated in the following scheme.

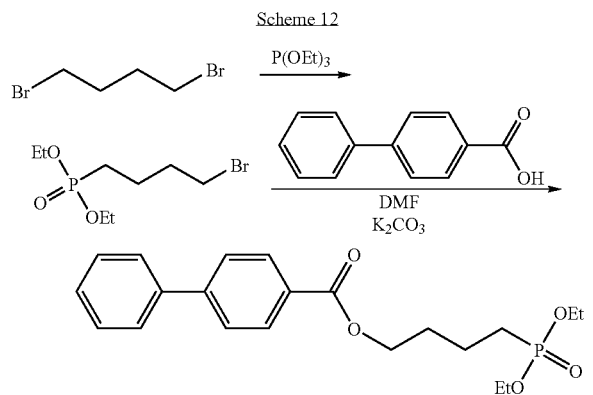

In another method, ABD-0086 (4BP-Br), for example, is gently refluxed with triisopropylphosphite to give the phosphonylated product. Remaining triisopropylphosphite is removed by distillation under reduced pressure and the residue is purified by column chromatography to give a clear oil. The isopropyl groups are removed using trimethylsilylbromide in dichloromethane, or left in place. An example of such a method is illustrated in the following scheme.

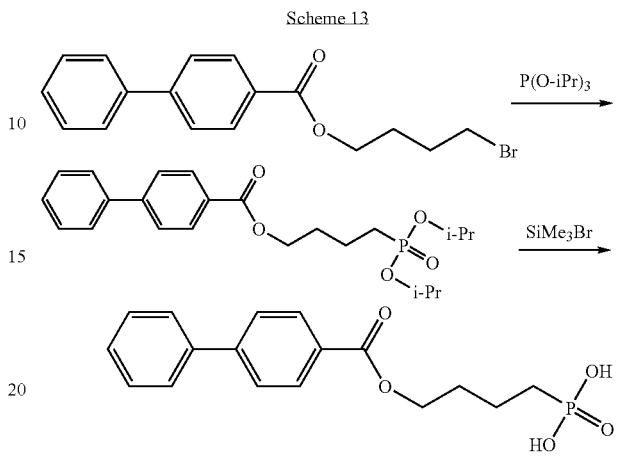

In another method, acrylic acid methyl ester (methyl acrylate) and methylene diphosphonic acid tetraethyl ester are mixed and saturated sodium ethanolate solution is added dropwise. The mixture is heated (e.g., to 90° C. for 2 hours) and the product obtained by distillation under reduced pressure. The ester groups were removed by hydrolysis in conc. HCl. See, e.g., Blum et al., 1978. An example of such a method is illustrated in the following scheme.

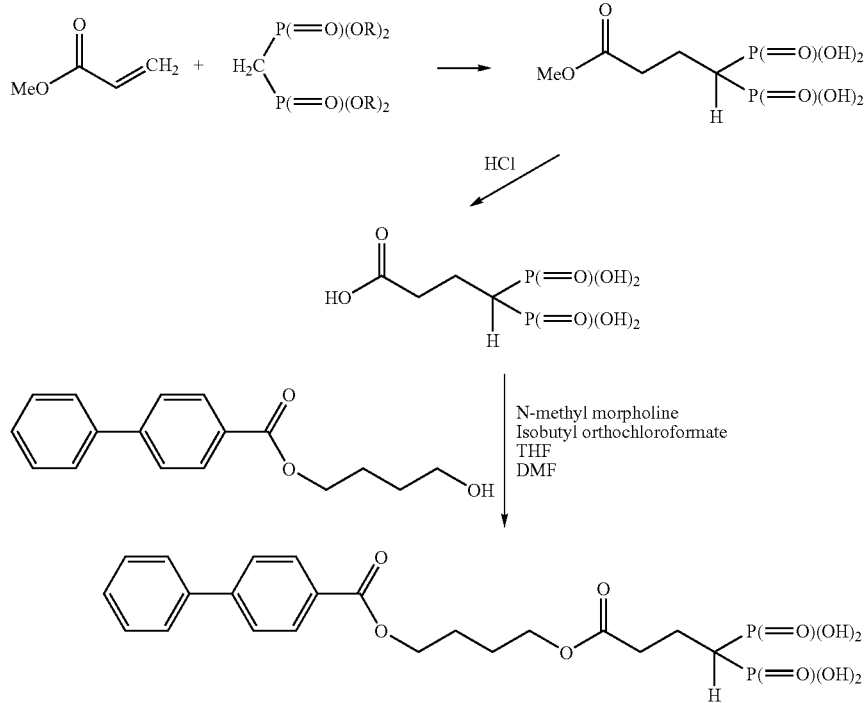

The products may be purified, for example, by column chromatography.

Use of Alkane Diol Derivatives

The present invention provides active compounds, specifically, active alkane diol derivatives (e.g., esters of alkane diols), as described herein, which inhibit osteoclasts, for example, inhibit of the survival, formation, and/or activity of osteoclasts, and/or which inhibit bone resorption. The compounds may therefore be referred to as "osteoclast inhibitors" and/or "bone resorption inhibitors."

The term "active," as used herein, pertains to compounds which are capable of inhibiting the survival, formation, and/or activity of osteociasts, and/or inhibiting bone resorption, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound inhibits the survival, formation, and/or activity of osteoclasts and/or inhibits bone resorption. For example, suitable methods which may conveniently be used in order to assess the inhibitory effects offered by a particular compound are described in the examples below.

The compounds of the present invention are also useful in the treatment of conditions mediated by osteoclasts (as "osteoclast inhibitors"), and/or conditions characterised by bone resorption (as "bone resorption inhibitors"). Examples of such conditions include, but are not limited to, the following:

Diseases of the skeleton, including but not limited to, pathologically low bone mineral density, such as osteoporosis (including, e.g., steroid induced osteoporosis); osteopetrosis; osteoarthritis; ectopic bone formation; Paget's disease of bone (osteitis deformans); and rheumatoid arthritis.

Neoplasia of bones, both as a primary tumour and as metastases, including but not limited to, osteosarcoma and osteoma (Zheng et al., 1998, *J. Cell Biochem.*, Vol. 70, p. 121) and cancer associated bone disease (e.g., multiple myeloma).

Examples of preferred conditions include osteoporosis, rheumatoid arthritis, cancer associated bone disease, and Paget's disease.

The compounds of the present invention have also macrophage inhibitory effects, and so are useful in the treatment of conditions associated with inflammation or activation of the immune system. Examples of such conditions include, but are not limited to, the following: Diseases with an inflammatory or autoimmune component, including allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including, but not limited to, type I diabetes, Crohn's disease, multiple sclerosis, arthritis, rheumatoid arthritis (Ogata et at., 1997, *J. Pathol.*, Vol. 182, p. 106); Gong et al., 1997, *J. Exp. Med., Vol* 186, p. 131), systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996, *J. Pathol.*, Vol. 178, p. 201), skin diseases such as psoriasis and lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997, *Am. J. Pathol.*, Vol. 150, p. 1711), hypersensitivity lung diseases such as hypersensitivity pneumonitis (Sugiyama et al., 1995, *Eur. Respir. J.*, Vol. 8, p. 1084), and inflammation related to histamine release from basophils (Dvorak et al., 1996, *J. Allergy Clin. Immunol.*, Vol. 98, p. 355), such as hay fever, histamine release from mast cells (Galli et al., 1989, *Ciba Foundation Symposium*, Vol. 147, p. 53), or mast cell tumors, types of type 1 hypersensitivity reactions (anaphylaxis, skin allergy, hives, allergic rhinitis, and allergic gastroenteritis); ulcerative colitis.

Thus, one aspect of the invention pertains to a method of inhibiting osteociast survival, formation, and activity, in vitro or in vivo, comprising contacting an osteoclast with an effective amount of an active compound, as described herein.

Another aspect of the invention pertains to a method of inhibiting bone resorption, in vitro or in vivo, comprising contacting cells in the bone microenvironment with a therapeutically-effective amount of an active compound, as described herein.

The term "cells in the bone microenvironment," as used herein, pertains to cells such as osteoblasts, osteoclasts, osteocytes and bone marrow stromal cells, which are located in close proximity to bone (e.g., within one hundred micrometers of the bone surface).

Another aspect of the present invention pertains to a method for the treatment of a condition mediated by osteociasts and/or characterised by bone resorption, as described herein, comprising administering to a subject suffering from said condition a therapeutically-effective amount of an active compound, as described herein, preferably in the form of a pharmaceutical composition.

Another aspect of the present invention pertains to a method for the treatment of a condition associated with inflammation or activation of the immune system, as described herein, comprising administering to a subject suffering from said condition a therapeutically-effective amount of an active compound, as described herein, preferably in the form of a pharmaceutical composition.

Another aspect of the present invention pertains to an active compound as described herein for use in a method of treatment of the human or animal body by therapy.

Another aspect of the present invention pertains to an active compound, as described herein, for use in a method of treatment a condition mediated by osteoclasts and/or characterised by bone resorption, as described herein, of the human or animal body by therapy.

Another aspect of the present invention pertains to an active compound, as described herein, for use in a method of treatment a condition mediated by osteoclasts, as described herein, of the human or animal body by therapy.

Another aspect of the present invention pertains to an active compound, as described herein, for use in a method of treatment a condition characterised by bone resorption, as described herein, of the human or animal body by therapy.

Another aspect of the present invention pertains to an active compound, as described herein, for use in a method of treatment of osteoporosis, rheumatoid arthritis, cancer associated bone disease, or Paget's disease of the human or animal body by therapy.

Another aspect of the present invention pertains to an active compound, as described herein, for use in a method of treatment a condition associated with inflammation or activation of the immune system, as described herein, of the human or animal body by therapy.

Another aspect of the present invention pertains to use of an active compound, as described herein, for the manufacture of a medicament for use in the treatment of a condition mediated by osteoclasts and/or characterised by bone resorption, as described herein.

Another aspect of the present invention pertains to use of an active compound, as described herein, for the manufacture of a medicament for use in the treatment of a condition mediated by osteoclasts, as described herein.

Another aspect of the present invention pertains to use of an active compound, as described herein, for the manufacture of a medicament for use in the treatment of a condition characterised by bone resorption, as described herein.

Another aspect of the present invention pertains to use of an active compound, as described herein, for the manufacture of a medicament for use in the treatment of osteoporosis, rheumatoid arthritis, cancer associated bone disease, or Paget's disease.

Another aspect of the present invention pertains to use of an active compound, as described herein, for the manufacture of a medicament for use in the treatment of a condition associated with inflammation or activation of the immune system, as described herein.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Active compounds may also be used as cell culture additives to inhibit osteoclasts, for example, to inhibit the survival, formation, and/or activity of osteoclasts.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other osteoclast inhibitors, etc.

Kits

One aspect of the invention pertains to a kit comprising (a) an active compound as described herein, or a composition comprising an active compound as described herein, e.g., preferably provided in a suitable container and/or with suitable packaging; and (b) instructions for use, e.g., written instructions on how to administer the active compound or composition.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a foetus.

In one preferred embodiment, the subject is a human.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g, by ingestion) include liquids, solutions (e.g., aqueous, non-aqueous), suspensions (e.g., aqueous, non-aqueous), emulsions (e.g., oil-in-water, water-in-oil), elixirs, syrups, electuades, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages-, dressings, depots, and reservoirs.

Tablets may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, butters, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 pg to about 250 mg (more typically about 100 pg to about 25 mg) per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

The identity and purity of the compounds was proven using $^{13}C$ and $^1H$ nmr in comparison with model literature compounds (ABD-0006 and ABD-0009) (4A and 4B), for which accurate melting or boiling points can also be obtained. The identity of many compounds was also ascertained using gas chromatography-mass spectroscopy (GC-MS).

General Methods

Method 1: Esterification Using an Acid Chloride and an Alcohol

The alcohol (0.1 mol) was dissolved in dry pyridine (50 ml) and chilled in an ice bath. The acid chloride (0.02 mol) was added dropwise with vigorous stirring and the mixture stirred overnight at room temperature. The mixture was poured into water (200 ml) and extracted with methylene chloride (100 ml). The organic phase was washed sequentially with 2 M HCl (3×100 ml), water, saturated NaHCO$_3$ and water. The solution was dried over Na$_2$SO$_4$ and evaporated to an oil or amorphous solid. The product was dissolved in methylene chloride (<5 ml), absorbed onto a column (silica gel 60, Merck) and purified using a mixture of light petroleum and ethyl acetate (usually a 1:1 mixture was satisfactory). Evaporation of the solvent gave an oil or a solid.

Method 2: Esterification Using an Acid and an Alcohol

The alcohol (0.2 mol) was heated in a boiling water bath. The acid (0.02 mol) was added followed by 20 drops of concentrated H$_2$SO$_4$ with vigorous stirring. Stirring was continued for 3 hours or until all of the acid had dissolved. The solution was poured into water (200 ml) and extracted with methylene chloride. The organic phase was washed with water, saturated NaHCO$_3$ and water. The solution was dried over Na$_2$SO$_4$ and purified as described in Method 1.

Method 3: Esterification Using an Acid Anhydride and an Alcohol

Pyridine (25 ml) and acetic anhydride (25 ml) were stirred at 0° C. The alcohol (4 mmol) in pyridine (10 ml) was added dropwise. The mixture was stirred overnight at room temperature and then in a boiling water bath for 2 hours. The mixture was then poured into water (200 ml) and extracted with methylene chloride (100 ml). The organic phase was washed sequentially with water, 2 M HCl (2×100 ml), water, saturated NaHCO$_3$ (100 ml) and water. The organic phase was dried over Na$_2$SO$_4$, evaporated and purified by column chromatography (light petroleum:ethyl acetate, 3:1).

Method 4: Preparation of Biphenylcarboxylates by Friedel-Crafts Acylation

The biphenyl (0.03 mol) was added to 1 M AlCl$_3$ in nitrobenzene (40 ml, 0.04 mol) with chilling in an ice bath. Acetyl chloride (0.06 mol) was added dropwise and the mixture stirred overnight at room temperature. The dark solution was poured into a mixture of crushed ice (150 ml), water (25 ml) and conc. HCl (50 ml). The organic phase was separated and the nitrobenzene removed by steam distillation to give a dark low melting solid. The solid was recrystallised from aqueous methanol.

Method 5: Oxidation of Acetate Group to Free Acid

NaOH (7 g) was dissolved in water (25 ml) and cooled in an ice bath. Bromine (7.8 g) was added dropwise to give a solution of NaOBr. The biphenyl acetate from Method 4 (0.01 mol) was dissolved in dioxane (35 ml) and warmed to 50° C. in a water bath. The NaOBr solution was added slowly to the stirred solution of the biphenyl acetate and stirring continued at 50° C. for a further 20 minutes. The solution was allowed to cool and a solution of sodium metabisulphite (Na$_2$S$_2$O$_5$) (8 g in 40 ml water) was added followed by water (170 ml). 50 ml of the liquid was evaporated under reduced pressure with heating. The remainder was acidified with conc._HCl (5 ml) and a white precipitate formed upon cooling. The precipitate was filtered and recrystallised from acetic acid.

Method 6: Preparation of Biphenyls by Suzuki Coupling

The substituted benzylbromide (e.g., 4-bromotoluene) (16 mmol) was dissolved in dry ether (15 ml) and reacted with magnesium (0.4 g, 16 mmol) to form the Grignard reagent. Gentle heating may be required to initiate the reaction. Trimethylborate (0.42 g, 4 mmol) was dissolved in ether (5 ml). The Grignard reagent was added dropwise to this solution with vigorous stirring. The reaction mixture was boiled for 15 minutes to give the aryl borane. A solution containing NaOH (2 g), 4-iodobenzoic acid (10 mmol), and PdCl$_2$ (0.1 mmol) in water (70 ml) was prepared and added dropwise to the aryl borane with vigorous stirring. Following addition, the mixture was boiled for 1 hour, allowed to cool and extracted with ether. The aqueous was extracted with methylene chloride. The aqueous was then acidified with HCl and extracted with methylene chloride followed by diethyl ether. These final two fractions were washed with saturated NaHCO$_3$ solution and water. All four fractions were combined, dried over Na$_2$SO$_4$ and evaporated to an amorphous solid. Purification by column chromatography (ethyl acetate:light petroleum, 1:1) gave the desired product as a white powder.

Method 7: Acetylation

The alcohol (10 mmol) was dissolved in pyridine (25 ml) and acetic anhydride (10 ml) was added dropwise. The mixture was stirred overnight, poured into water (200 ml) and extracted with methylene chloride (100 ml). The organic phase was washed sequentially with water, 2M HCl (2×100 ml), water, saturated NaHCO$_3$ (100 ml) and water. The organic phase was dried over Na$_2$SO$_4$, evaporated and purified by column chromatography (light petroleum:ethyl acetate, 3:1).

Method 8: Preparation of Acid Chloride

The acid (10 mmol) was dissolved in thionyl chloride (SOCl$_2$) (30 ml) and refluxed for 3 hours. The mixture was poured into acetic acid (100 ml) and left to stand until bubbling ceased. Volatile components were removed under vacuum and the mixture left to crystallise overnight. The desired acid chloride was collected by filtration.

Method 9: Preparation of 4-bromobutanol

48% Hydrobromic acid (200 ml) was added to refluxing tetrahydrafuran (400 ml) over a period of 1 hour. Reflux was continued for 4 hours. The solution was allowed to cool, excess HBr was neutralised with NaHCO$_3$ and partitioned with water. The organic phase was separated, washed with brine and dried over MgSO$_4$. Evaporation of the solvent gave 4-bromobutanol as an oil.

Example 1

1,4-Butanediol di(acetic acid)Ester (ABD-0006)
(4A)

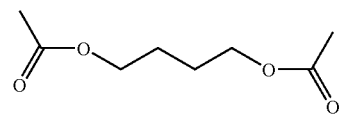

The title compound was prepared from acetic anhydride and 1,4-butanediol using Method 3, and was purified by distillation under reduced pressure to give a clear oil (yield 60%). $\delta_C$ (CDCl$_3$, 62.9 MHz): 20.96, 25.3, 63.9 and 171.1. $\delta_H$ (CDCl$_3$, 250 MHz): 1.70 (4H, m), 2.02 (6H, m) and 4.10 (4H, m).

Example 2

1,4-Butanediol di(butanoic acid)Ester (ABD-0007) (4BU)

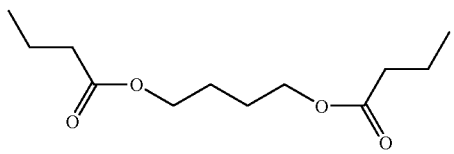

The title compound was prepared from butyric acid and 1,4-butanediol using Method 2, to give a clear oil (yield 85%). $\delta_C$ (CDCl$_3$, 62.9 MHz): 13.6, 18.4, 25.4, 36.2, 63.7 and 173.7. $\delta_H$ (CDCl$_3$, 250 MHz): 0.92 (6H, t, J 7.3), 1.58-1.70 (8H, m), 2.26 (4H, t, J 7.3) and 4.07 (4H, m).

Example 3

1,4-Butanediol di(cyclclohexanecarboxylic acid)Ester (ABD-0019) (4C)

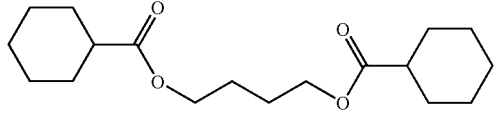

The title compound was prepared from cyclohexanecarbonyl chloride and 1,4-butanediol using Method 1 to give a clear oil which solidified over time (yield 30%). $\delta_C$ (CDCl$_3$, 62.9 MHz): 25.5, 25.8, 29.0, 43.2, 63.6 and 176.1.

Example 4

1,4-Butanediol di(benzoic acid)Ester (ABD-0009) (4B)

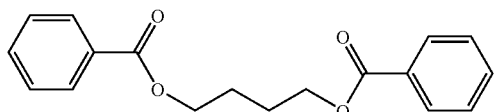

The title compound was prepared from benzoic acid and 1,4-butanediol using Method 2, to give a white crystalline solid (yield 80%). $\delta_C$ (CDCl$_3$, 62.9 MHz): 25.6, 64.5, 128.4, 129.6, 130.3, 133.0 and 166.6. $\delta_H$ (CDCl$_3$, 250 MHz): 1.95 (4H, m), 4.40 (4H, m), 7.43 (4H, t, J 7.3), 7.54 (2H, d, J 7.0) and 8.04 (4H, d, J 7.0).

Example 5

1,4-Butanediol di(phenylacetic acid)Ester (ABD-0014) (4P)

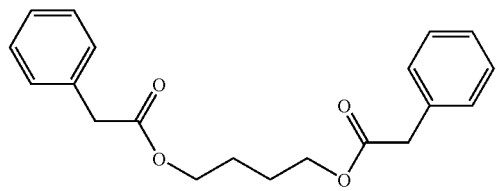

The title compound was prepared from phenylacetic acid and 1,4-butanediol using Method 2, to give a white solid (yield 50%). $\delta_C$ (CDCl$_3$, 62.9 MHz): 19.8, 23.8, 36.3, 57.1, 59.5, 121.9, 123.4, 124.1, 128.9, 157.4 and 166.5. $\delta_H$ (CDCl$_3$, 250 MHz): 1.64 (4H, m), 3.61 (4H, s), 4.08 (4H, m) and 7.29 (10H, m).

Example 6

1,6-Hexanediol di(phenylacetic acid)Ester (ABD-0017) (6P)

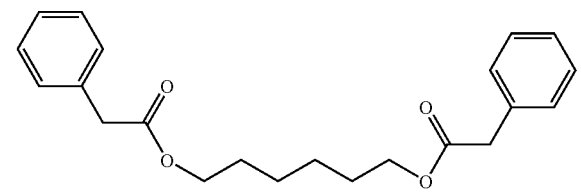

The title compound was prepared from phenylacetic acid and 1,6-hexanediol using Method 2 to give a clear oil (yield 90%). $\delta_c$ (CDCl$_3$, 62.9 MHz): 25.5, 28.4, 41.5, 64.7, 127.1, 128.6, 129.3, 134.2, and 171.6.

Example 7

1,4-Butanediol di(pentafluorobenzoic acid)Ester (ABD-0085) (10F)

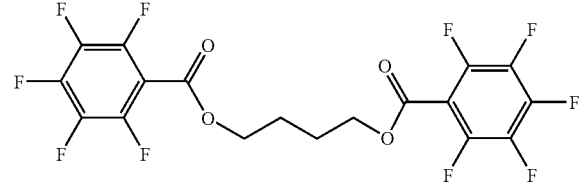

The title compound was prepared from pentafluorobenzoyl chloride and 1,4-butanediol using Method 1 to give a white solid. Column chromatography gave the title compound as the first fraction (yield 20%). $\delta_C$ (CDCl$_3$, 62.9 MHz): 25.0 and 66.0.

Example 8

1,4-Butanediol di(2,4-difluorobenzoic acid)Ester (ABD-0111) (D2,4FB)

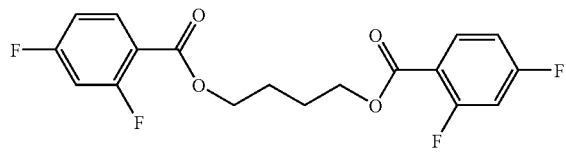

The title compound was prepared from 2,4-difluorobenzoyl chloride and 1,4-butanediol using Method 1, to give a clear oil. Column chromatography gave the title compound as the first fraction (yield 20%). $\delta_C$ (CDCl$_3$, 62.9 MHz): 25.4, 64.9, 105.2 (t, J 26.4), 111.6 (dd, J 21.5, 2.9) and 133.9 (d, J 10.7).

Example 9

2,2,3,3-tetrafluorobutan-1,4-diol di(biphenyl-4-carboxylic acid)Ester (ABD-0096) (DBP-4F)

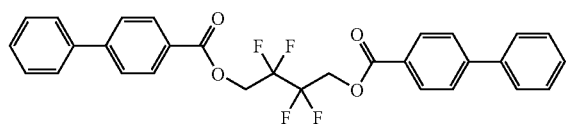

The title compound was prepared from 2,2,3,3-tetrafluorobutane-1,4-diol and biphenylcarbonyl chloride using Method 1 to give a white (yield 20%). Purification by column chromatography (ethyl acetate:light petroleum, 1:1) gave the title compound as the first fraction. $\delta_C$ (CDCl$_3$, 62.9 MHz): 127.3, 127.3, 128.4, 129.0, 130.6, 139.8, 146.5 and 165.4.

Example 10

Biphenyl-4-carboxylic acid (4-acetoxy)butyl ester (ABD-0049) (4BP-acetate)

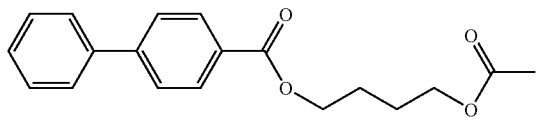

The title compound was prepared from ABD-0056 using Method 7 to give a white solid (yield 90%). $\delta_C$ (CDCl$_3$, 62.9 MHz): 21.0, 25.4, 25.5, 64.0, 64.5, 127.1, 127.3, 128.2, 129.0, 130.1, 140.0, 145.7, 166.5 and 171.2. $\delta_H$ (CDCl$_3$, 250 MHz): 1.8 (4H, s, 2×CH$_2$), 2.0 (3H, s, COCH$_3$), 4.1 (2H, t, J 6.3), 4.4 (2H, t, J 6.3), 7.4 (3H, m), 7.6 (4H, 2×d) and 8.1 (2H, d, J 8.8).

Example 11

1,4-Butanediol mono(benzoic acid)Ester (ABD-0008) (4 MB)

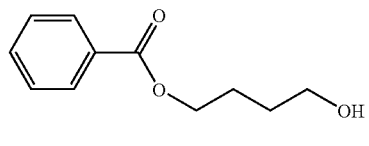

The title compound was prepared from benzoyl chloride and 1,4-butanediol using Method 1 to give a pale oil (yield 40%). $\delta_C$ (CDCl$_3$, 62.9 MHz): 25.2, 29.1, 62.4, 64.8, 128.4, 129.6, 132.9, 133.0, and 164.1.

Example 12

1,4-Butanediol mono(4-iodobenzoic acid)Ester (ABD-0069) (4IB)

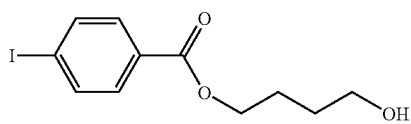

The title compound was prepared from 4-iodobenzoyl chloride and 1,4-butanediol using Method 1 to give a clear oil (yield 90%). $\delta_C$ (CDCl$_3$, 62.9 MHz): 25.2, 29.2, 62.3, 65.1, 100.7, 129.8, 131.0, 137.7 and 166.2.

Example 13

1,4-Butanediol mono(pentafluorobenzoic acid)Ester (ABD-0077) (4FB)

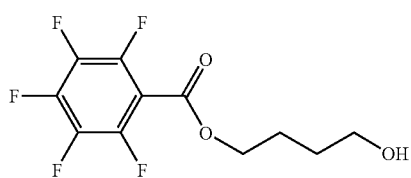

The title compound was prepared from pentafluorobenzoyl chloride and 1,4-butanediol using Method 1 to give a clear oil. Column chromatography gave the title compound as the second fraction (yield 55%). $\delta_C$ (CDCl$_3$, 62.9 MHz): 25.0, 28.9, 62.2 and 66.7. $\delta_H$ (CDCl$_3$, 250 MHz): 1.46 (1H, s, OH), 1.72 (2H, m), 1.86 (2H, m), 3.73 (2H, t, J 6.4) and 4.42 (2H, t, J 6.4).

Example 14

1,4-Butanediol mono(2,3,6-trifluorobenzoic acid)Ester (ABD-0106) (2,3,6-FB)

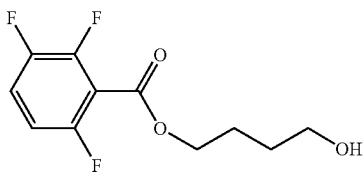

The title compound was prepared from 2,3,6-trifluorobenzoic acid and 1,4-butanediol using Method 2, to give a clear oil. Column chromatography gave the title compound as the second fraction (yield 60%). $\delta_C$ (CDCl$_3$, 62.9 MHz): 25.0, 29.0, 62.3, 66.2, 111.6 and 119.6.

Example 15

1,4-Butanediol mono(3,4-difluorobenzoic acid)Ester (ABD-0107) (3,4-FB)

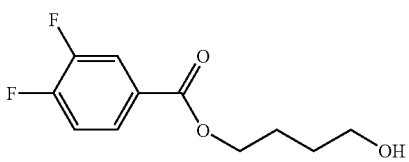

The title compound was prepared from 3,4-difluorobenzoyl chloride and 1,4-butanediol using Method 1, to give a clear oil. Column chromatography gave the title compound as the second fraction (yield 70%). $\delta_C$ (CDCl$_3$, 62.9 MHz): 25.2, 29.1, 62.3, 65.4, 117.4 (d, J 17.6), 118.9 (d, J 18.6), 126.5 (d, J 3.9) and 127.3.

Example 16

1,4-Butanediol mono(2,3,4-trifluorobenzoic acid)Ester (ABD-0108) (2,3,4-FB)

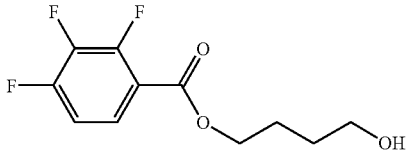

The title compound was prepared from 2,3,4-trifluorobenzoic acid and 1,4-butanediol using Method 2, to give a clear oil. Column chromatography gave the title compound as the second fraction (yield 85%). $\delta_C$ (CDCl$_3$, 62.9 MHz): 25.1, 29.1, 62.3, 65.7, 112.3 and 126.1.

Example 17

1,4-Butanediol mono(2,4,5-trifluorobenzoic acid)Ester (ABD-0109) (2,4,5-FB)

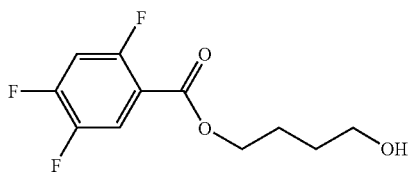

The title compound was prepared from 2,4,5-trifluorobenzoyl chloride and 1,4-butanediol using Method 1, to give a white solid. Column chromatography gave the title compound as the second fraction (yield 65%). $\delta_C$ (CDCl$_3$, 62.9 MHz): 25.1, 29.0, 62.1, 65.7, 107.1 and 120.0.

Example 18

1,4-Butanediol mono(2,4-difluorobenzoic acid)Ester (ABD-0110) (2,4-FB)

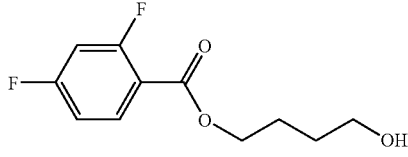

The title compound was prepared from 2,4-difluorobenzoyl chloride and 1,4-butanediol using Method 1, to give a clear oil. Column chromatography gave the title compound as the second fraction (yield 70%). $\delta_C$ (CDCl$_3$, 62.9 MHz): 25.1, 29.2, 62.3, 65.3, 105.2 (t, J26.4), 111.6 (dd, J21.5, 2.9) and 133.9 (d, J 10.7).

Example 19

1,3-Propanediol mono[2-(4-isobutylphenyl)Propionic acid]ester (ABD-0037) (31)

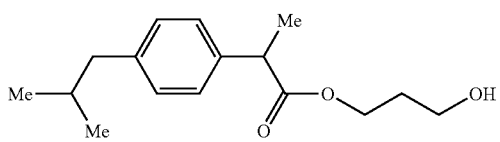

The title compound was prepared from ibuprofen and 1,3-propanediol using Method 2 to give a clear oil (yield 70%). $\delta_C$ (CDCl$_3$, 62.9 MHz): 18.4, 22.4, 30.2, 31.7, 45.0, 45.2, 59.1, 61.7, 127.1, 129.4, 137.7, 140.7 and 175.3.

Example 20

1,4-Butanediol mono[2-(4-isobutylphenyl)Propionic acid]ester (ABD-0036) (41)

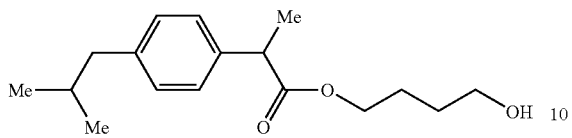

The title compound was prepared from ibuprofen and 1,4-butanediol using Method 2 to give a clear oil (yield 75%). $\delta_C$ (CDCl$_3$, 62.9 MHz): 18.4, 22.4, 25.0, 29.0, 30.2, 45.0, 62.2, 64.5, 127.2, 129.3, 137.8, 140.6 and 174.9.

Example 21

1,5-Pentanediol mono[2-(4-isobutylphenyl)Propionic acid]ester (ABD-0038) (51)

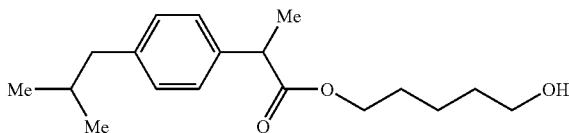

The title compound was prepared from ibuprofen and 1,5-pentanediol using Method 2 to give a clear oil (yield 70%). $\delta_C$ (CDCl$_3$, 62.9 MHz): 18.5, 22.1, 22.4, 28.3, 30.2, 32.2, 45.0, 45.2, 62.7, 64.6, 127.2, 129.3, 137.9, 140.5 and 174.9.

Example 22

1,6-Hexanediol mono[2-(4-isobutylphenyl)Propionic acid]ester (ABD-0039) (61)

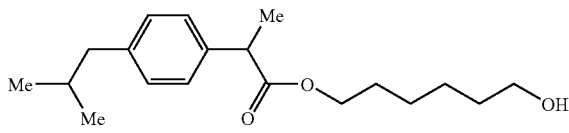

The title compound was prepared from ibuprofen and 1,6-hexanediol using Method 2 to give a clear oil (yield 75%). $\delta_C$ (CDCl$_3$, 62.9 MHz): 18.5, 22.4, 25.3, 25.6, 28.5, 30.2, 32.5, 45.0, 45.2, 62.7, 64.6, 127.2, 129.3, 137.9, 140.5 and 174.9.

Example 23

1,4-Butanediol mono(4-benzylbenzoic acid)Ester (ABD-0034) (4PT)

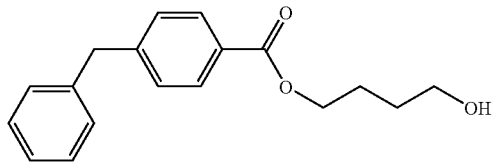

The title compound was prepared from 4-benzylbenzoic acid and 1,4-butanediol using Method 2, to give a clear oil (yield 45%). $\delta_C$ (CDCl$_3$, 62.9 MHz): 25.1, 29.1, 39.7, 62.4, 64.8, 126.0, 128.9, 129.1, 131.7, 132.9, 130.1, 140.8, 143.4 and 172.8.

Example 24

1,4-Butanediol (biphenyl-2-carboxylic acid) ester (ABD-0059) (4BPX)

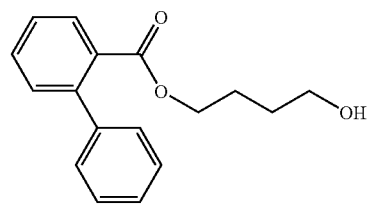

The title compound was prepared from biphenyl-2-carboxylic acid and 1,4-butanediol using Method 2 to give a clear oil (yield 40%). $\delta_C$ (CDCl$_3$, 62.9 MHz): 24.6, 28.9, 62.3, 64.9, 127.3, 128.1, 128.5, 129.9, 130.6, 130.7, 131.2, 131.9, 141.2, 141.7, 142.3, 143.2 and 169.2.

Example 25

1,3-Propanediol mono(biphenyl-4-carboxylic acid)Ester (ABD-0057) (3BP)

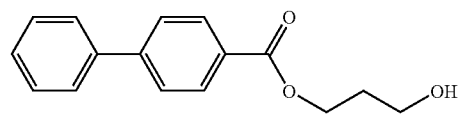

The title compound was prepared from biphenyl-4-carbonyl chloride and 1,3-propanediol using Method 1 to give a white solid (yield 80%). $\delta_C$ (CDCl$_3$, 62.9 MHz): 14.2, 30.9, 32.0, 127.1, 127.3, 128.2, 129.3, 130.1, 140.0, 145.8 and 166.9.

Example 26

1,4-Butanediol mono(biphenyl-4-carboxylic acid)Ester (ABD-0056) (4BP)

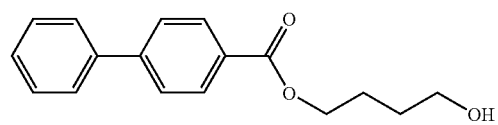

The title compound was prepared from biphenyl-4-carbonyl chloride and 1,4-butanediol using Method 1 to give a white solid (yield 85%). $\delta_C$ (CDCl$_3$, 62.9 MHz): 25.3, 29.3, 62.4, 64.8, 127.1, 127.3, 128.2, 129.0, 129.1, 130.1, 130.7, 140.0, 145.7 and 166.6. $\delta_H$ (CDCl$_3$, 250 MHz): 1.74-1.77 (2H, m), 1.86-1.89 (2H, m), 2.63 (1H, s, OH), 3.74 (2H, t, J6.3), 4.38 (2H, t, J6.3), 7.45 (3H, m), 7.63 (4H, m) and 8.10 (2H, d, J 8.5). m/z (Found M, 270. C$_{17}$H$_{18}$O$_3$ requires 270).

Example 27

1,5-Pentanediol mono(biphenyl-4-carboxylic acid)Ester (ABD-0055) (5BP)

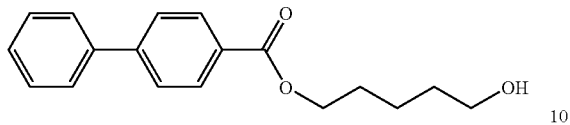

The title compound was prepared from biphenyl-4-carbonyl chloride and 1,5-pentanediol using Method 1 to give a white solid (yield 80%). $\delta_C$ (CDCl$_3$, 62.9 MHz) 22.4, 28.6, 32.4, 62.7, 65.0, 127.1, 127.3, 128.2, 129.0, 129.1, 130.1, 140.0, 145.6 and 166.7; m/z (Found M, 284. C$_{18}$H$_{20}$O$_3$ requires 284).

Example 28

1,6-Hexanediol mono(biphenyl-4-carboxylic acid)Ester (ABD-0054) (6BP)

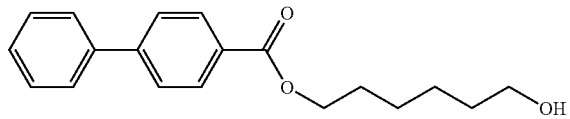

The title compound was prepared from biphenyl-4-carbonyl chloride and 1,6-hexanediol using Method 1 to give a white solid (yield 85%). $\delta_C$ (CDCl$_3$, 62.9 MHz) 25.5, 25.9, 28.8, 32.7, 62.9, 65.0, 127.1, 127.3, 128.2, 129.0, 129.2, 130.1, 140.1, 145.7 and 166.7. m/z (Found M, 298. C$_{19}$H$_{22}$O$_3$ requires 298).

Example 29

2,2,3,3-Tetrafluoro-butane-1,4-diol mono(biphenyl-4-carboxylic acid)Ester (ABD-0095) (BP-4F)

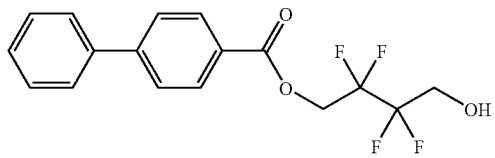

The title compound was prepared from biphenyl-4-carbonyl chloride and 2,2,3,3-tetrafluorobutane-1,4-diol using Method 1 to give a clear oil (yield 65%). Purification by column chromatography (ethyl acetate:light petroleum, 1:1) gave the title compound as the second fraction. $\delta_C$ (CDCl$_3$, 62.9 MHz): 60.4 (t, J 26.4), 127.3, 127.3, 128.4, 129.0, 130.6, 139.8, 146.5 and 165.4.

Example 30

1,4-Butanediol mono(4'-methyl-biphenyl-4-carboxylic acid)Ester (ABD-0070) (Me4BP)

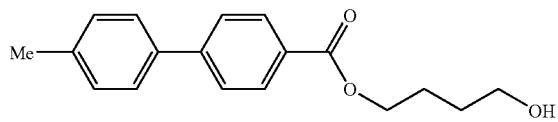

The title compound was prepared from 4'-methyl-biphenyl-4-carboxylic acid (prepared from 4-bromotoluene using Method 6) and 1,4-butanediol using Method 2 to give a white solid (yield 20%). $\delta_C$ (CDCl$_3$, 62.9 MHz): 21.2, 25.3, 29.3, 62.4, 64.8, 126.8, 127.1, 128.8, 129.7, 130.1, 137.1, 138.2, 145.6 and 166.7.

Example 31

1,4-Butanediol mono(4'-hydroxy-biphenyl-4-carboxylic acid)Ester (ABD-0072) (HO4BP)

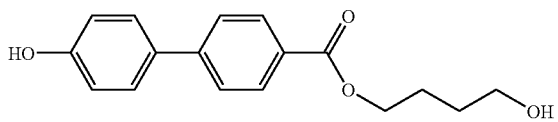

The title compound was prepared from 4'-hydroxy-biphenyl-4-carboxylic acid (which was first protected as the 4'-tertiarybutylchlorodiphenylsilyl ether) and 1,4-butanediol using Method 2 (the silyl protecting group was removed during the reaction) to give the title product as a white powder (yield 15%). $\delta_C$ (CDCl$_3$, 62.9 MHz): 25.1, 29.0, 60.3, 64.6, 115.9, 126.0, 127.6, 128.2, 129.5, 144.7, 158.0 and 165.7.

The protected acid was prepared as follows: 4'-Hydroxy-biphenyl-4-carboxylic acid (4.2 g, 20 mmol) was dissolved in pyridine (50 ml). Tertiarybutylchlorodiphenylsilane (TB-DPSi—Cl) (11 g, 40 mmol) was added dropwise, followed by a catalytic amount of 4-dimethylaminopyridine (0.1 g). The solution was left to stir overnight, then poured into water (200 ml) and extracted with methylene chloride (100 ml). The organic phase was washed with 2 M HCl (100 ml) which caused the precipitation of an acid. The acid was collected by filtration, dissolved in diethyl ether and washed with water. The methylene chloride layer was washed with water, the two organic phases combined and dried over Na$_2$SO$_4$. Evaporation and purification by column chromatography (light petroleum:ethyl acetate, 2:1) gave the silylated product as a white solid.

Example 32

1,4-Butanediol mono(3',4'-dimethyl-biphenyl-4-carboxylic acid)Ester (ABD-0089) (Xy4BP)

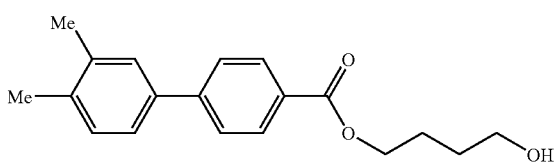

The title compound was prepared from 3',4'-dimethyl-biphenyl-4-carboxylic acid (prepared from 4-bromo-o-xylene using Method 6) and 1,4-butanediol using Method 2 to give a clear oil (yield 15%). $\delta_C$ (CDCl$_3$, 62.9 MHz): 19.5, 20.0, 25.3, 29.2, 62.3, 64:8; 124.6, 126.8, 128.5, 128.6, 130.0, 130.2, 136.8, 137.2, 137.5, 145.8 and 166.8.

Example 33

1,4-Butanediol mono(4'-ethyl-biphenyl-4-carboxylic acid)Ester (ABD-0094) (Et4BP)

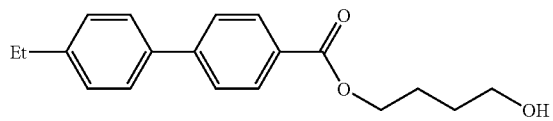

The title compound was prepared from 4'-ethyl-biphenyl-4-carboxylic acid (prepared from 4-bromo-ethylbenzene using Method 6) and 1,4-butanediol using Method 2 to give a white powder (yield 25%). $\delta_C$ (CDCl$_3$, 62.9 MHz): 15.6, 25.3, 28.6, 29.3, 62.4, 64.8, 126.9, 127.2, 128.5, 128.8, 130.1, 137.3, 144.5, 145.6 and 166.7. $\delta_H$ (CDCl$_3$, 250 MHz): 1.27 (3H, t, J 7.6), 1.76 (2H, m), 1.86 (2H, m), 2.43 (1H, br s), 2.70 (2H, q, J 7.6), 3.74 (2H, t, J 6.4), 4.38 (2H, t, J 6.4), 7.29 (2H, d, J 8.2), 7.54 (2H, d, J 8.2), 7.64 (2H, d, J 8.2), 8.08 (2H, d, J 8.2).

Example 34

1,4-Butanediol mono(4'-methoxy-biphenyl-4-carboxylic acid)Ester (ABD-0097) (4-OMeBP)

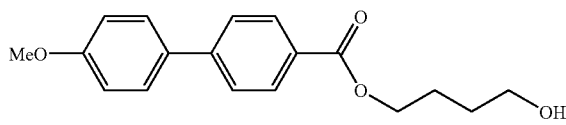

The title compound was prepared from 4'-methoxy-biphenyl-4-carboxylic acid (prepared from 4-methoxybiphenyl using Methods 4 and 5) and 1,4-butanediol using Method 2. Purification by column chromatography (ethyl acetate:light petroleum 1:1) gave the title compound as a white powder (yield 45%). $\delta_C$ (CDCl$_3$, 62.9 MHz): 25.3, 29.3, 55.4, 62.3, 64.8, 114.4, 126.5, 128.4, 130.1, 132.4, 145.2, 159.8 and 166.7. $\delta_H$ (CDCl$_3$, 250 MHz): 1.60 (1H, s, OH), 1.76 (2H, m), 1.85 (2H, m), 3.73 (2H, t, J 6.4), 3.85 (3H, s, OMe), 4.37 (2H, t, J 6.4), 6.98 (2H, d, J 8.8), 7.56 (2H, d, J 8.8), 7.61 (2H, d, J 8.2) and 8.06 (2H, d, J 8.5).

Example 35

1,4-Butanediol mono(2'-nitro-biphenyl-4-carboxylic acid)Ester (ABD-0098) (2-NO$_2$BP)

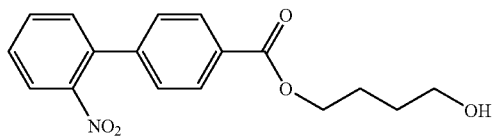

The title compound was prepared from 2'-nitro-biphenyl-4-carboxylic acid (prepared from 2-nitro-biphenyl using Methods 4 and 5) and 1,4-butanediol using Method 2. Purification by column chromatography (ethyl acetate:light petroleum, 1:1) gave the title compound as a pale yellow oil (yield 15%). $\delta_C$ (CDCl$_3$, 62.9 MHz): 25.3, 29.2, 62.4, 65.0, 124.4, 128.0, 128.9, 129.9, 130.1, 131.8, 132.7, 135.6, 142.2, 149.0 and 166.2. $\delta_H$ (CDCl$_3$, 250 MHz): 1.62 (1H, s, OH), 1.76 (2H, m), 1.85 (2H, m), 3.73 (2H, t, J 6.4), 4.38 (2H, t, J 6.4), 7.37 (2H, d, J 8.5), 7.41 (1H, dd, J 7.9, 1.5), 7.52 (1H, J 7.9, 1.5), 7.64 (1H, td, J7.6, 1.2), 7.91 (1H, d, 8.2) and 8.10 (2H, d, J 8.5).

Example 36

1,4-Butanediol mono(2'-fluoro-biphenyl-4-carboxylic acid)Ester (ABD-0099) (2-FBP)

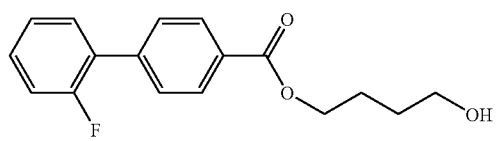

The title compound was prepared from 2'-fluoro-biphenyl-4-carboxylic acid (prepared from 2-fluorobiphenyl using Methods 4 and 5) and 1,4-butanediol using Method 2. Purification by column chromatography (ethyl acetate:light petroleum, 1:1) gave the product as a clear oil (yield 25%). $\delta_C$ (CDCl$_3$, 62.9 MHz): 25.3, 29.2, 62.4, 64.9, 116.3 (d, J23.4), 124.5, (d, J2.9), 128.0 (d, J 13.7), 129.0 (d, J 2.0), 129.4, 129.7, 129.8 (d, J 13.7), 130.6 (d, J 2.0), 140.4, 159.6 (d, J 249.0) and 166.6. $\delta_H$(CDCl$_3$): 1.67 (1H, s, OH), 1.76 (2H, m), 1.88 (2H, m), 3.73 (2H, t, J 6.4), 4.38 (2H, t, J 6.4), 7.16 (1H, m), 7.24 (1H, dd J 8.8, 1.2), 7.33 (1H, m), 7.44 (1H, dt, J 7.6, 1.8) 7.61 (2H, dd, J 8.5, 1.8) and 8.10 (2H, d, J 8.5).

Example 37

1,4-Butandiol mono(4'-fluoro-biphenyl-4-carboxylic acid)Ester (ABD-0100) (4-FBP)

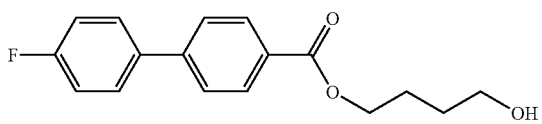

The title compound was prepared from 4'-fluoro-biphenyl-4-carboxylic acid (prepared from 4-fluorobiphenyl using Methods 4 and 5) and 1,4-butanediol using Method 2. Purification by column chromatography (ethyl acetate:light petroleum, 1:1) gave the title compound as a white solid (yield 50%). $\delta_C$ (CDCl$_3$, 62.9 MHz): 25.3, 29.2, 62.4, 64.9, 115.9 (d, J22.5), 126.9, 128.9 (d, J8.8), 129.1, 130.2, 136.1 (d, J2.9), 144.6, 163.0 (d, J 248.0) and 166.6. $\delta_H$ (CDCl$_3$, 250 MHz): 1.58 (1H, s, OH), 1.74 (2H, m), 1.86 (2H, m), 3.74 (2H, t, J 6.4), 4.38 (2H, t, J 6.4), 7.14 (2H, t, J 8.8), 7.56 (2H, d, J 8.8), 7.59 (2H, dd, J 8.2) and 8.08 (2H, d, J 8.5).

Example 38

1,4-Butanediol mono(4'-bromo-biphenyl-4-carboxylic acid)Ester (ABD-0102) (4-BrBP)

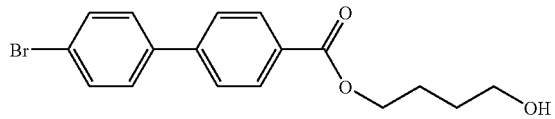

The title compound was prepared from 4'-bromo-biphenyl-4-carboxylic acid (prepared from 4-bromobiphenyl using Methods 4 and 5) and 1,4-butanediol using Method 2. Purification by column chromatography (ethyl acetate:light petroleum, 1:1) gave the title compound as a white solid (yield 30%). $\delta_C$ (DMSO, 62.9 MHz): 25.3, 29.3, 62.4, 64.9, 122.6, 126.9, 128.9, 129.4, 130.2, 132.1, 138.0, 144.4 and 166.4.

Example 39

1,4-Butandiol mono(triphenylacetic acid)Ester (ABD-0028) (4T)

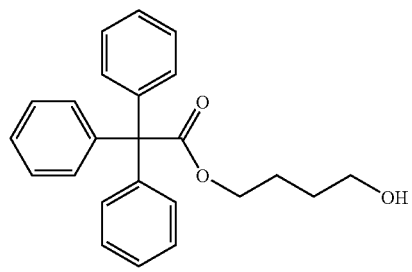

The title compound was prepared from triphenylacetyl chloride (prepared by from triphenylacetic acid using Method 8) and 1,4-butanediol using Method 1, to give the title compound as a white powder (yield 45%). $\delta_C$ (CDCl$_3$, 62.9 MHz): 24.8, 29.0, 62.2, 65.5, 67.6, 126.9, 127.8, 130.3, 143.0 and 173.7.

Example 40

1,5-Pentandiol mono(triphenylacetic acid)Ester (ABD-0030) (5T)

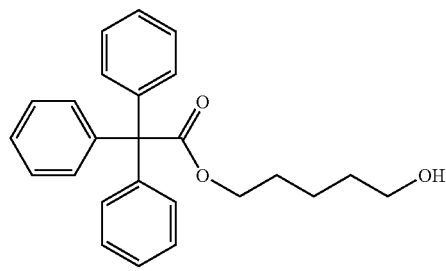

The title compound was prepared from triphenylacetyl chloride (prepared by from triphenylacetic acid using Method 8) and 1,5-pentanediol using Method 1, to give the title compound as a white powder (yield 35%). $\delta_C$ (CDCl$_3$, 62.9 MHz): 22.1, 28.1, 32.1, 62.6, 65.6, 67.6, 126.9, 127.7, 130.3, 143.0 and 173.7.

Example 41

1,6-Hexandiol mono(triphenylacetic acid)Ester (ABD-0031) (6T)

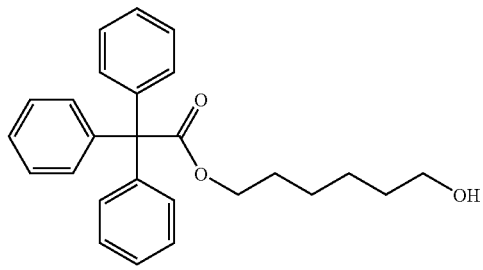

The title compound was prepared from triphenylacetyl chloride (prepared by from triphenylacetic acid using Method 8) and 1,6-Hexanediol using Method 1, to give the title compound as a white powder (yield 35%). $\delta_C$ (CDCl$_3$, 62.9 MHz): 25.2, 25.6, 28.3, 32.5, 62.8, 65.6, 67.6, 126.9, 127.7, 130.3, 143.0 and 173.7.

Example 42

1,3-Propanediol mono(biphenyl-4-yl-acetic acid) Ester (ABD-0041) (3BPA)

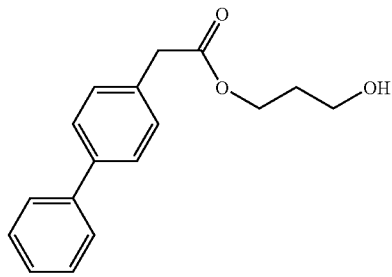

The title compound was prepared from biphenyl-4-yl-acetic acid and 1,3-propanediol using Method 2 to give a white solid (yield 75%). $\delta_C$ (CDCl$_3$, 62.9 MHz): 31.7, 41.1, 59.1, 62.0, 127.1, 127.4, 128.8, 129.7, 133.0, 140.2, 140.8 and 172.1.

Example 43

1,4-Butanediol mono(biphenyl-4-yl-acetic acid)Ester (ABD-0042) (4BPA)

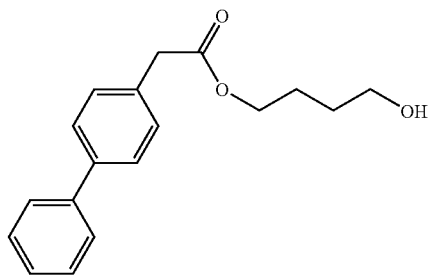

The title compound was prepared from biphenyl-4-yl-acetic acid and 1,4-butanediol using Method 2 to give a white solid (yield 80%). $\delta_C$ (CDCl$_3$, 62.9 MHz): 25.1, 29.1, 41.1, 62.3, 64.8, 127.1, 127.4, 128.8, 129.7, 133.1, 140.1, 140.8 and 171.8. m/z (Found M, 284. C$_{18}$H$_{20}$O$_3$ requires 284).

Example 44

1,5-Pentanediol mono(biphenyl-4-yl-acetic acid) Ester (ABD-0043) (5BPA)

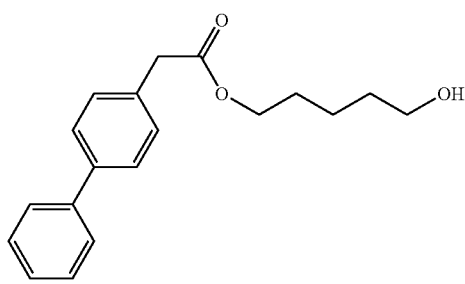

The title compound was prepared from biphenyl-4-yl-acetic acid and 1,5-pentanediol using Method 2 to give a white solid (yield 75%). $\delta_C$ (CDCl$_3$, 62.9 MHz): 22.2, 28.4, 32.3, 41.1, 62.6, 65.0, 127.1, 127.3, 128.8, 129.7, 133.2, 140.1, 140.8 and 171.8.

Example 45

1,6-Hexanediol mono(biphenyl-4-yl-acetic acid) Ester (ABD-0044) (6BPA)

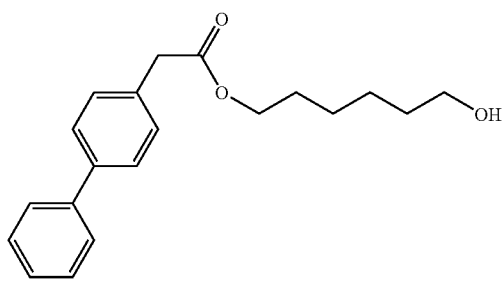

The title compound was prepared from biphenyl-4-yl-acetic acid and 1,6-hexanediol using Method 2 to give a white solid (yield 70%). $\delta_C$ (CDCl$_3$, 62.9 MHz): 25.4, 25.7, 28.6, 32.6, 41.1, 62.8, 65.0, 127.1, 127.3, 128.8, 129.7, 133.2, 140.0, 140.8 and 171.8.

Example 46

1,4-Butanediol mono(naphth-1-yl-acetic acid)Ester (ABD-0032) (4N)

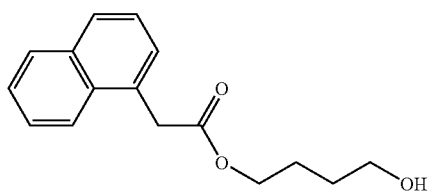

The title compound was prepared from naphth-1-yl acetic acid and 1,4-butanediol using Method 2, to give a clear oil (yield 70%). $\delta_C$ (CDCl$_3$): 25.0, 29.0, 39.3, 62.1, 64.8, 123.8, 125.6, 125.8, 126.4, 128.1, 128.1, 128.9, 130.7, 132.1, 133.8 and 171.8.

Example 47

1,4-Butanediol mono(homoveratric acid)Ester (ABD-0033) (4H)

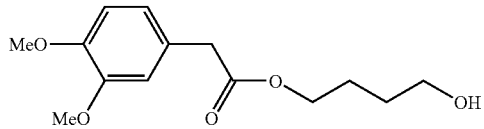

The title compound was prepared from homoveratric acid and 1,4-butanediol using Method 2 to give a clear oil (yield 90%). $\delta_C$ (CDCl$_3$, 62.9 MHz): 25.1, 29.0, 41.0, 55.9, 62.2, 64.7, 111.2, 112.4, 121.4, 126.5, 148.1, 148.9 and 172.0.

Example 48

Butyl [2-(4-isobutylphenyl)Propionic acid] ester (ABD-0035) (BuI)

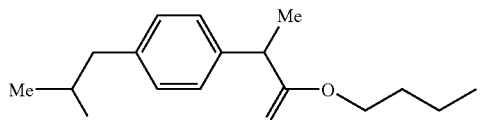

The title compound was prepared from ibuprofen and butanol using Method 2 to give a clear oil (yield 85%). $\delta_C$ (CDCl$_3$, 62.9 MHz): 13.7, 18.5, 19.0, 22.4, 30.2, 30.6, 45.1, 45.2, 64.6, 127.2, 129.3, 137.9, 140.5 and 174.9.

Example 49

Butyl (biphenyl-4-yl-acetic acid) ester (ABD-0040) (BuBPA)

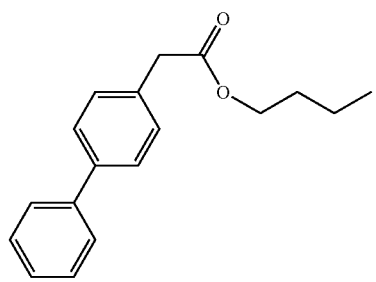

The title compound was prepared from biphenylacetic acid and butanol using Method 2 to give a clear oil (yield 70%). $\delta_C$ (CDCl$_3$, 62.9 MHz): 13.8, 19.1, 30.7, 41.1, 64.9, 127.1, 127.3, 128.8, 129.7, 133.3, 140.0, 140.9 and 171.7.

Example 50

Butyl (biphenyl-4-carboxylic acid) ester (ABD-0053) (BUBP)

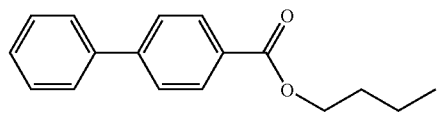

The title compound was prepared from biphenyl-4-carbonyl chloride and butanol using Method 1 to give a white solid (yield 85%). $\delta_C$ (CDCl$_3$, 62.9 MHz) 13.8, 19.3, 30.9, 64.9, 127.1, 127.3, 128.1, 129.0, 130.1, 140.1, 145.6 and 166.6; m/z (Found M, 254. C$_{17}$H$_{18}$O$_2$ requires 254).

Example 51

Pentyl (biphenyl-4-carboxylic acid) ester (ABD-0090) (PBP)

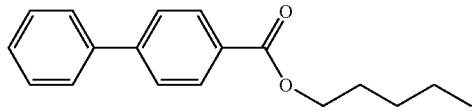

The title compound was prepared from biphenyl-4-carbonyl chloride and pentanol using Method 1 to give a clear oil (yield 85%). $\delta_C$ (CDCl$_3$, 62.9 MHz): 14.1, 22.4, 28.3, 28.5, 65.2, 127.1, 127.3, 128.1, 128.9, 129.3, 130.1, 140.1, 145.6 and 166.6.

Example 52

4-Methoxybutyl (biphenyl-4-carboxylic acid) ester (ABD-0050) (4BP-OMe)

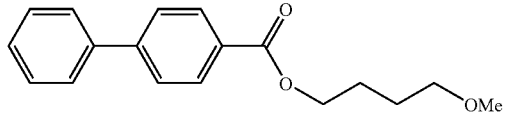

ABD-0056 (7 mmol) was dissolved in acetone (20 ml) containing powdered NaOH (1.5 g). Dimethyl sulphate (1.5 g, 12 mmol) was added dropwise and the mixture stirred overnight to give a slurry. The slurry was poured into water (200 ml) and washed with methylene chloride (100 ml). The organic phase was washed with water until it became clear. The organic phase was dried over Na$_2$SO$_4$, the solvent evaporated and the title compound obtained by column chromatography (light petroleum:ethyl acetate, 1:1, followed by a repeat using light petroleum:ethyl acetate, 5:1) as a yellow oil (yield 50%). $\delta_C$ (CDCl$_3$, 62.9 MHz): 25.6, 26.3, 58.7, 64.8, 72.2, 127.1, 127.3, 128.2, 129.0, 129.2, 130.1, 140.0, 145.6 and 166.6.

Example 53

4-Bromobutyl (biphenyl-4-carboxylic acid) ester (ABD-0086) (4BP-Br)

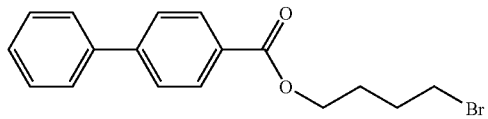

The title compound was prepared from biphenyl-4-carbonyl chloride and 4-bromobutanol (prepared using Method 9) using Method 1, to give the title compound as a pale brown oil (yield 20%). $\delta_C$ (CDCl$_3$, 62.9 MHz): 26.2, 29.3, 44.6, 64.2, 127.1, 127.3, 128.2, 129.0, 130.1, 140.0, 145.7 and 166.5.

Example 54

4-Nitrooxybutyl (biphenyl-4-carboxylic acid) ester (ABD-0087) (4BP-NO$_2$)

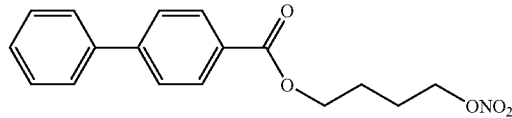

The title compound was prepared from ABD-0086 (5 mmol) by stirring with AgNO$_3$ (25 mmol) in acetonitrile (50 ml) for 24 hours. The mixture was filtered, the filtrate evaporated and purified by column chromatography (light petroleum:ethyl acetate, 4:1) to give the title compound as pale yellow oil (yield 55%). $\delta_C$ (CDCl$_3$, 62.9 MHz): 23.8, 25.2, 64.0, 72.7, 127.1, 127.3, 128.2, 128.8, 129.0, 130.1, 139.9, 145.8 and 166.4.

Example 55

4-Nitrooxybutyl (2,2',4'-trinitro-biphenyl-4-carboxylic acid) ester (ABD-0088) (4xNO$_2$-BP)

ABD-0056 (10 mmol) was stirred in nitric acid (50 ml) and the temperature slowly increased to 80° C. for 5 hours. The mixture was poured into water (250 ml) and extracted with methylene chloride (100 ml). The organic phase was washed with water, saturated NaHCO$_3$ and water, dried with Na$_2$SO$_4$ and evaporated. Column chromatography (ethyl acetate:light petroleum, 1:1) gave the title compound as a thick yellow oil (yield 20%). $\delta_C$ (CDCl$_3$, 62.9 MHz): 23.7, 25.1, 65.3, 72.4, 120.6, 126.2, 127.9, 130.7, 131.9, 132.4, 134.5, 136.5, 139.7, 146.7, 147.0, 148.0 and 163.7. $\delta_H$ (CDCl$_3$, 250 MHz): 1.95 (4H, m), 4.47 (2H, m), 4.54 (2H, m), 7.40 (1H, d, J7.9), 7.54 (1H, d, J8.5), 8.38 (1H, dd, J7.9, 1.8), 8.55 (1H, dd, J8.5, 2.4), 8.90 (1H, d, J 1.5) and 9.10 (1H, d, J2.4).

Biological Studies

Initial screening of candidate compounds was performed using viability assays, on cultures of the macrophage cell line J774, which have been used before as a model system for osteoclast survival (see, e.g., Luckman et al., 1998). The assay is based on the survival of the J774 macrophage cell line; macrophages are closely related to osteoclasts, and contain similar high levels of esterase activity.

MTT Macrophage J774 Viability Assay

J774 cells were plated at 10$^4$ cells per well in 150 µL αMEM (α Modified Eagle Medium) in 96-well plates and grown overnight. The next day, compounds were added to the cultures, and culture was continued for another 72 hours. At the end of the culture period cell survival was determined using the tetrazolium dye-based MTT assay as previously described (see, e.g., MacPherson et al., 1999).

MTT (3-(4,5-dimethylthiazol-2-yl)-2,5-diphenyl tetrazolium bromide) has an orange colour and is soluble in the medium used for cell culture. The mitochondrial enzyme succinate dehydrogenase acts upon MTT in living cells to produce the insoluble purple coloured formazan. The amount of formazan produced, as measured by UV/visible spectroscopy, is proportional to the number of viable cells.

Briefly, MTT (5 mg/ml MTT in αMEM) was added to each well (1:10 v/v, 15 μL) and the cells incubated for 4 hours. The medium was carefully removed using a needle without dislodging the crystal layer. 100 μL acidified isopropanol (4 M HCl 1:100 v/v in isopropanol) was added to each well and the purple crystals allowed to dissolve. The absorbance was measured in a plate reader at 540 nm, with 690 nm as reference. The controls were a deep purple colour, indicating a high number of live cells. The results for each test compound were expressed as a % of the average control value.

Addition of Compounds. All of the compounds studied were made up as 100 mM solutions in DMSO. These stock solutions were then diluted 100× in culture medium. From these 1 mM solutions, convenient quantities (3-15 μL) were added directly to the wells so as to give the desired final compound concentration.

Alamar Blue Macrophage J774 Viability Assay

J774 cells were plated at $10^4$ cells per well in 150 μL αMEM (α Modified Eagle Medium) in 96-well plates and grown overnight. The next day, compounds were added to the cultures, and culture was continued for another 72 hours. At the end of the culture period cell survival was determined using an Alamar Blue assay as previously described (see, e.g., Nociari et al., 1998).

Alamar Blue is an oxidation-reduction sensitive indicator. The dye itself is in the oxidised state, which is blue and non-fluorescent. The dye can accept electrons from reducing species, such as NADPH and FADH, to form a reduced dye species, which is red and fluorescent. Thus the transformation from oxidised form to reduced form can be measured by fluorimetric or colourimetric means. For fluorescence measurements, 530-560 nm excitation and 590 nm emission wavelengths are typically used. For colourimetric measurements, absorbance is measured at 570 nm (reduced form) and 600 nm (oxidised form) and a simple calculation performed to determine the relative quantities of the two species.

A high ratio of the reducing species, NADPH and FADH, to the corresponding oxidised species, NADP and FAD, is an indicator that cells are proliferating and viable. A low ratio indicates cells that are quiescent or non-viable.

Briefly, Alamar Blue (Biosource International) was added undiluted to the each well (1:10 v/v, 15 μL). The plate was incubated at 37° C. for 3-4 hours and the fluorescence was measured at 570 nm, with a 25 nm bandwidth. A high reading indicated cells with normal viability, and a low reading indicates cells that have been damaged and are no longer proliferating normally. The controls gave a high fluorescence reading, indicating a high number of live, healthy cells. A potent test compound gave a low fluorescence reading. The average results for each test compound (n=5) were expressed as a % of the average control value.

Addition of Compounds. All of the compounds studied were made up as 100 mM solutions in DMSO. These stock solutions were then diluted 100 or 1000× in culture medium (αMEM). From these 1 mM or 100 μM solutions, convenient quantities (3-15 μL) were added directly to the wells so as to give the desired final compound concentration.

This assay offers numerous advantages over other assays, including MTT assays: it permits a higher throughput; it is more sensitive; it is non-damaging to the cells; it is faster; it generally gives an identical result to MTT assay. A comparison is shown in FIG. 1, which is a graph of the macrophage J774 viability, as measured by the MTT and Alamar Blue macrophage J774 viability assays, expressed as % of control, after 72 hours exposure to ABD-0028 and ABD-0042, as a function of concentration of compound. Only one compound (ABD-0056) showed significant difference between the MTT and Alamar Blue assays.

Additional Studies

Some compounds were further evaluated in two model systems of true osteoclasts: (a) the murine co-culture system, and (b) the rabbit osteoclast culture system.

Murine Co-Culture System

The first model system, the murine co-culture system, studies the formation of osteoclasts from precursors present in the bone marrow. The number of osteoclasts and the amount of dentine resorption was measured.

Osteoclast formation and activity was studied using an adaptation (see, e.g., van't Hof & Ralston, 1997) of the osteoblast-bone marrow co-culture assay originally described by Takahashi et al., 1988.

Co-Culture Methods. Co-culture (see, e.g., Van't Hof et al., 1997) is a method to study the formation of osteoclasts from their precursors. In this assay, osteoblasts were obtained from the calvaria of 2-3 day old neonatal mice. These were plated on dentine, stimulated with 1,25-dihydroxy vitamin $D_3$ to stimulate RANKL and M-CSF expression. Early osteoclast precursors were present in the bone marrow of adult mice. The bone marrow suspension was purified to remove the red blood cells and the remainder cultured on top of the osteoblast layer. The stimulatory factors then allowed the osteoclast precursors to differentiate into mature osteoclasts. At the end of the culture osteoclasts were identified by TRAcP staining and the resorption activity was measured in the same manner as for rabbit osteoclasts.

Although it is possible to generate osteoclasts from bone marrow cells alone by treating the cultures with RANKL and M-CSF, the co-culture system is still regarded as one of the most reliable and reproducible available. It is useful for studying the effects of drugs on both osteoclast progenitors and mature osteoclasts.

Preparation of Dentine. The dentine was elephant ivory, preferred to bone because of its uniform surface, which facilitates easy visualisation of resorption pits. It was cut into slices of approximately 200 μm thickness using a Buehler Isomet low speed saw with a diamond wafering blade (series 15 HC). These slices were polished by hand, to a high degree, until one side was shiny. Out of these slices, discs were punched that fit the wells of a 96 well plate, using a paper puncher. Excess residues from the polish were removed by sonication. The discs were then stored in 70% ethanol until required. These discs were then dried and placed shiny side up in the wells of a 96 well plate. Cells were seeded onto the dentine. Following completion of the culture, these dentine slices were carefully removed from the plate and studied under the microscope.

Osteoblast Isolation. Briefly, osteoblasts were isolated from the calvarial bones of 2-day-old mice by sequential collagenase digestion (type I collagenase, Sigma) and cultured in αMEM supplemented with 10% FCS (foetal calf serum) and penicillin and streptomycin at 37° C. in 5% $CO_2$.

More specifically, osteoblasts were obtained from a collagenase digestion of the calvaria (skull bones) of 2-3 day old neo-natal MF1 mice. At this stage in their development these are soft and easily removed. The calvaria from 5-6 mice were carefully dissected and washed in HBSS (Hank's balanced saline solution). The calvaria were placed in a 15 ml tube and shaken at 37° C. in 4 ml collagenase (10 mg/ml) for 10 minutes. This removes the excess unwanted tissue. The liquid was disposed of and a further 4 ml collagenase (10 mg/ml) added to the tube. The calvaria were then digested for a further 30 minutes. After this the supernatant (F1) was removed and retained. The calvaria were washed with a 2×4 ml PBS and this was added to F1. 4 ml EDTA (ethylene diamine tetraacetic acid) (4 mM in PBS) was then added to complex the calcium and allow further extraction of osteoblasts. This was shaken for 10 minutes at 37° C. The supernatant was removed and retained (F2). The calvaria were again washed with 2×4 ml HBSS and this was added to F2. The final 4 ml of collagenase (10 mg/ml) was added to the tube and this was again shaken at 37° C. for 30 minutes. Whilst this was being done, F1 and F2 were spun down at 300 g for 3 minutes, brake 3. The pellets were re-suspended in 1 ml medium (αMEM supplemented with 10% FCS (foetal calf serum) and penicillin and streptomycin), combined and added to 10 ml medium in two 75 cm² flasks. The liquid from the final collagenase digestion was collected (F3), the calvaria washed and the combined liquid extracts spun down in the centrifuge. The pellet was re-suspended in 1 ml medium and added in equal proportions to the flasks containing F1 and F2. The flasks were left for 4-6 hours at 37° C. and then the medium was changed to remove any non-adherent cells. These flasks may be left for up to 4 days at 37° C., 5% $CO_2$.

Osteoblast Plating. The medium was removed from the flasks and the cells washed with PBS. 2 ml Trypsin was added to the cells and these were incubated at 37° C. for 2 minutes. The flasks usually required gentle agitation to fully loosen the cells. 4 ml medium supplemented with 10% FCS was added to stop the enzymatic action. The cells were removed and the flask washed out with medium. The cell suspension was spun down at 300 g for 3 minutes, the medium removed and the pellet re-suspended in 1 ml medium. The cells were counted and then seeded in a 96 well plated containing dentine slices, at $8 \times 10^3$ cells per well in 100 μl medium containing 1000× dilution of stock 1,25-dihydroxyvitamin $D_3$ (final conc. 10 nM/well) to stimulate the expression of RANKL and cultured overnight.

Isolation of Bone Marrow Cells. Briefly, bone marrow cell populations containing osteoclast precursors were isolated from the long bones of 3-5 month old mice and erythrocytes were removed by Ficoll Hypaque density gradient centrifugation. The resulting bone marrow cells were washed with PBS (phosphate buffered saline) and re-suspended in culture medium.

More specifically, the femurs and tibia were dissected from 2-3 adult MF1 mice 3-6 months old) and the surrounding tissue was removed. The bones were trimmed to allow access to the bone marrow. The marrow was flushed out using a 25G needle and HBSS+10% FCS. A single cell suspension is obtained by repeatedly squeezing the cell suspension through needles of decreasing size (start with 19G, end with 25G). 5 ml Ficoll was added to a 15 ml tube and the cell suspension carefully placed on top of this with the minimum amount of mixing between the layers. The density centrifugation was performed at 600 g, 25 min, brake off. This was sufficient to allow the red blood cells to congregate at the bottom of the tube, fats to remain at the top of the liquid and the desired bone marrow cells to collect at the interface. The cloudy layer from the interface was collected with a pipette, placed in a fresh 15 ml tube and made up to 12 ml with HBSS. The cell suspension was spun down at 300 g for 3 minutes. The pellet was collected and re-suspended in 1 ml medium. The bone marrow cells were counted and then added to the 96 well plate containing the osteoblasts at $2 \times 10^5$ cells/well in 50 μL medium.

Osteoblast Precursor Studies. To investigate the effects of a drug on osteoclast precursors the timetable was as follows:
Day 0—Plate osteoblasts.
Day 1—Plate bone marrow cells
Day 2—Add test compound.
Day 4—100% medium refresh+1,25-dihydroxyvitamin $D_3$(final conc. 10 nm/well)
Day 6—Add IL1 (10 u/ml) and 1,25-dihydroxyvitamin $D_3$ (final conc. 10 nm/well)
Day 10—Fix cells.

Mature Osteoclast Studies. To investigate the effects of a drug on mature osteoclasts the timetable was as follows:
Day 0—Plate osteoblasts.
Day 1—Plate bone marrow cells.
Day 6—50% medium refresh+10 nM IL1 and 1,25-dihydroxyvitamin $D_3$.
Day 7—Add drugs and remove and fix day 7 control slices.
Day 10—Fix cells.

At the conclusion of a study, the cells were fixed in 4% formaldehyde for 10 minutes and washed in PBS. Fixed cells were either stained and kept in 70% ethanol or refrigerated in water or PBS. The 50% medium refresh involved the addition of 150 μL fresh medium containing a 500× dilution of 1,25-dihydroxyvitamin $D_3$ and a 250× dilution of IL1 (interleukin 1). This was left for 15 minutes and then 150 μL medium carefully removed. The medium refresh must be done very carefully, because the confluent layer of osteoblasts can be quite easily disturbed, and detached. This would result in a total absence of osteoclasts. Usually the first osteoclasts and resorption pits appeared on day 6. Reasonable numbers of osteoclasts were present between day 7-10.

At the end of the culture, the osteoclasts were identified by staining for tartrate-resistant acid phosphatase (TRAcP) staining and resorption pit area was quantified by reflected light microscopy as described previously (see, e.g., van't Hof & Ralston, 1997).

TRAcP Staining. Osteoclasts express very high levels of the enzyme tartrate resistant acid phosphatase (TRAcP) and can therefore be easily visualised by staining for this enzyme, for example, by the following method. Two staining solutions, (1) and (2), were made up freshly as follows:
Solution 1. 300 μL Naphthol-AS-BI-phosphate stock.
   1.5 ml Veronal buffer.
   1.8 ml Acetate buffer.
   1.8 ml Acetate buffer with 100 mM tartrate.
Solution 2. 240 μL Pararosaniline.
   240 μL $NaNO_2$ (4% stock solution).

Naphthol-AS-BI-phosphate stock: 10 mg/ml Naphthol-AS-BI-phosphate in dimethylformamide.

Veronal buffer: 1.17 g anhydrous Sodium Acetate; 2.94 g Veronal (sodium barbiturate); dissolved in 100 ml distilled water.

Acetate buffer 0.1 M, pH 5.2: solution (a): 0.82 g Sodium Acetate anhydrous dissolved in 100 ml distilled water; solution (b): 0.6 ml Acetic acid glacial made up to 100 ml with distilled water; pH of solution (a) adjusted to pH 5.2 with solution (b).

Pararosaniline: 1 g Pararosaniline in 20 ml distilled water. 5 ml concentrated hydrochloric acid was added, the solution was heated carefully in a water bath while stirring. The solution was allowed to cool and then filtered.

Solutions (1) and (2) were mixed and filtered to give the staining solution. The PBS from the wells was removed and at least 50 μL of staining solution added.

The cells were incubated at 37° C. for about 45 min, or until the dentine slices appeared sufficiently red. To determine what passes as sufficient it was necessary to remove the dentine slice and check under a light microscope that the osteoclasts were suitably stained. The staining solution was then removed and replaced with 70% ethanol. The dentine-slices-were stored in a refrigerator.

Osteoclast Counting. This was done using a light microscope to determine the number of TRAcP positive multinucleated cells on each dentine slice. The slices were carefully removed from the 96-well plate, avoiding disturbance of the cell layer, and placed on a glass slide. A few drops of 70% ethanol were put on each slice followed by a glass coverslip. Working across the dentine the number of multinucleated, red-stained cells were counted. There were usually a large number of small red mononucleated cells. These were osteoclast precursors and these were not counted. The numbers of osteoclasts on the control slices can range from 300 up to 1000. For each compound or concentration studied, the average of the values for the 5 slices was taken and expressed as a % of the average value for the controls. Any obvious outlying values were ignored. The most common reason for this was when there were no cells of any kind, usually indicating that the osteoblast layer has detached during handling.

Quantification of Resorption Area. After the osteoclasts were stained and counted it was necessary for the dentine slice to be thoroughly cleaned. The slices were rubbed on a suitable surface, a piece of blue roll proved ideal for this purpose. In order to clean the slices properly it may be necessary to wash them in dilute HClO for a few seconds to loosen the cell debris. The resorption pits can be visualised either by staining with dyes such as Toluidine blue or Coomassie blue, by scanning electron microscopy or by reflected light microscopy. Here, reflected light microscopy was used, because it is easy to perform, the slices needed only thorough cleaning and no staining, and the image obtained could be fairly easily quantified using image analysis. Because the slices need to be completely flat for the reflected light microscopy, they were glued glass slides under pressure of a 0.5 kg metal weight. These may then be easily stored. A Zeiss reflected light microscope was used, fitted with a 2.5× lens, wide field c-mount adapter, and Diagnostics Instruments Insight BNV large chip digital camera. This set-up allowed the capture of an entire bone slice in one image at sufficient resolution to identify and measure the resorption pits. The image analysis software package was developed using the Aphelion ActiveX image analysis toolkit from ADCIS (ADCIS SA, Herouville-Saint-Clair, France). The dentine slices appeared as a bright shiny surface littered with dark resorption pits. The software calculated the resorption areas for each slice. When determining the effects of the compounds in co-cultures, it was necessary to use both the values obtained for slices removed at the time when the drugs were added (e.g., Day 7), as well as the controls from the end of the study (e.g., Day 10).

Rabbit Osteoclast Culture System

The second model system was the rabbit osteoclast system, where mature, functional osteoclasts were isolated from the long bones of rabbits and cultured on dentine slices.

Osteoclast Isolation. Osteoclasts were isolated from the long bones of 2-10 day-old rabbits, as described previously (see, e.g., reference Coxon et al., 2000). All 4 limbs were removed from the rabbits and placed in ice-cold PBS. Soft tissue and cartilage were removed and the bones transferred into fresh PBS. The bones were minced in aMEM (without FCS), using a scalpel. All the medium and fragments were transferred to a 50 ml tube, vortexed for 3×10 seconds and left to stand for 1 minute. The supernatant was removed and made up to 50 ml/rabbit with medium and FCS so as to give a final concentration of 10% FCS.

Osteoclast Plating. The cells were plated onto dentine slices in a 96 well plate, at 100 μL/well (medium: αMEM supplemented with 10% FCS and penicillin and streptomycin) and left for 4 hours to allow adherence to the dentine. After this period the medium was removed, and with it the non-adherent cells. Fresh medium was then added. The remaining population was highly enriched in osteoclasts.

Culturing. At this point, test compounds to be studied were added and the cells cultured at 37° C. in 5% $CO_2$ for 48 hours. At the end of the culture, the osteoclasts were identified by staining for tartrate-resistant acid phosphatase (TRAcP) staining. A good number of osteoclasts in the controls was 100-200.

The results were expressed as a % of the average number of osteoclasts seen in the controls. The resorption pit area was quantified by reflected light microscopy as described previously (see, e.g., van't Hof & Ralston, 1997) and again the results expressed as a % of the control values.

Biological Data 1,4-butanediol was tested for its ability to inhibit osteoclast formation and activity in the murine co-culture system; it had no detected effect on the osteoclasts.

A number of monoesters of alkane diols were prepared, and $IC_{50}$ values for macrophage J774 viability assays for many of these are summarised in Table 1. The most potent compounds, ABD-0056 (4BP) and ABD-0085 (10F), are almost an order of magnitude more active than any of the other compounds studied.

TABLE 1

| | | | $IC_{50}$ (μM) | |
| # | Compound | | MTT | Alamar Blue |
| --- | --- | --- | --- | --- |
| 1 | ABD-0006 | 4A | >100 | — |
| 2 | ABD-0007 | 4Bu | >100 | — |
| 3 | ABD-0008 | 4MB | >100 | — |
| 4 | ABD-0009 | 4B | >100 | — |
| 5 | ABD-0014 | 4P | >100 | — |
| 6 | ABD-0017 | 6P | >100 | — |
| 7 | ABD-0019 | 4C | >100 | — |
| 8 | ABD-0028 | 4T | 20 | 30 |
| 9 | ABD-0030 | 5T | 40 | — |
| 10 | ABD-0031 | 6T | 40 | — |
| 11 | ABD-0032 | 4N | >100 | — |
| 12 | ABD-0033 | 4H | >100 | — |
| 13 | ABD-0034 | 4PT | >100 | — |
| 14 | ABD-0035 | BuI | 72 | — |
| 15 | ABD-0036 | 4I | 52 | — |
| 16 | ABD-0037 | 3I | 72 | — |
| 17 | ABD-0038 | 5I | 68 | — |
| 18 | ABD-0039 | 6I | 72 | — |
| 19 | ABD-0040 | BuBPA | >100 | — |
| 20 | ABD-0041 | 3BPA | 75 | — |
| 21 | ABD-0042 | 4BPA | 45 | 45 |
| 22 | ABD-0043 | 5BPA | >100 | — |
| 23 | ABD-0044 | 6BPA | 28 | — |
| 24 | ABD-0049 | 4BP-Ac | — | 50 |
| 25 | ABD-0050 | 4BP-Ome | — | >100 |
| 26 | ABD-0053 | BuBP | >100 | — |
| 27 | ABD-0054 | 6BP | 35 | — |
| 28 | ABD-0055 | 5BP | 65 | — |
| 29 | ABD-0056 | 4BP | 3.5 | 18 |
| 30 | ABD-0057 | 3BP | >100 | — |
| 31 | ABD-0059 | 4BPX | >100 | — |
| 32 | ABD-0069 | 4IB | — | 90 |
| 33 | ABD-0070 | Me-4BP | — | >100 |
| 34 | ABD-0072 | HO-4BP | — | 45 |
| 35 | ABD-0077 | 5F | — | 25 |

TABLE 1-continued

| # | Compound | MTT | Alamar Blue |
|---|---|---|---|
| | | IC$_{50}$ (µM) | |
| 36 | ABD-0085 | 10F | — | 4 |
| 37 | ABD-0086 | 4BP-Br | — | >100 |
| 38 | ABD-0087 | 4BP-NO$_2$ | — | 30 |
| 39 | ABD-0088 | 4xNO$_2$-BP | — | 35 |
| 40 | ABD-0089 | Xyl | — | 9 |
| 41 | ABD-0090 | PBP | — | 45 |
| 42 | ABD-0094 | Et-4BP | — | >100 |
| 43 | ABD-0095 | BP-4F | — | 40 |
| 44 | ABD-0096 | DBP-4F | — | — |
| 45 | ABD-0097 | 4OMe-BP | — | >100 |
| 46 | ABD-0098 | 2NO$_2$-BP | — | 17 |
| 47 | ABD-0099 | 2F-BP | — | 14 |
| 48 | ABD-0100 | 4F-BP | — | 14 |
| 49 | ABD-0102 | 4Br-BP | — | 14 |
| 50 | ABD-0106 | 2,3,6-FB | — | >100 |
| 51 | ABD-0107 | 3,4-FB | — | >100 |
| 52 | ABD-0108 | 2,3,4-FB | — | >100 |
| 53 | ABD-0109 | 2,4,5-FB | — | >100 |
| 54 | ABD-0110 | 2,4-FB | — | >100 |
| 55 | ABD-0111 | D2,4-FB | — | >100 |

Some compounds were also evaluated using the murine co-culture system and rabbit osteoclasts.

Figure 2:
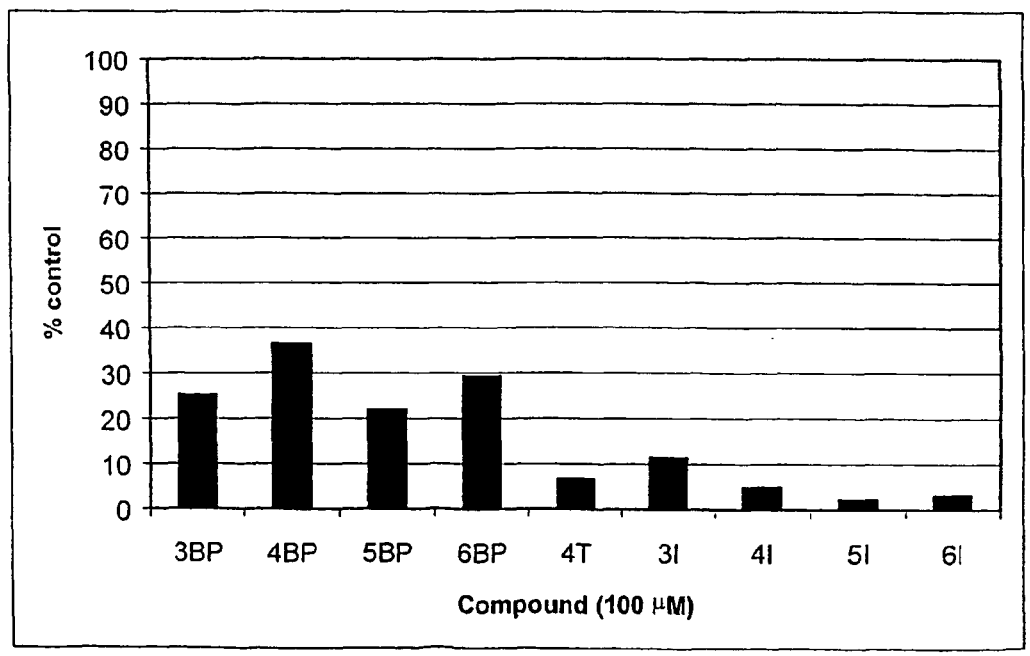
FIG. 2 is a bar graph showing the number of osteoclasts, expressed as a % of control value, after three days exposure to compound, for the murine co-culture system, for several examples of biphenylcarboxy (BP), trityl (T), and ibuprofenyl (I) compounds: ABD-0057 (3BP), ABD-0056 (4BP), ABD-0055 (5BP), ABD-0054 (6BP), ABD-0028 (4T), ABD-0037 (31), ABD-0036 (41), ABD-0038 (51), and ABD-0039 (61). All compounds were tested at 100 µM concentration. Each value represents an average of 3 experiments, each of which had 5 data points.

At a concentration of 100 µM, all of the biphenylcarboxy (BP), trityl (T), and ibuprofenyl (I) compounds tested were found to be potent inhibitors of osteoclast formation and activity in the murine co-culture system, as illustrated in FIG. 2.

Figure 3:
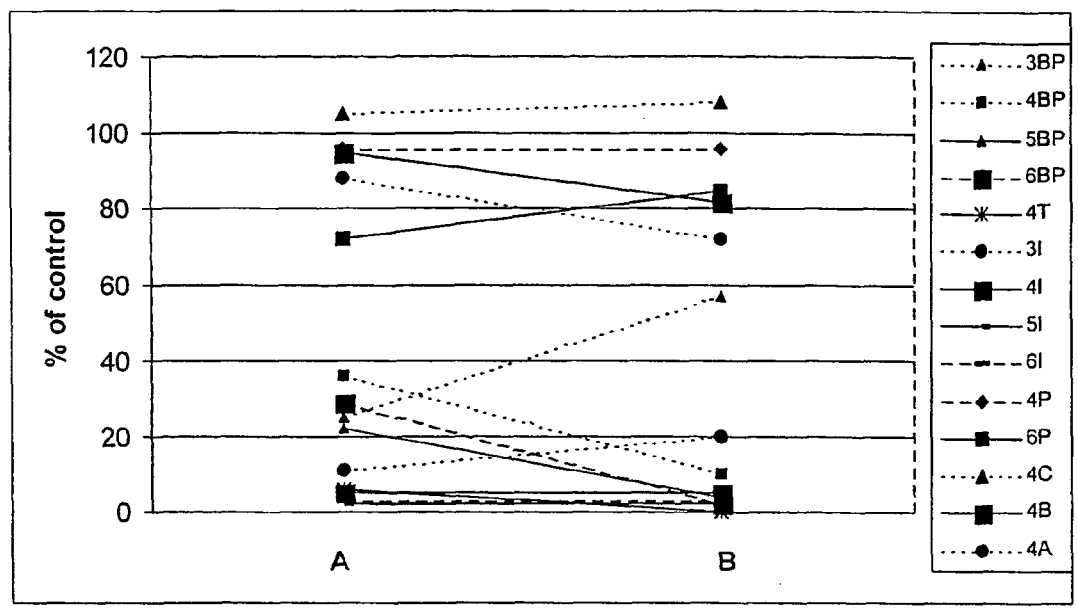
FIG. 3 is a graph showing the effects of compounds on osteoclast and J774 survival, for both the murine co-culture system (A) and the MTT macrophage J774 viability assay (B), for several examples of biphenylcarboxy (BP), trityl (T), and ibuprofenyl (I) compounds, and some others. For co-culture (A), the graph shows number of osteoclasts, expressed as a % of control value. For macrophages (B), the graph shows viability as measured by the MTT assay, expressed as % of control. All compounds were tested at 100 µM concentration.

FIG. 3 shows that at 100 µM, survival of macrophage J774 cells is comparable to that of genuine osteoclasts. All compounds which were effective in macrophages were also effective in the murine co-culture, and no compounds were found to be solely effective in one system. Only one compound, ABD-0057 (3BP), showed a significant difference in response between the two systems.

Some compounds were also evaluated over a range of concentrations, using the MTT and Alamar Blue macrophage J774 viability assays.

Figure 4:
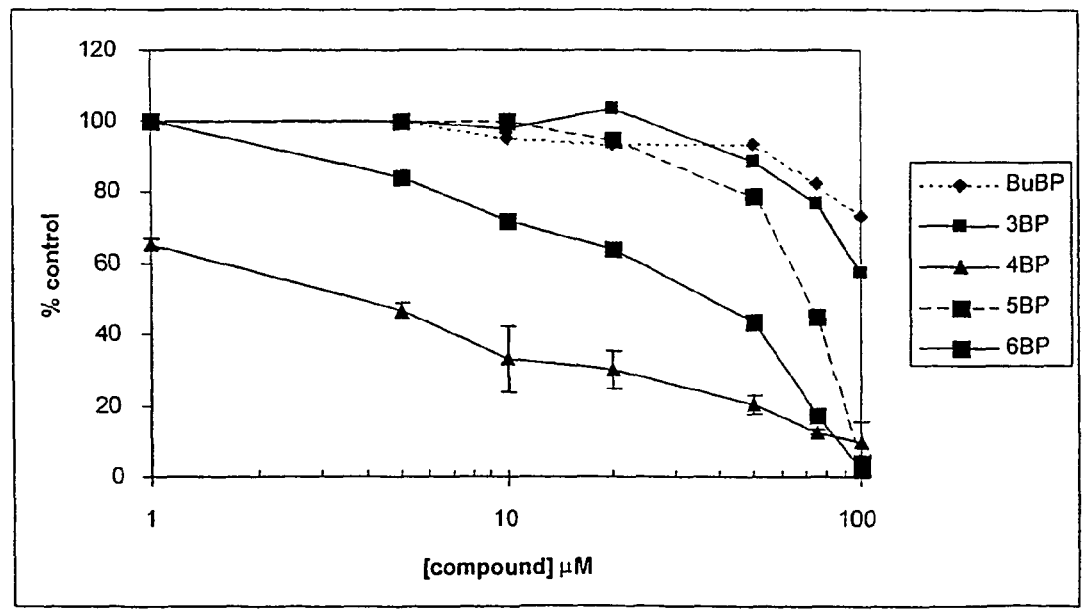
FIG. 4 is a graph of macrophage viability, as measured by the MTT macrophage J774 viability assay, expressed as % of control, after 24 hour exposure to compound, for several examples of biphenylcarboxy (BP) compounds: ABD-0053 (BuBP), ABD-0057 (38P), ABD-0056 (4BP), ABD-0055 (5BP), ABD-0054 (6BP). Unless shown, error bars are less than 20%.

The results for the biphenylcarboxy compounds, ABD-0053 (BuBP), ABD-0057 (3BP), ABD-0056 (4BP), ABD-0055 (5BP), and ABD-0054 (6BP), using the MTT macrophage J774 viability assay, are illustrated in FIG. 4.

Compound ABD-0056 (4BP) is the most active of the BP compounds, with an IC$_{50}$ of 3.5 µM. This is substantially lower than any of the other BP derivatives, or indeed any other derivatives yet encountered (other than ABD-0085 (10F)). The next most active BP compound is ABD-0054 (6BP). The butanol compound ABD-0053 (BuBP) (which lacks a terminal hydroxyl group) showed very little activity, suggesting that the biphenylcarboxy (BP) group itself is not toxic. The biphenylcarboxylic acid was not active.

Figure 5:
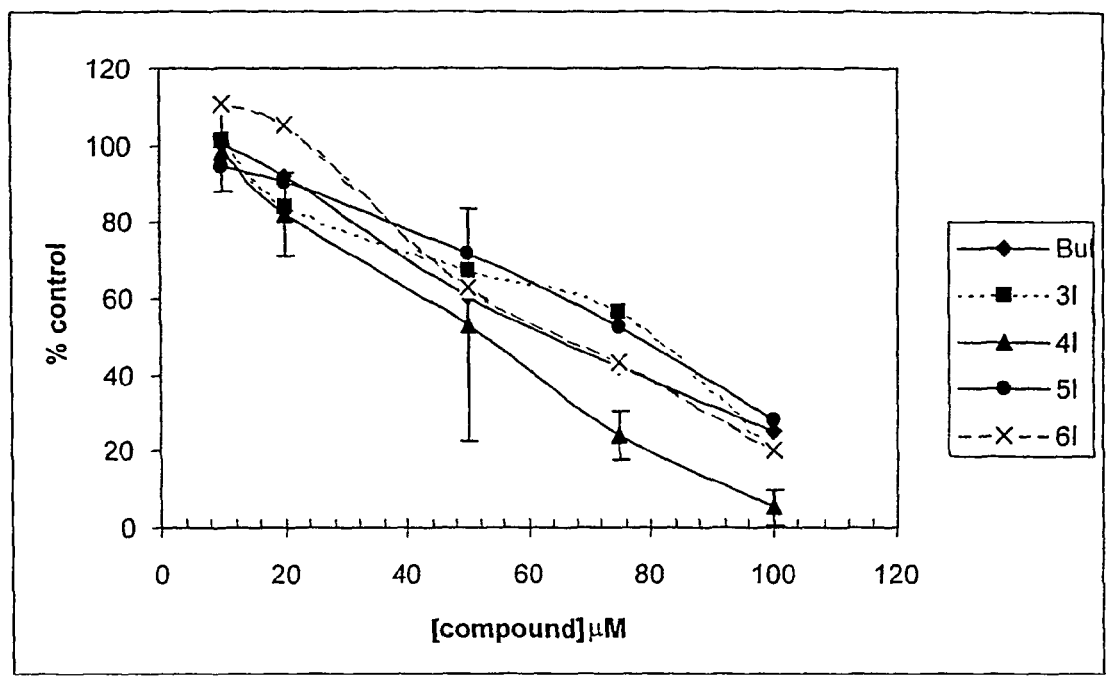
FIG. 5 is a graph of macrophage viability, as measured by the MTT macrophage J774 viability assay, expressed as % of control, after 24 hour exposure to compound, for several examples of ibuprofenyl (I) compounds: ABD-0035 (BuI), ABD-0037 (31), ABD-0036 (41), ABD-0038 (51), ABD-0039 (61). Unless shown, error bars are less than 20%.

The results for the ibuprofenyl (I) compounds, ABD-0035 (BuI), ABD-0037 (3I), ABD-0036 (4I), ABD-0038 (5I), and ABD-0039 (6I), using the MTT macrophage J774 viability assay, are illustrated in FIG. 5.

Again the butanediol derivative, compound ABD-0036 (4I), was the most active, but by a less significant margin. But note that ibuprofen itself may be having a significant effect on the proliferation and survival of the macrophages.

Figure 6:
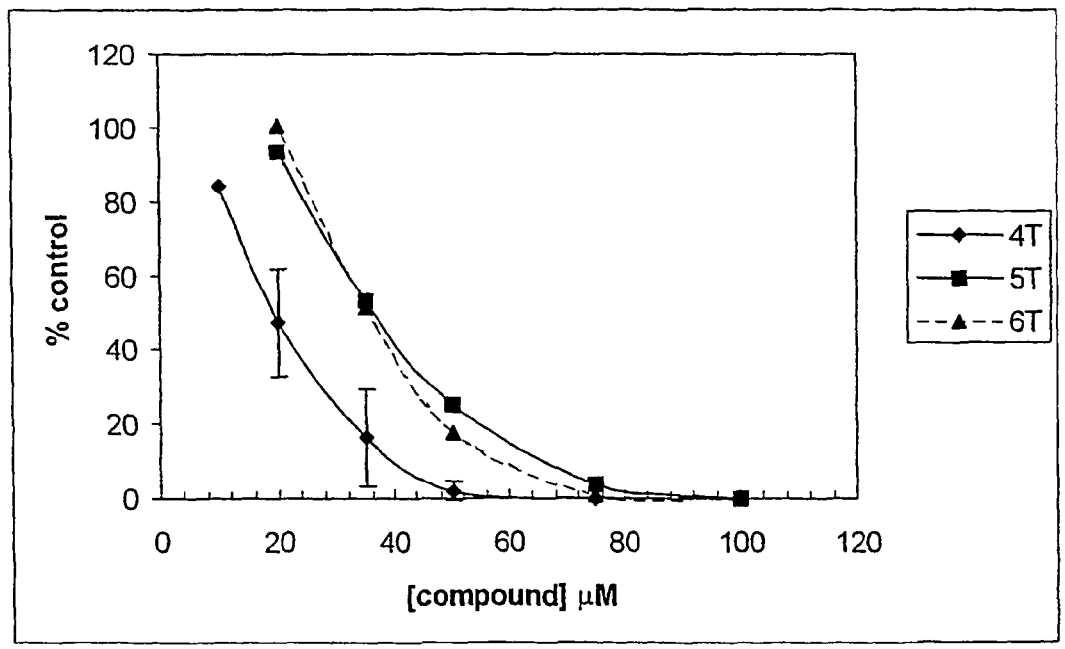
FIG. 6 is a graph of macrophage viability, as measured by the MTT macrophage J774 viability assay, expressed as % of control, after 24 hour exposure to compound, for several examples of trityl (T) compounds: ABD-0028 (4T), ABD-0030 (5T), ABD-0031 (6T). Unless shown, error bars are less than 20%.

The results for various trityl compounds, ABD-0028 (4T), ABD-0030 (5T), and ABD-0031 (6T), using the MTT macrophage J774 viability assay, are illustrated n FIG. 6.

All of the trityl compounds were found to inhibit macrophage function to a high degree, suggesting the high toxicity of the triphenylacetyl group. The butanediol derivative, compound ABD-0028 (4T), is more potent than compound ABD-0030 (5T) and compound ABD-0031 (6T).

Figure 7:
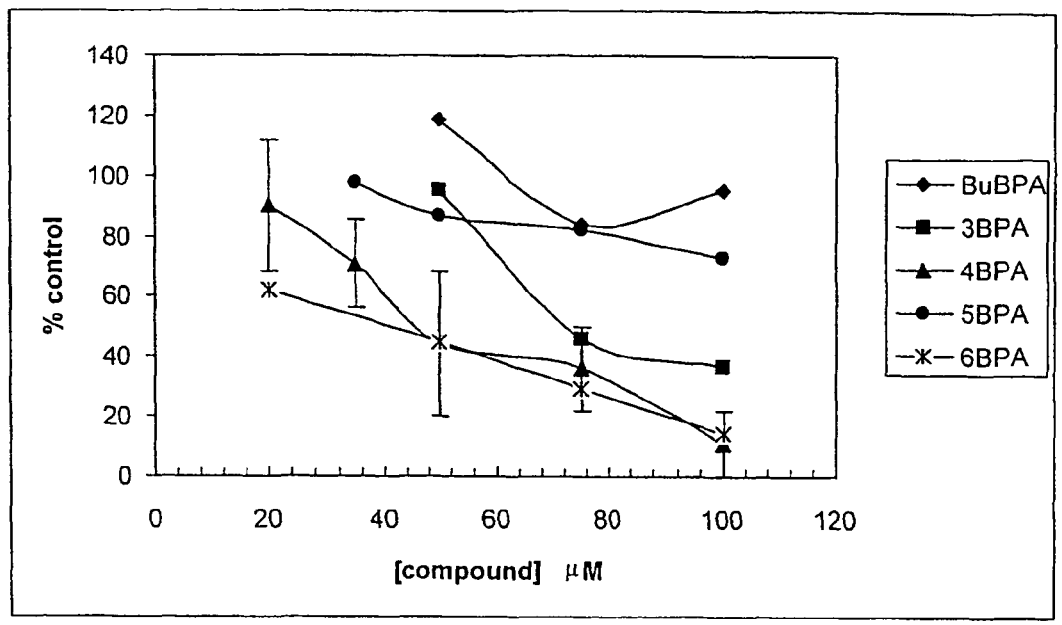
FIG. 7 is a graph of macrophage viability, as measured by the MTT macrophage J774 viability assay, expressed as % of control, after 24 hour exposure to compound, for several examples of biphenylacetyl (BPA) compounds: ABD-0040 (BuBPA), ABD-0041 (3BPA), ABD-0042 (4BPA), ABD-0043 (5BPA), ABD-0044 (6BPA). Unless shown, error bars are less than 20%.

The results for various biphenylacetyl (BPA) compounds, ABD-0040 (BuBPA), ABD-0041 (3BPA), ABD-0042 (4BPA), ABD-0043 (5BPA), and ABD-0044 (6BPA), using the MTT macrophage J774 viability assay, are illustrated in FIG. 7.

Again, the butanediol derivative, compound ABD-0042 (4BPA), is very active, as is the hexanediol derivative, compound ABD-0044 (6BPA). Since BPA (4-biphenyl acetic acid; also known as Felbinac), like ibuprofen, is a COX inhibitor, some of the effects may be due to suppression of prostaglandin synthesis.

Figure 8:
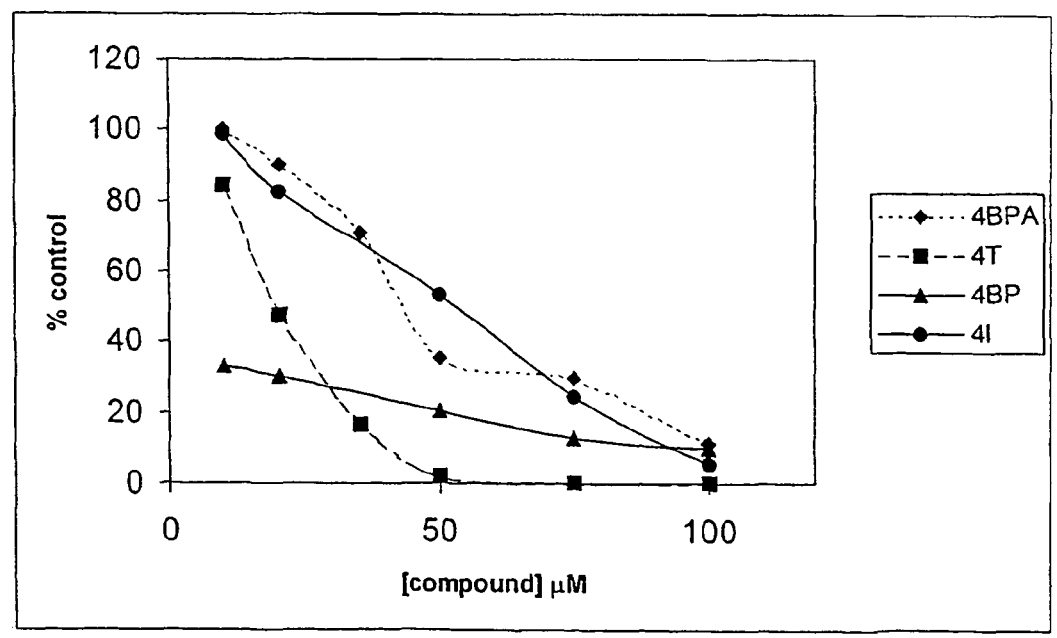
FIG. 8 is a graph of macrophage viability, as measured by the MTT macrophage J774 viability assay, expressed as % of control, after 24 hour exposure to compound, for several examples of butanediol compounds: ABD-0042 (4BPA), ABD-0028 (4T), ABD-0056 (4BP), ABD-0036 (41).

The results for various butanediol derivatives, ABD-0042 (4BPA), ABD-0028 (4T), ABD-0056 (4BP), ABD-0036 (4I), using the MTT macrophage J774 viability assay, are also illustrated in FIG. 8.

Figure 9:
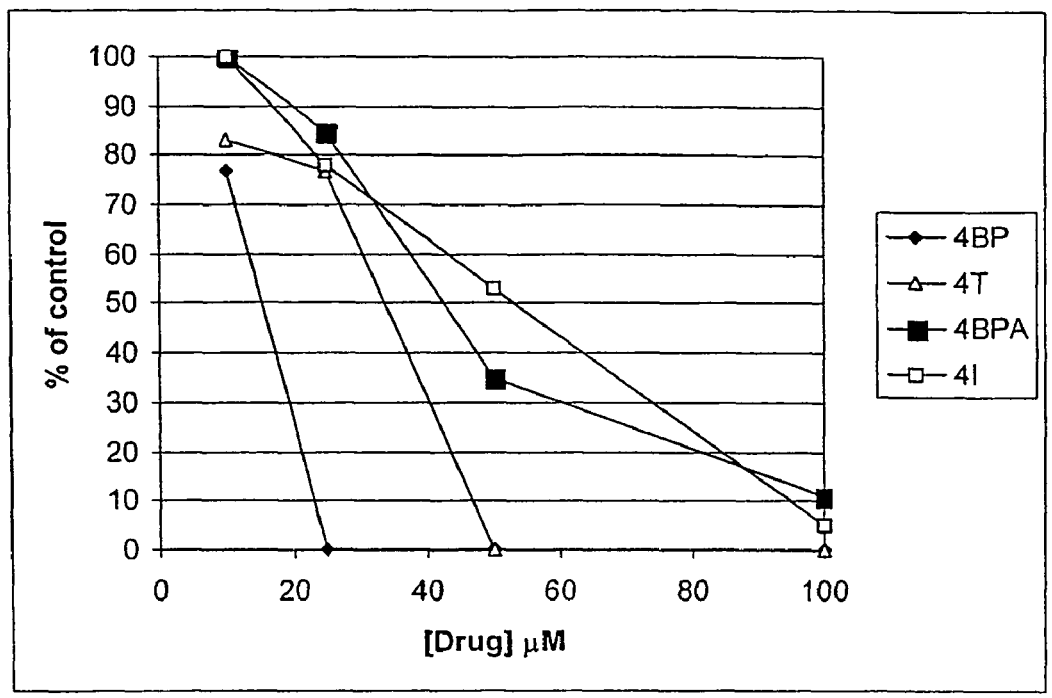
FIG. 9 is a graph of macrophage viability, as measured by the Alamar Blue macrophage J774 viability assay, expressed as % of control, after 72 hour exposure to compound, for several examples of butanediol compounds: ABD-0042 (4BPA), ABD-0028 (4T), ABD-0056 (4BP), ABD-0036 (41).

The results for various butanediol derivatives, ABD-0042 (4BPA), ABD-0028 (4T), ABD-0056 (4BP), ABD-0036 (4I), using the Alamar Blue macrophage J774 viability assay, are also illustrated in FIG. 9.

Figure 10:
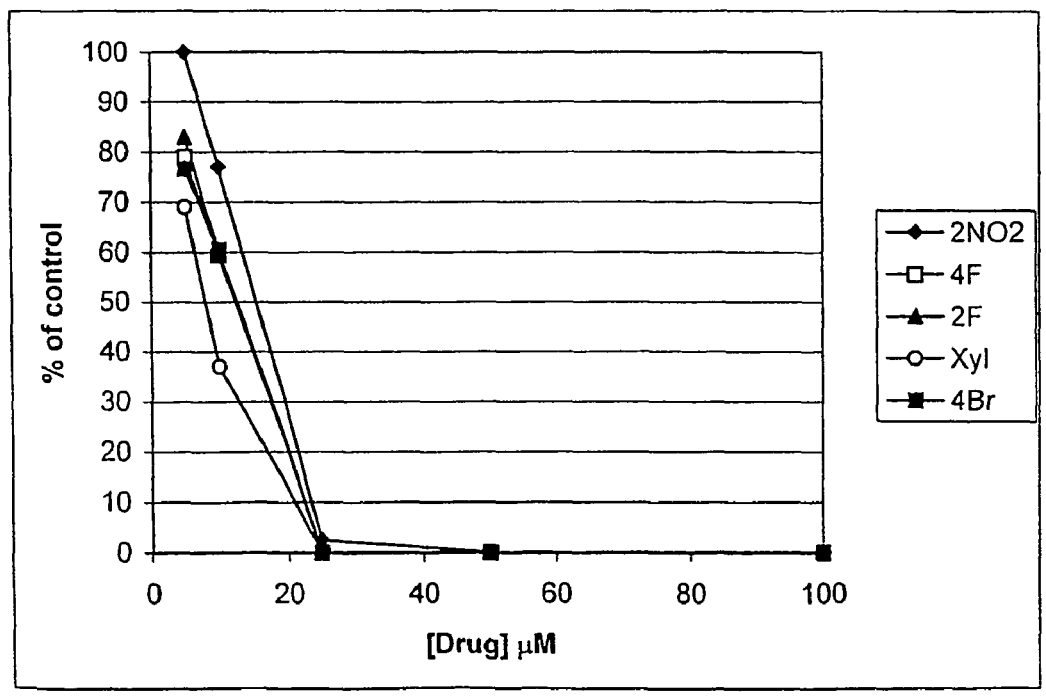
FIG. 10 is a graph of macrophage viability, as measured by the Alamar Blue macrophage J774 viability assay, expressed as % of control, after 72 hour exposure to compound, for ABD-0098 ("2NO$_2$"), ABD-0100 ("4F"), ABD-0099 ("2F"), ABD-0089 ("Xyl"), and ABD-0102 ("4Br").

The results for various substituted biphenyl (BP) compounds, ABD-0098 ("2NO2"), ABD-0100 ("4F"), ABD-0099 ("2F"), ABD-0089 ("Xyl"), and ABD-0102 ("4Br"), using the Alamar Blue macrophage J774 viability assay, are illustrated in FIG. 10.

Figure 11:
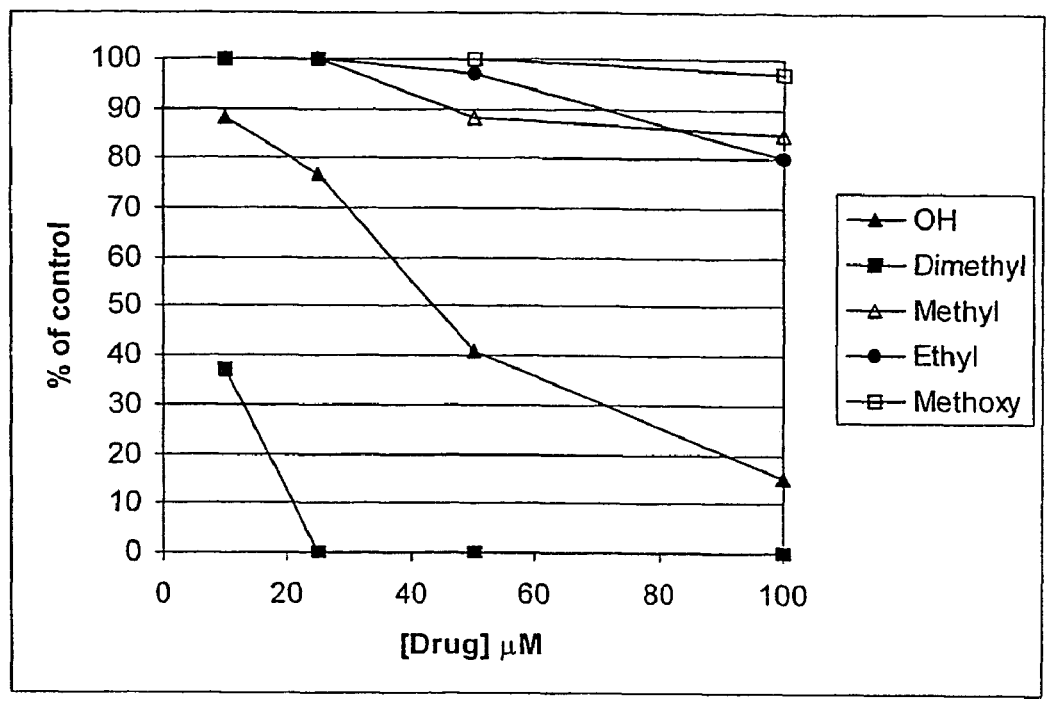
FIG. 11 is a graph of macrophage viability, as measured by the Alamar Blue macrophage J774 viability assay, expressed as % of control, after 72 hour exposure to compound, for ABD-0072 ("OH"), ABD-0089 ("Dimethyl"), ABD-0070 ("Methyl"), ABD-0094 ("Ethyl"), and ABD-0097 ("Methoxy").

The results for various substituted biphenyl (BP) compounds, ABD-0072 ("OH"), ABD-0089 ("Dimethyl"), ABD-0070 ("Methyl"), ABD-0094 ("Ethyl"), and ABD-0097 ("Methoxy"), using the Alamar Blue macrophage J774 viability assay, are illustrated in FIG. 11.

Figure 12:
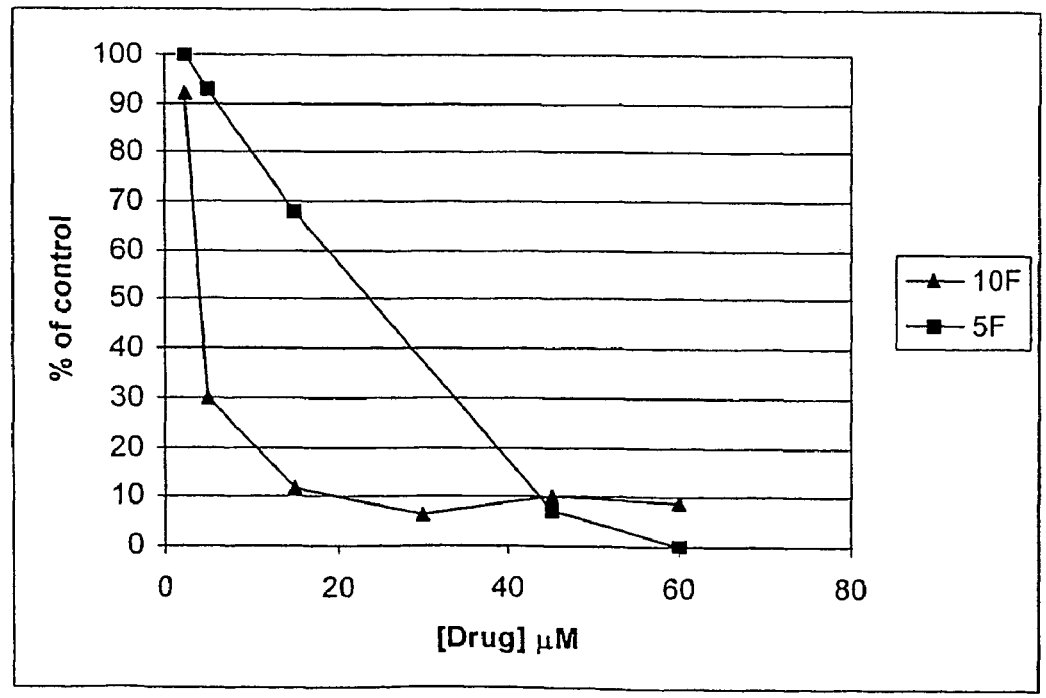
FIG. 12 is a graph of macrophage viability, as measured by the Alamar Blue macrophage J774 viability assay, expressed as % of control, after 72 hour exposure to compound, for ABD-0085 (10F) and ABD-0077 (5F).

The results for two fluoro-substituted phenyl compounds, ABD-0085 ("10F") and ABD-0077 ("5F"), using the Alamar Blue macrophage J774 viability assay, are illustrated in FIG. 12.

Various butanediol derivatives (ABD-0053 (BuBP), ABD-0057 (3BP), ABD-0056 (4BP), ABD-0055 (5BP), ABD-0054 (6BP)) were further evaluated using the murine co-culture system and the rabbit osteoclast culture system, and osteoclast number and resorption pit area recorded as a function of compound concentration.

Figure 13:
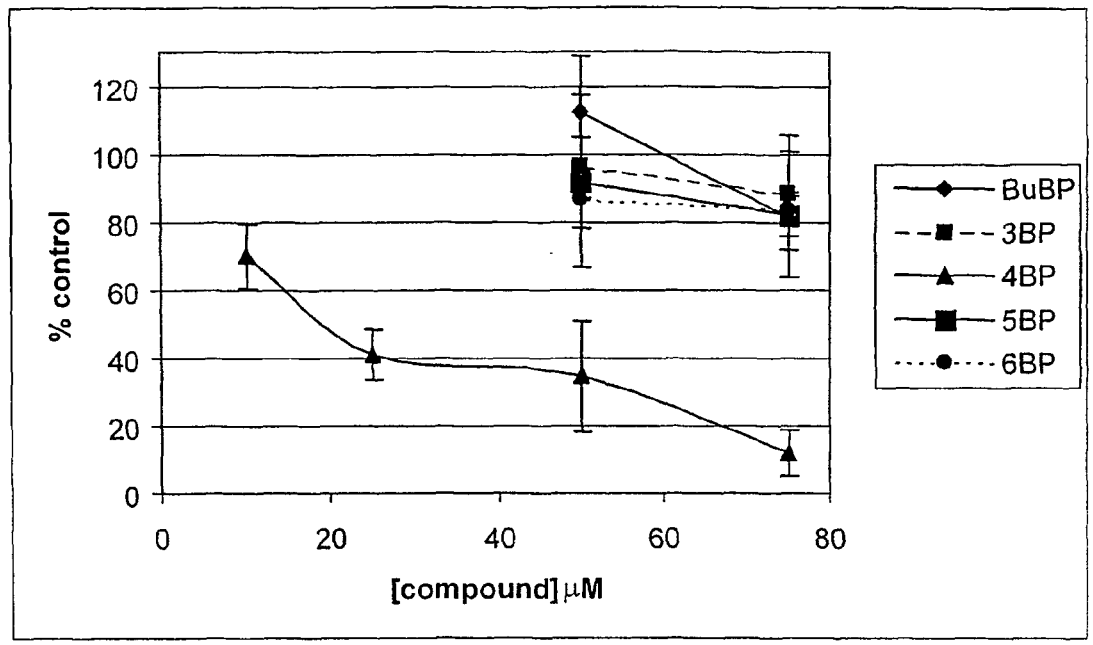
FIG. 13 is a graph showing the effects of compounds in the rabbit osteoclast culture system, and is a plot of the number of rabbit osteoclasts, expressed as a % of control value, after three days exposure to compound, as a function of compound concentration, for several examples of biphenylcarboxy (BP) derivatives: ABD-0053 (BuBP), ABD-0057 (3BP), ABD-0056 (4BP), ABD-0055 (5BP), ABD-0054 (6BP).

The results for osteoclast number for the rabbit osteoclast culture system are illustrated in FIG. 13.

Figure 14:
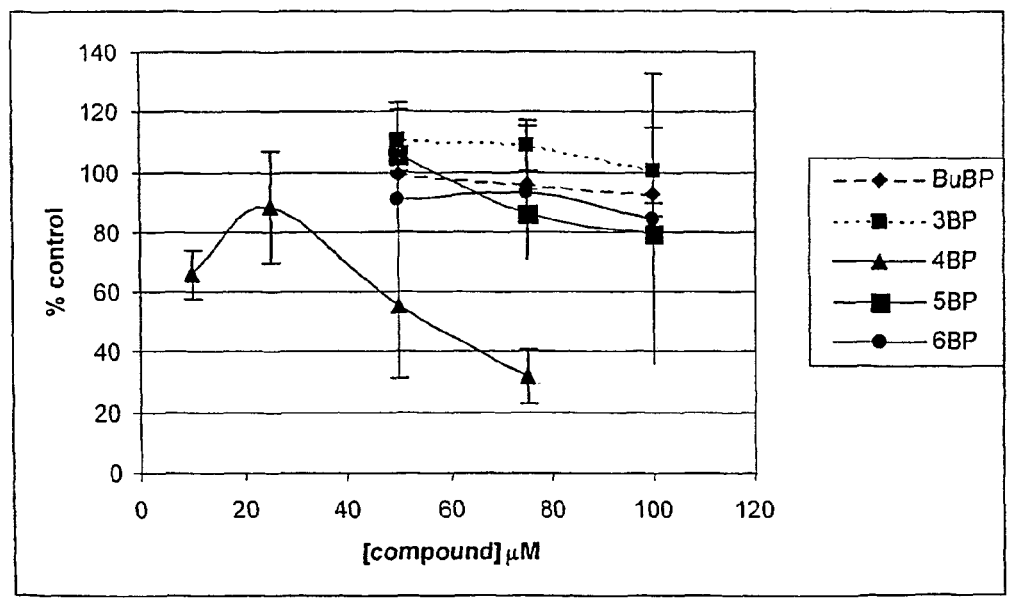
FIG. 14 is a graph showing the effects of compounds in the rabbit osteoclast culture system, and is a plot of resorption pit area expressed as a % of control, after three days exposure to compound, as a function of compound concentration, for several examples of biphenylcarboxy (BP) derivatives: ABD-0053 (BuBP), ABD-0057 (3BP), ABD-0056 (4BP), ABD- 0055 (5BP), ABD-0054 (6BP). Each value represents an average of 3 experiments, each of which had 5 data points.

The results for resorption pit area for the rabbit osteoclast culture system are illustrated in FIG. 14.

It was possible to investigate the effects of compounds upon the osteoclast precursors by adding the test compounds at the Day 2 stage of the co-culture procedure. The test compounds were added and left in contact with the cell culture for 2 days. A 100% medium change was then performed, as it is desirable to remove all of the test compound. This must be done very carefully without touching or disturbing the cell layer. Were any compound to remain then it would complicate the results by potentially killing osteoclasts as well as their precursors and not give an accurate indication of the toxicity specifically towards precursors.

Figure 15:
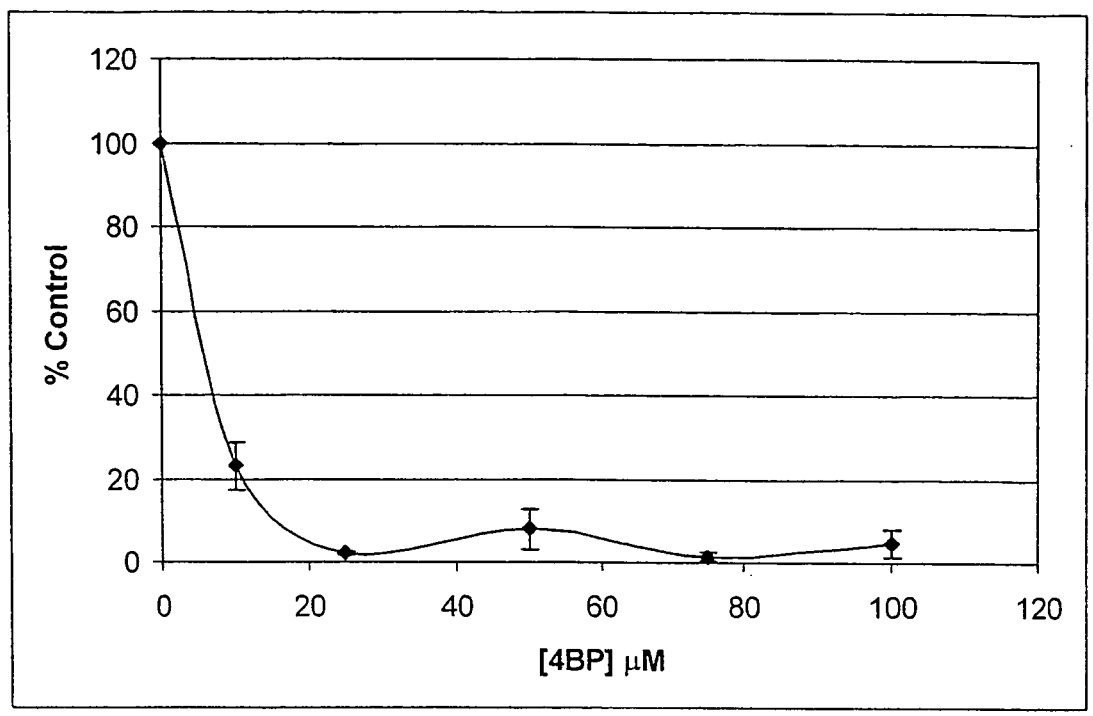
FIG. 15 is a graph showing the effects of compounds in the murine co-culture system, and is a plot of the number of murine osteoclasts, expressed as a % of control value as a function of compound concentration, for ABD-0056 (4BP). The compound is added at Day 2 and there is a complete medium refresh after Day 4 to remove the compound. The experiment is terminated at Day 10 and the number of osteoclasts ascertained by TRAcP staining. Each value represents an average of 3 experiments, each of which had 5 data points.

The results for osteoclast number for the murine co-culture system, where test compound was added at Day 2, removed at Day 4 and incubation continued until Day 10 (osteoclast precursors), are illustrated in FIG. 15.

Figure 16:
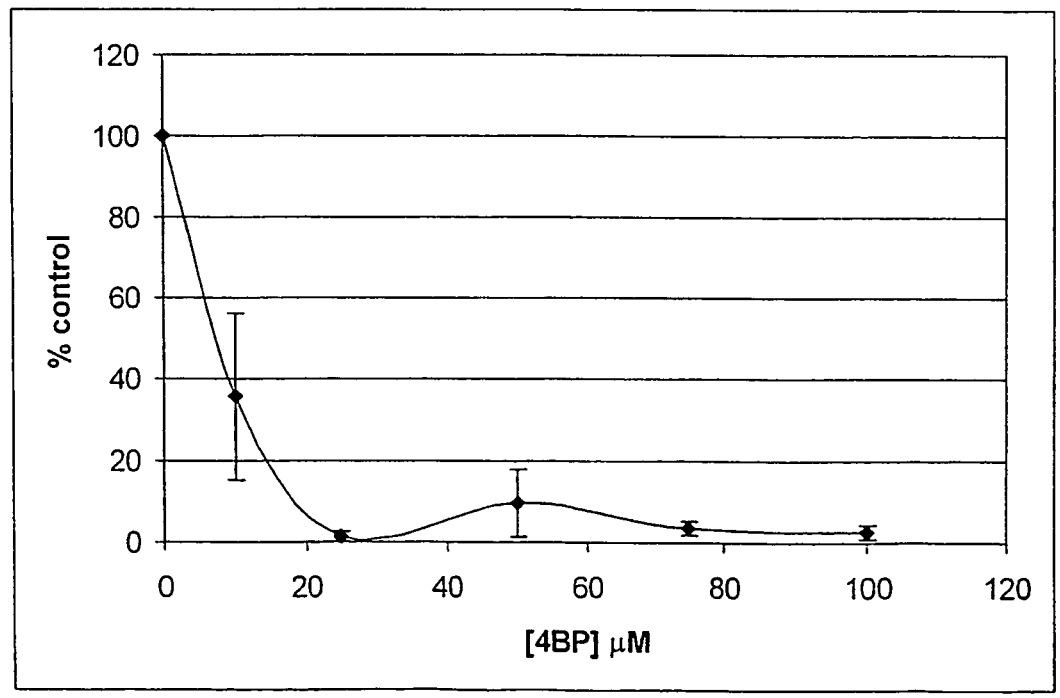
FIG. 16 is a graph showing the effects of compounds in the murine co-culture system, and is a plot of resorption pit area expressed as a % of control value as a function of compound concentration, for ABD-0056 (4BP). The compound is added at Day 2 and there is a complete medium refresh after Day 4 to remove the compound. The experiment is terminated at Day 10 and the amount of resorption measured by reflected light microscopy. Each value represents an average of 3 experiments, each of which had 5 data points.

The results for resorption pit area for the murine co-culture system, where test compound was added at Day 2, removed at Day 4 and incubation continued until Day 10 (osteoclast precursors), are illustrated in FIG. 16.

FIG. 15 shows that ABD-0056 (4BP) is even more effective against osteoclast precursor formation than against mature osteoclasts. As a potential treatment for disorders involving excess bone removal, this suggests ABD-0056 (4BP) is a very potent drug capable of strongly inhibiting the formation of osteoclasts, and then demonstrating a high degree of toxicity towards those that do develop. The same pattern is demonstrated by studies on the levels of osteoclast-induced resorption, as shown in FIG. 16. At all concentrations tested, there is virtually no resorption seen.

Figure 17:
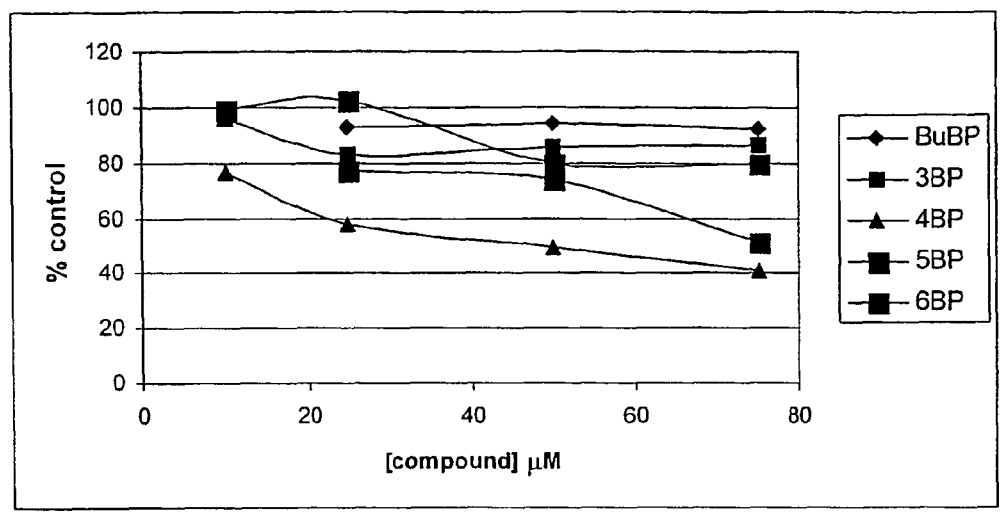
FIG. 17 is a graph showing the effects of compounds in the murine co-culture system, and is a plot of the number of murine osteoclasts, expressed as a % of control value, after three days exposure to compound added at Day 7, as a function of compound concentration, for several examples of biphenylcarboxy (BP) derivatives: ABD-0053 (BuBP), ABD-0057 (3BP), ABD-0056 (4BP), ABD-0055 (5BP), ABD-0054 (6BP).

The results for osteoclast number for the murine co-culture system, where test compound was added at Day 7, and incubation continued until Day 10 (mature osteoclasts), are illustrated in FIG. 17.

Figure 18:
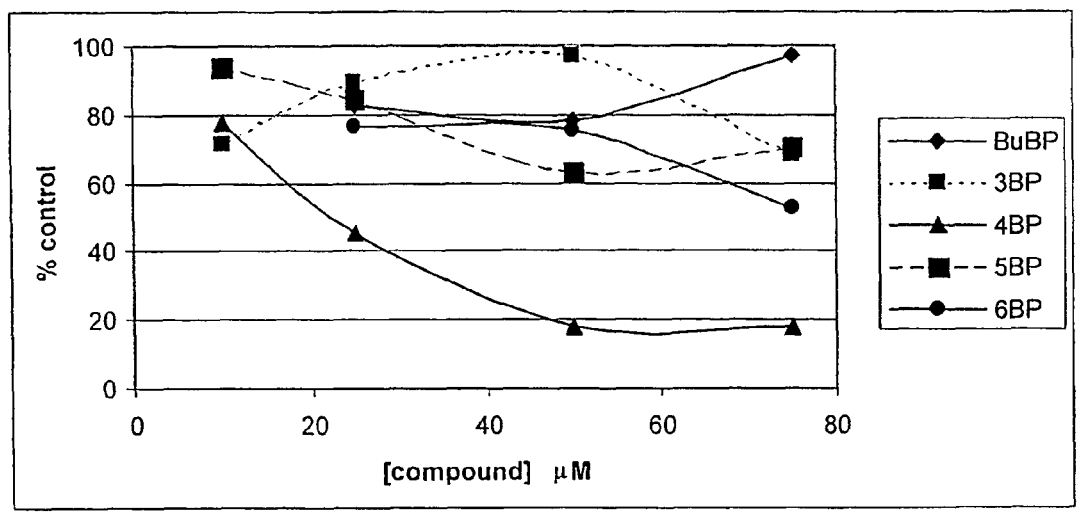
FIG. 18 is a graph showing the effects of compounds in the murine co-culture system, and is a plot of resorption pit area expressed as a % of control, after three days exposure to compound added at Day 7, as a function of compound concentration, for several examples of biphenylcarboxy (BP) derivatives: ABD-0053 (BuBP), ABD-0057 (3BP), ABD-0056 (4BP), ABD-0055 (5BP), ABD-0054 (6BP). Each value represents an average of 3 experiments, each of which had 5 data points.

The results for resorption pit area for the murine co-culture system, where test compound was added at Day 7, and incubation continued until Day 10 (mature osteoclasts), are illustrated in FIG. 18.

Compounds ABD-0056 (4BP) and ABD-0054 (6BP) significantly reduced rabbit osteoclast numbers and resorption activity. Additionally, ABD-0056 (4BP) showed a significant effect at concentrations down to 10 µM. Compounds ABD-0056 (4BP) and ABD-0054 (6BP) also significantly inhibited osteoclast formation in the murine co-culture system.

The effects on resorption pit area were more pronounced in the murine co-culture than in the rabbit osteoclast system. In the rabbit system, mature, resorbing osteoclasts are present from the start and may resorb bone for some time, until the compound starts affecting the cells. The co-culture system, however, depends on the actual formation of osteoclasts from non-resorbing precursors.

Figure 19:
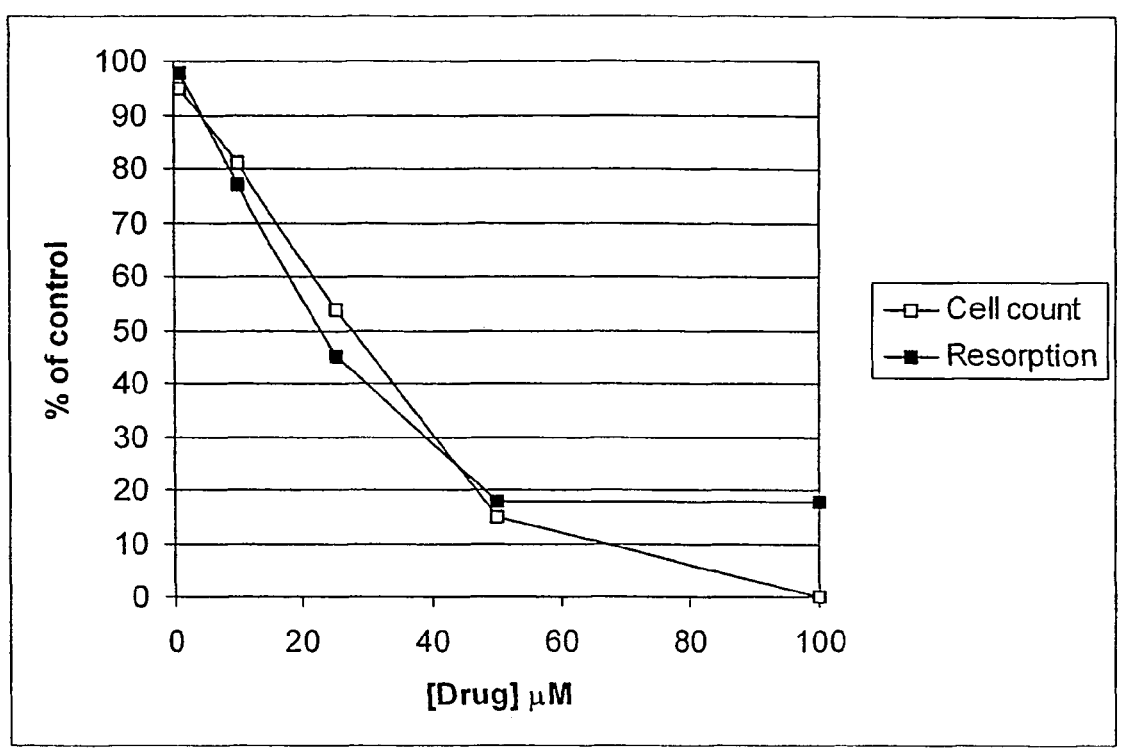
FIG. 19 is a graph of osteoclast number and resorption pit area for the murine co-culture system, where ABD-0056 (4BP) was added at Day 7, and incubation continued until Day 10 (mature osteoclasts).

The results for osteoclast number and resorption pit area for the murine co-culture system, where test compound (ABD-0056) (4BP) was added at Day 7, and incubation continued until Day 10 (mature osteoclasts), are illustrated in FIG. 19.

The results show that the 1,4-butanediol ester of biphenylcarboxylic acid (compound ABD-0056 (4BP)) is a potent inhibitor of osteoclast survival, formation and activity, and is 10 times more effective than any compounds of this class (other than ABD-0085 (10F)).

In a comparable study on J774 survival (see, e.g., reference Luckman et al., 1998), the bisphophonates alendronate and pamidronate had IC50 values that were 10 and 8 times higher respectively.

Without wishing to be bound by any particular theory, it is believed that the biphenylcarboxylic acid conveys the lipophilicity needed for the compound to pass across the cell membrane.

Additional esters of 1,4-butanediol were prepared and tested, specifically, the naphth-1-ylacetyl (compound ABD-0032 (4N)), homoveratryl (compound ABD-0033 (4H)), 2-biphenylcarboxy (compound ABD-0059 (4BPX)) and 4-phenyltoluyl (compound ABD-0034 (4PT)) derivatives. These compounds showed little activity at 100 µM concentration.

Without wishing to be bound to any particular theory, it is believed that the activity of the compounds is related to the overall shape of the molecule. The I, BP and BPA derivatives can be regarded as broadly linear, whereas the BPX and N derivatives are bent out of the linear plane. That the H and PT derivatives are inactive suggests that the molecular target will only accommodate a specific size of compound, and that the homoveratrate compound is too small or insufficiently lipophilic and the phenyltoluate compound is too long or too flexible.

It is believed that one preferred class of compounds will be of a generally rigid, cylindrical shape, and be based on the biphenyl structure. A sub-class of such compounds are those with a further 4'-substituent on the biphenyl group.

Another sub-class of such compounds are those with further 2'- and 4'-substituents on the biphenyl group. Another sub-class of such compounds are those with further 2-, 2'- and 4'-substituents on the biphenyl group.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined by the appended claims.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Armour K. J., et al., 2001, "Inhibition of bone resorption in vitro and prevention of ovariectomy-induced bone loss in vivo by flurbiprofen nitroxybutylester (HCT1026)," Arthritis Rheum., Vol. 44, No. 9, pp. 2185-2192.

Blum, H., et al., 1978, "Diphosphonoalkane Carboxylic Acids, Process of Preparation and Methods of Use," U.S. Pat. No. 4,077,997.

Coxon, F. P., Helfrich, M. H., Van't Hof, R., Sebti, S., Ralston, S. H., Hamilton, A., and Rogers, M. J., 2000, "Protein geranylgeranylation is required for osteoclast formation, function, and survival: inhibition by bisphosphonates and GGTI-298," J. Bone Miner. Res., Vol. 15, pp. 1467-1476.

Degenhardt and Burdsall, 1986, "Synthesis of Ethenylidenebis(phosphonic acid) and its Tetraalkyl Esters," J. Org. Chem., Vol. 51, pp. 3488-3490.

Eberhard and Westheimer, 1965, "Hydrolysis of Phostonates," J. Amer. Chem. Soc., Vol. 87, pp. 252-260.

Herczegh et al, 2002, "Osteoadsorptive Bisphosphonate Derivatives of Fluoroquinolone Antibacterials," J. Med. Chem., Vol. 45, pp. 2338-2341.

Hughes, D. E., Boyce, B. F., 1997, "Apoptosis in bone physiology and disease," Molecular Pathology, Vol. 50, pp. 132-137.

Kong, Y. Y., Yoshida, H., Sarosi, I., Tan, H. L., Timms, E., Capparelli, C., et al, 1999, "OPGL is a key regulator of osteoclastogenesis, lymphocyte development and lymph-node organogenesis," Nature, Vol. 397, pp. 315-323.

Luckman, S. P., Coxon, F. P., Ebetino, F. H., Russell, R. G., and Rogers, M. J., 1998, "Heterocycle-containing bisphosphonates cause apoptosis and inhibit bone resorption by preventing protein prenylation: evidence from structure-activity relationships in J774 macrophages," J. Bone Miner. Res., Vol. 13, pp. 1668-1678.

Luckman, S. P.; Coxon, F. P.; Ebetino, F. H.; Russell, R. G.; Rogers, M. J., 1998, "Heterocycle-containing bisphosphonates cause apoptosis and inhibit bone resorption by preventing protein prenylation: evidence from structure-activity relationships in J774 macrophages," J. Bone Miner. Res., Vol. 13, pp. 1668-1678,1998.

MacPherson, H; Noble, B. S.;. Ralston, S. H., 1999, "Expression and functional role of nitric oxide synthase isoforms in human osteoblast-like cells," *Bone*, Vol. 24, pp. 0.179-185.

Miyaura, N. and Suzuki, A., 1995, "Palladium-catalysed cross-coupling reactions of organoboron compounds," *Chem. Rev.*, Vol. 95, No. 7, pp. 2457-2483.

Mundy, G. R., 1996, *Bone Remodelling and its disorders* (2nd edition), London: Martin Dunitz.

Nociari, M. N., et al., 1998, "A Novel one-step, highly sensitive fluorimetric assay to evaluate cell-mediated cytotoxicity," *Journal of Immunological Methods*, Vol. 213, pp. 157-167.

Raisz, L. G., 1988, "Local and systemic factors in the pathogenesis of osteoporosis," *N. Enql. J. Med.*, Vol. 318, pp. 818-828.

Ralston, S. H., 1997, "Science, Medicine and the Future: Osteoporosis," *Br. Med. J.*, Vol. 315, pp. 469-472.

Rodan, G. A., Harada, S., 1997, "The missing bone," *Cell*, Vol. 89, pp. 677-680.

Takahashi, N.; Akatsu, T.; Udagawa, N.; Sasaki, T.; Yamaguchi, A.; Moseley, J. M.; Martin, T. J.; Suda, T., 1988, "Osteoblastic cells are involved in osteoclast formation," *Endocrinology*, Vol. 123, pp. 2600-2602, 1988.

van't Hof, R. J., and Ralston, S. H., 1997, "Cytokine-induced nitric oxide inhibits bone resorption by inducing apoptosis of osteoclast progenitors and suppressing osteoclast activity," *J. Bone Miner. Res.*, Vol. 12, pp. 1797-804.

Yasuda, H., Shima, N., Nakagawa, N., Mochizuki, S. I., Yano, K., Fujise, N., et al, 1998, "Identity of osteoclastogenesis inhibitory factor (OCIF) and osteoprotegerin (OPG): a mechanism by which OPG/OCIF inhibits osteoclastogenesis in vitro," *Endocrinology*, Vol. 139, pp. 1329-1337.

The invention claimed is:

1. A compound selected from compounds of the following formula:

$$R^{A1}-C(=O)-O-A-OH$$

wherein:

A is —$(CH_2)_n$— where n is an integer from 4 to 8;

$R^{A1}$ is independently a group of the following formula:

[structure with $R^P_q$ and $R^P_r$ substituents on biphenyl]

wherein q is an integer from 0 to 4, r is an integer from 0 to 5, and each $R^P$ is independently selected from:
-Me, -Et, -iPr, -nPr, -tBu, -Ph, —F, —Cl, —Br, —I, —OH, —C(=O)OH, —C(=O)OMe, —C(=O)OEt, —C(=O)O(tBu), —C(=O)OPh, —OC(C=O)Me, —OC(C=O)Et, —OC(C=O)(tBu), —OC(C=O)Ph, —OC(C=O)OMe, —OC(C=O)OEt, —OC(C=O)O(tBu), —OC(C=O)OPh, —C(=O)$NH_2$, —C(=O)NHMe, —C(=O)$NMe_2$, —C(=O)NHPh, —NHC(=O)Me, —NHC(=O)Et, —NHC(=O)Ph, —$NH_2$, —NHme, —$NMe_2$, —NHEt, —$NEt_2$, —$NO_2$, —CN, —S(=O)$_2$OMe, —S(=O)$_2$OEt, and —S(=O)$_2$OPh;

and pharmaceutically acceptable salts thereof.

2. A compound according to claim 1, wherein $R^{A1}$ is independently a group of the following formula:

[biphenyl structure with $R^P_q$ and $R^P_r$ substituents]

3. A compound according to claim 1, wherein $R^{A1}$ is independently a group of the following formula:

[biphenyl structure with $R^P_s$ and $R^P$ substituents]

wherein s is an integer from 0 to 4.

4. A compound according to claim 1, wherein $R^{A1}$ is independently a group of the following formula:

[biphenyl structure with $R^P$ substituent]

5. A compound according to claim 1, wherein $R^{A1}$ is independently a group of the following formula:

[biphenyl structure with $R^P$ and $R^P_s$ substituents]

wherein s is an integer from 0 to 4.

6. A compound according to claim 1, wherein $R^{A1}$ is independently group of the following formula:

[biphenyl structure with $R^P$ substituent]

7. A compound according to claim 1, wherein $R^{A1}$ is independently a group of the following formula:

[biphenyl structure with $R^P$, $R^P$, and $R^P_t$ substituents]

wherein t is an integer from 0 to 3.

8. A compound according to claim 1, wherein $R^{A1}$ is independently a group of the following formula:

[biphenyl structure with $R^P$ and $R^P$ substituents]

9. A compound according to claim 1, wherein $R^{A1}$ is independently a group of the following formula:

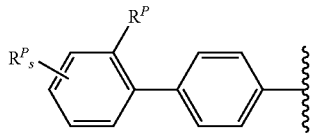

wherein s is an integer from 0 to 4.

10. A compound according to claim 1, wherein $R^{A1}$ is independently a group of the following formula:

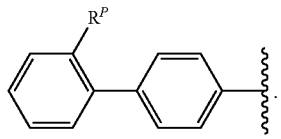

11. A compound according to claim 1, wherein $R^{A1}$ is independently a group of the following formula:

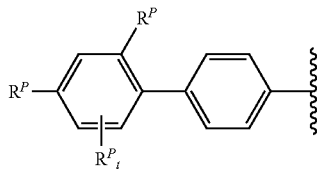

wherein t is an integer from 0 to 3.

12. A compound according to claim 1, wherein $R^{A1}$ is independently a group of the following formula:

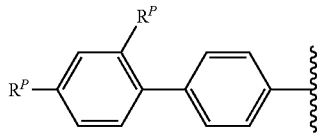

13. A compound according to claim 1, wherein $R^{A1}$ is independently a group of the following formula:

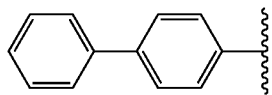

14. A compound according to claim 2, wherein A is a group of the formula —$(CH_2)_4$—.

15. A compound according to claim 2, wherein A is a group of the formula —$(CH_2)_5$—.

16. A compound according to claim 2, wherein A is a group of the formula —$(CH_2)_6$—.

17. A compound according to claim 3, wherein A is a group of the formula —$(CH_2)_4$—.

18. A compound according to claim 3, wherein A is a group of the formula —$(CH_2)_5$—.

19. A compound according to claim 3, wherein A is a group of the formula —$(CH_2)_6$—.

20. A compound according to claim 4, wherein A is a group of the formula —$(CH_2)_4$—.

21. A compound according to claim 4, wherein A is a group of the formula —$(CH_2)_5$—.

22. A compound according to claim 4, wherein A is a group of the formula —$(CH_2)_6$—.

23. A compound according to claim 5, wherein A is a group of the formula —$(CH_2)_4$—.

24. A compound according to claim 5, wherein A is a group of the formula —$(CH_2)_5$—.

25. A compound according to claim 5, wherein A is a group of the formula —$(CH_2)_6$—.

26. A compound according to claim 9, wherein A is a group of the formula —$(CH_2)_4$—.

27. A compound according to claim 9, wherein A is a group of the formula —$(CH_2)_5$—.

28. A compound according to claim 9, wherein A is a group of the formula —$(CH_2)_6$—.

29. A compound according to claim 10, wherein A is a group of the formula —$(CH_2)_4$—.

30. A compound according to claim 10, wherein A is a group of the formula —$(CH_2)_5$—.

31. A compound according to claim 10, wherein A is a group of the formula —$(CH_2)_6$—.

32. A compound according to claim 11, wherein A is a group of the formula —$(CH_2)_4$—.

33. A compound according to claim 11, wherein A is a group of the formula —$(CH_2)_5$—.

34. A compound according to claim 11, wherein A is a group of the formula —$(CH_2)_6$—.

35. A compound according to claim 12, wherein A is a group of the formula —$(CH_2)_4$—.

36. A compound according to claim 12, wherein A is a group of the formula —$(CH_2)_5$—.

37. A compound according to claim 12, wherein A is a group of the formula —$(CH_2)_6$—.

38. A compound according to claim 14, wherein each $R^P$ is independently selected from: -Me, -Et, -iPr, -nPr, -tBu, -Ph, —F, —Cl, —Br, —I, —OH, —$NH_2$—NHMe, —$NMe_2$—NHEt, —$NEt_2$, —$NO_2$—CN, —$S(=O)_2OMe$, —$S(=O)_2OEt$ and —$S(=O)_2OPh$.

39. A compound according to claim 15, wherein each $R^P$ is independently selected from:
-Me, -Et, -iPr, -nPr, -tBu, -Ph, —F, —Cl, —Br, —I, —OH, —$NH_2$, —NHMe, —$NMe_2$, —NHEt, —$NEt_2$, —$NO_2$, —CN, —$S(=O)_2OMe$ —$S(=O)_2OEt$ and —$S(=O)_2OPh$.

40. A compound according to claim 16, wherein each $R^P$ is independently selected from: -Me, -Et, -iPr, -nPr, -tBu, -Ph, —F, —Cl, —Br, —I, —OH, —$NH_2$—NHMe, —$NMe_2$—NHEt, —$NEt_2$, —$NO_2$—CN, —$S(=O)_2OMe$ —$S(=O)_2OEt$ and —$S(=O)_2OPh$.

41. A compound according to claim 17, wherein each $R^P$ is independently selected from: -Me, -Et, -iPr, -nPr, -tBu, -Ph, —F, —Cl, —Br, —I, —OH, —$NH_2$, —NHMe, —$NMe_2$, —NHEt, —$NEt_2$, —$NO_2$—CN, —$S(=O)_2OMe$, —$S(=O)_2OEt$, and —$S(=O)_2OPh$.

42. A compound according to claim 18, wherein each $R^P$ is independently selected from: -Me, -Et, -iPr, -nPr, -tBu, -Ph, —F, —Cl, —Br, —I, —OH, —$NH_2$—NHMe, —$NMe_2$—NHEt, —$NEt_2$, —$NO_2$—CN, —$S(=O)_2OMe$, —$S(=O)_2OEt$ and —$S(=O)_2OPh$.

43. A compound according to claim 19, wherein each $R^P$ is independently selected from: -Me, -Et, -iPr, -nPr, -tBu, -Ph, —F, —Cl, —Br, —I, —OH, —$NH_2$, —NHMe, —$NMe_2$, —NHEt, —$NEt_2$, —$NO_2$, —CN, —$S(=O)_2OMe$, —$S(=O)_2OEt$, and —$S(=O)_2OPh$.

44. A compound according to claim 20, wherein each $R^P$ is independently selected from: -Me, -Et, -iPr, -nPr, -tBu, -Ph, —F, —Cl, —Br, —I, —OH, —$NH_2$—NHMe, —$NMe_2$—NHEt, —$NEt_2$, —$NO_2$—CN, —$S(=O)_2OMe$, —$S(=O)_2OEt$ and —$S(=O)_2OPh$.

45. A compound according to claim 21, wherein each $R^P$ is independently selected from: -Me, -Et, -iPr, -nPr, -tBu, -Ph, —F, —Cl, —Br, —I, —OH, —$NH_2$, —NHMe, —$NMe_2$,

46. A compound according to claim 22, wherein each $R^P$ is independently selected from: -Me, -Et, -iPr, -nPr, -tBu, -Ph, —F, —Cl, —Br, —I, —OH, —NH$_2$, —NHMe, —NMe$_2$— NHEt, —NEt$_2$, —NO$_2$—CN, —S(=O)$_2$OMe, —S(=O)$_2$OEt, and —S(=O)$_2$OPh.

47. A compound according to claim 23, wherein each $R^P$ is independently selected from: -Me, -Et, -iPr, -nPr, -tBu, -Ph, —F, —Cl, —Br, —I, —OH, —NH$_2$, —NHMe, —NMe$_2$, —NHEt, —NEt$_2$, —NO$_2$—CN, —S(=O)$_2$OMe, —S(=O)$_2$OEt, and —S(=O)$_2$OPh.

48. A compound according to claim 24, wherein each $R^P$ is independently selected from: -Me, -Et, -iPr, -nPr, -tBu, -Ph, —F, —Cl, —Br, —I, —OH, —NH$_2$—NHMe, —NMe$_2$— NHEt, —NEt$_2$, —NO$_2$—CN, —S(=O)$_2$OMe, —S(=O)$_2$OEt, and —S(=O)$_2$OPh.

49. A compound according to claim 25, wherein each $R^P$ is independently selected from: -Me, -Et, -iPr, -nPr, -tBu, -Ph, —F, —Cl, —Br, —I, —OH, —NH —NHMe, —NMe$_2$, —NHEt, —NEt$_2$, —NO$_2$, —CN, —S(=O)$_2$OMe, —S(=O)$_2$ OEt, and —S(=O)$_2$OPh.

50. A compound according to claim 26, wherein each $R^P$ is independently selected from: -Me, -Et, -iPr, -nPr, -tBu, -Ph, —F, —Cl, —Br, —I, —OH, —NH$_2$—NHMe, —NMe$_2$— NHEt, —NEt$_2$, —NO$_2$—CN, —S(=O)$_2$OMe, —S(=O)$_2$OEt, and —S(=O)$_2$OPh.

51. A compound according to claim 27, wherein each $R^P$ is independently selected from: -Me, -Et, -iPr, -nPr, -tBu, -Ph, —F, —Cl, —Br, —I, —OH, —NH$_2$, —NHMe, —NMe$_2$, —NHEt, —NEt$_2$, —NO$_2$—CN, —S(=O)$_2$OMe, —S(=O)$_2$OEt, and —S(=O)$_2$OPh.

52. A compound according to claim 28, wherein each $R^P$ is independently selected from: -Me, -Et, -iPr, -nPr, -tBu, -Ph, —F, —Cl, —Br, —I, —OH, —NH$_2$—NHMe, —NMe$_2$— NHEt, —NEt$_2$, —NO$_2$—CN, —S(=O)$_2$OMe, —S(=O)$_2$OEt, and —S(=O)$_2$OPh.

53. A compound according to claim 29, wherein each $R^P$ is independently selected from: -Me, -Et, -iPr, -nPr, -tBu, -Ph, —F, —Cl, —Br, —I, —OH, —NH$_2$, —NHMe, —NMe$_2$, —NHEt, —NEt —NO$_2$—CN, —S(=O)$_2$OMe, —S(=O)$_2$OEt and —S(=O)$_2$OPh.

54. A compound according to claim 30, wherein each $R^P$ is independently selected from: -Me, -Et, -iPr, -nPr, -tBu, -Ph, —F, —Cl, —Br, —I, —OH, —NH$_2$—NHMe, —NMe$_2$— NHEt, —NEt$_2$, —NO$_2$—CN, —S(=O)$_2$OMe, —S(=O)$_2$OEt and —S(=O)$_2$OPh.

55. A compound according to claim 31, wherein each $R^P$ is independently selected from: -Me, -Et, -iPr, -nPr, -tBu, -Ph, —F, —Cl, —Br, —I, —OH, —NH$_2$, —NHMe, —NMe$_2$, —NHEt, —NEt$_2$, —NO$_2$—CN, —S(=O)$_2$OMe, —S(=O)$_2$OEt and —S(=O)$_2$OPh.

56. A compound according to claim 32, wherein each $R^P$ is independently selected from: -Me, -Et, -iPr, -nPr, -tBu, -Ph, —F, —Cl, —Br, —I, —OH, —NH$_2$—NHMe, —NMe$_2$— NHEt, —NEt$_2$, —NO$_2$—CN, —S(=O)$_2$OMe, —S(=O)$_2$OEt, and —S(=O)$_2$OPh.

57. A compound according to claim 33, wherein each $R^P$ is independently selected from: -Me, -Et, -iPr, -nPr, -tBu, -Ph, —F, —Cl, —Br, —I, —OH, —NH —NHMe, —NMe$_2$, —NHEt, —NEt$_2$, —NO$_2$, —CN, —S(=O)$_2$OMe, —S(=O)$_2$ OEt, and —S(=O)$_2$OPh.

58. A compound according to claim 34, wherein each $R^P$ is independently selected from: -Me, -Et, -iPr, -nPr, -tBu, -Ph, —F, —Cl, —Br, —I, —OH, —NH$_2$—NHMe, —NMe$_2$— NHEt, —NEt$_2$, —NO$_2$—CN, —S(=O)$_2$OMe, —S(=O)$_2$OEt, and —S(=O)$_2$OPh.

59. A compound according to claim 35, wherein each $R^P$ is independently selected from: -Me, -Et, -iPr, -nPr, -tBu, -Ph, —F, —Cl, —Br, —I, —OH, —NH —NHMe, —NMe$_2$, —NHEt, —NEt$_2$, —NO$_2$, —CN, —S(=O)$_2$OMe, —S(=O)$_2$ OEt, and —S(=O)$_2$OPh.

60. A compound according to claim 36, wherein each $R^P$ is independently selected from: -Me, -Et, -iPr, -nPr, -tBu, -Ph, —F, —Cl, —Br, —I, —OH, —NH$_2$—NHMe, —NMe$_2$— NHEt, —NEt$_2$, —NO$_2$—CN, —S(=O)$_2$OMe, —S(=O)$_2$OEt, and —S(=O)$_2$OPh.

61. A compound according to claim 37, wherein each $R^P$ is independently selected from: -Me, -Et, -iPr, -nPr, -tBu, -Ph, —F, —Cl, —Br, —I, —OH, —NH$_2$, —NHMe, —NMe$_2$, —NHEt, —NEt$_2$, —NO$_2$, —CN, —S(=O)$_2$OMe, —S(=O)$_2$OEt and —S(=O)$_2$OPh.

62. A compound according to claim 14, wherein each $R^P$ is independently selected from: -Me, —F, —Cl, —Br, —I, —OH, —NH$_2$, —NMe$_2$, —NO$_2$, and —CN.

63. A compound according to claim 15, wherein each $R^P$ is independently selected from: -Me, —F, —Cl, —Br, —I, —OH, —NH$_2$, —NMe$_2$, —NO$_2$, and —CN.

64. A compound according to claim 16, wherein each $R^P$ is independently selected from: -Me, —F, —Cl, —Br, —I, —OH, —NH$_2$, —NMe$_2$, —NO$_2$, and —CN.

65. A compound according to claim 17, wherein each $R^P$ is independently selected from: -Me, —F, —Cl, —Br, —I, —OH, —NH$_2$, —NMe$_2$, —NO$_2$, and —CN.

66. A compound according to claim 18, wherein each $R^P$ is independently selected from: -Me, —F, —Cl, —Br, —I, —OH, —NH$_2$, —NMe$_2$, —NO$_2$, and —CN.

67. A compound according to claim 19, wherein each $R^P$ is independently selected from: -Me, —F, —Cl, —Br, —I, —OH, —NH$_2$, —NMe$_2$, —NO$_2$, and —CN.

68. A compound according to claim 20, wherein each $R^P$ is independently selected from: -Me, —F, —Cl, —Br, —I, —OH, —NH$_2$, —NMe$_2$, —NO$_2$, and —CN.

69. A compound according to claim 21, wherein each $R^P$ is independently selected from: -Me, —F, —Cl, —Br, —I, —OH, —NH$_2$, —NMe$_2$, —NO$_2$, and —CN.

70. A compound according to claim 22, wherein each $R^P$ is independently selected from: -Me, —F, —Cl, —Br, —I, —OH, —NH$_2$, —NMe$_2$, —NO$_2$, and —CN.

71. A compound according to claim 23, wherein each $R^P$ is independently selected from: -Me, —F, —Cl, —Br, —I, —OH, —NH$_2$, —NMe$_2$, —NO$_2$, and —CN.

72. A compound according to claim 24, wherein each $R^P$ is independently selected from: -Me, —F, —Cl, —Br, —I, —OH, —NH$_2$, —NMe$_2$, —NO$_2$, and —CN.

73. A compound according to claim 25, wherein each $R^P$ is independently selected from: -Me, —F, —Cl, —Br, —I, —OH, —NH$_2$, —NMe$_2$, —NO$_2$, and —CN.

74. A compound according to claim 26, wherein each $R^P$ is independently selected from: -Me, —F, —Cl, —Br, —I, —OH, —NH$_2$, —NMe$_2$, —NO$_2$, and —CN.

75. A compound according to claim 27, wherein each $R^P$ is independently selected from: -Me, —F, —Cl, —Br, —I, —OH, —NH$_2$, —NMe$_2$, —NO$_2$, and —CN.

76. A compound according to claim 28, wherein each $R^P$ is independently selected from: -Me, —F, —Cl, —Br, —I, —OH, —NH$_2$, —NMe$_2$, —NO$_2$, and —CN.

77. A compound according to claim 29, wherein each $R^P$ is independently selected from: -Me, —F, —Cl, —Br, —I, —OH, —NH$_2$, —NMe$_2$, —NO$_2$, and —CN.

78. A compound according to claim 30, wherein each $R^P$ is independently selected from: -Me, —F, —Cl, —Br, —I, —OH, —NH$_2$, —NMe$_2$, —NO$_2$, and —CN.

79. A compound according to claim 31, wherein each $R^P$ is independently selected from: -Me, —F, —Cl, —Br, —I, —OH, —NH$_2$, —NMe$_2$, —NO$_2$, and —CN.

80. A compound according to claim 32, wherein each $R^P$ is independently selected from: -Me, —F, —Cl, —Br, —I, —OH, —NH$_2$, —NMe$_2$, —NO$_2$, and —CN.

81. A compound according to claim 33, wherein each $R^P$ is independently selected from: -Me, —F, —Cl, —Br, —I, —OH, —NH$_2$, —NMe$_2$, —NO$_2$, and —CN.

82. A compound according to claim 34, wherein each $R^P$ is independently selected from: -Me, —F, —Cl, —Br, —I, —OH, —NH$_2$, —NMe$_2$, —NO$_2$, and —CN.

83. A compound according to claim 35, wherein each $R^P$ is independently selected from: -Me, —F, —Cl, —Br, —I, —OH, —NH$_2$, —NMe$_2$, —NO$_2$, and —CN.

84. A compound according to claim 36, wherein each $R^P$ is independently selected from: -Me, —F, —Cl, —Br, —I, —OH, —NH$_2$, —NMe$_2$, —NO$_2$, and —CN.

85. A compound according to claim 37, wherein each $R^P$ is independently selected from: -Me, —F, —Cl, —Br, —I, —OH, —NH$_2$, —NMe$_2$, —NO$_2$, and —CN.

86. A compound according to claim 1, wherein the compound is selected from compounds of the following formulae, and pharmaceutically acceptable salts thereof:

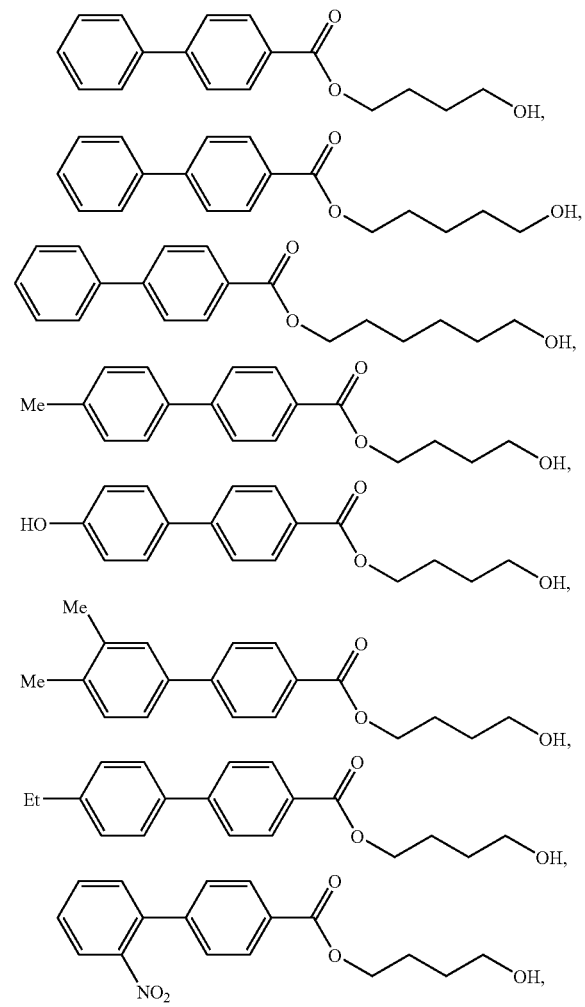

-continued

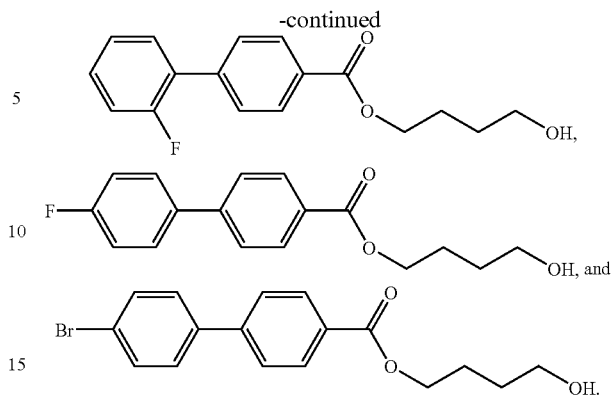

87. A compound according to claim 1, wherein the compound is selected from compounds of the following formula, and pharmaceutically acceptable salts thereof:

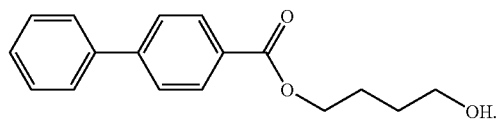

88. A compound according to claim 1, wherein the compound is selected from compounds of the following formula:

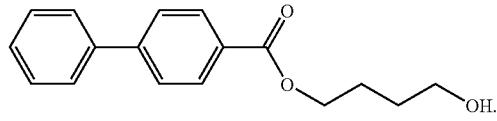

89. A composition comprising a compound according to claim 1 and a pharmaceutically acceptable carrier or diluent.

90. A composition comprising a compound according to claim 2 and a pharmaceutically acceptable carrier or diluent.

91. A composition comprising a compound according to claim 62 and a pharmaceutically acceptable carrier or diluent.

92. A composition comprising a compound according to claim 86 and a pharmaceutically acceptable carrier or diluent.

93. A composition comprising a compound according to claim 3 and a pharmaceutically acceptable carrier or diluent.

94. A composition comprising a compound according to claim 87 and a pharmaceutically acceptable carrier or diluent.

95. A composition comprising a compound according to claim 88 and a pharmaceutically acceptable carrier or diluent.

96. A compound according to claim 2, wherein each $R^P$ is independently selected from: -Me, —F, —Cl, —Br, and —I.

97. A compound according to claim 3, wherein each $R^P$ is independently selected from: -Me, —F, —Cl, —Br, and —I.

98. A compound according to claim 14, wherein each $R^P$ is independently selected from: -Me, —F, —Cl, —Br, and —I.

99. A compound according to claim 17, wherein each $R^P$ is independently selected from: -Me, —F, —Cl, —Br, and —I.

100. A compound selected from compounds of the following formula:

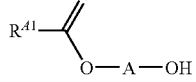

wherein:
A is —(CH$_2$)$_4$—, —(CH$_2$)$_5$—, or —(CH$_2$)$_6$—;
R$^{A1}$ is independently a group of the following formula:
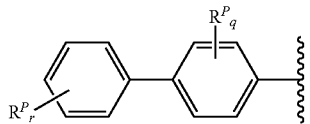
wherein:
q is 0 or 1;
r is 0, 1, or 2; and
each R$^P$ is independently -Me, —F, —Cl, —Br, —I, —OH, —NH$_2$, —NMe$_2$, —NO$_2$, or —CN;
and pharmaceutically acceptable salts thereof.
* * * * *